(12) United States Patent
Leung et al.

(10) Patent No.: US 9,402,677 B2
(45) Date of Patent: Aug. 2, 2016

(54) METHODS AND DEVICES FOR CRYOGENIC CAROTID BODY ABLATION

(71) Applicant: Cibiem, Inc., Los Altos, CA (US)

(72) Inventors: Mark S. Leung, Duncan (CA); Zoar Jacob Engelman, Salt Lake City, UT (US); Martin M. Grasse, San Francisco, CA (US); Mark Gelfand, New York, NY (US); Howard Levin, Teaneck, NJ (US)

(73) Assignee: CIBIEM, INC., Los Altos, CA (US)

( * ) Notice: Subject to any disclaimer, the term of this patent is extended or adjusted under 35 U.S.C. 154(b) by 467 days.

(21) Appl. No.: 13/908,853

(22) Filed: Jun. 3, 2013

(65) Prior Publication Data

US 2013/0324987 A1 Dec. 5, 2013

Related U.S. Application Data

(60) Provisional application No. 61/654,221, filed on Jun. 1, 2012, provisional application No. 61/666,384, filed on Jun. 29, 2012, provisional application No. 61/798,847, filed on Mar. 15, 2013.

(51) Int. Cl.
*A61B 18/02* (2006.01)
*A61B 18/14* (2006.01)
*A61B 18/00* (2006.01)

(52) U.S. Cl.
CPC ............ *A61B 18/0218* (2013.01); *A61B 18/02* (2013.01); *A61B 18/1492* (2013.01); *A61B 2018/00041* (2013.01); *A61B 2018/00285* (2013.01); *A61B 2018/00291* (2013.01);

(Continued)

(58) Field of Classification Search
CPC ............... A61B 18/02; A61B 18/0218; A61B 2018/0212; A61B 2018/0225; A61B 2018/0262; A61B 2018/0293; A61B 2018/00345
USPC ....................................... 606/20–26; 607/113
See application file for complete search history.

(56) References Cited

U.S. PATENT DOCUMENTS

| | | | |
|---|---|---|---|
| 3,650,277 | A | 3/1972 | Sjostrand et al. |
| 4,011,872 | A | 3/1977 | Komiya |

(Continued)

FOREIGN PATENT DOCUMENTS

| | | |
|---|---|---|
| CN | 1440256 A | 9/2003 |
| DE | 10151797 A1 | 5/2003 |

(Continued)

OTHER PUBLICATIONS

Giannoni et al.; Clinical significance of chemosensitivity in chronic heart failure: influence on neurohormonal derangement, cheyne-strokes respiration and arrhythmias; Clinical Science (London); 114(7); pp. 489-497; Apr. 2008.

(Continued)

*Primary Examiner* — Michael Peffley
*Assistant Examiner* — Thomas Giuliani
(74) *Attorney, Agent, or Firm* — Shay Glenn LLP

(57) ABSTRACT

Methods and cryogenic devices for assessing, and treating patients having sympathetically mediated disease, involving augmented peripheral chemoreflex and heightened sympathetic tone by reducing chemosensor input to the nervous system via carotid body ablation. Some methods include advancing a cryo-ablation catheter into a patient's vasculature and ablating tissue within a carotid septum.

5 Claims, 28 Drawing Sheets

(52) U.S. Cl.
CPC .......... *A61B2018/00345* (2013.01); *A61B 2018/00577* (2013.01); *A61B 2018/0212* (2013.01); *A61B 2018/0262* (2013.01); *A61B 2018/0293* (2013.01); *A61B 2090/3782* (2016.02)

(56) References Cited

U.S. PATENT DOCUMENTS

| | | | |
|---|---|---|---|
| 4,201,219 A | 5/1980 | Bozal Gonzalez | |
| 4,791,931 A | 12/1988 | Slate | |
| 4,960,133 A | 10/1990 | Hewson | |
| 5,139,496 A | 8/1992 | Hed et al. | |
| 5,354,271 A | 10/1994 | Voda | |
| 5,476,495 A | 12/1995 | Kordis et al. | |
| 5,893,863 A | 4/1999 | Yoon | |
| 5,906,580 A | 5/1999 | Kline-Schoder et al. | |
| 5,916,213 A | 6/1999 | Haissaguerre et al. | |
| 5,919,187 A | 7/1999 | Guglielmi et al. | |
| 5,957,882 A | 9/1999 | Nita et al. | |
| 6,004,269 A | 12/1999 | Crowley et al. | |
| 6,068,629 A | 5/2000 | Haissaguerre et al. | |
| 6,071,279 A | 6/2000 | Whayne et al. | |
| 6,125,857 A | 10/2000 | Silber | |
| 6,129,359 A | 10/2000 | Haas et al. | |
| 6,182,666 B1 | 2/2001 | Dobak, III | |
| 6,217,576 B1 | 4/2001 | Tu et al. | |
| 6,228,082 B1 | 5/2001 | Baker et al. | |
| 6,235,024 B1 | 5/2001 | Tu | |
| 6,379,348 B1 | 4/2002 | Onik | |
| 6,402,746 B1 | 6/2002 | Whayne et al. | |
| 6,411,852 B1 | 6/2002 | Danek et al. | |
| 6,497,705 B2 | 12/2002 | Comben | |
| 6,522,926 B1 | 2/2003 | Kieval et al. | |
| 6,544,187 B2 | 4/2003 | Seward | |
| 6,656,136 B1 | 12/2003 | Weng et al. | |
| 6,660,013 B2 | 12/2003 | Rabiner et al. | |
| 6,673,066 B2 | 1/2004 | Werneth | |
| 6,905,497 B2 | 6/2005 | Truckai et al. | |
| 6,937,903 B2 | 8/2005 | Schuler et al. | |
| 7,097,641 B1 | 8/2006 | Arless et al. | |
| 7,137,963 B2 | 11/2006 | Nita et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,207,989 B2 | 4/2007 | Pike et al. | |
| 7,363,076 B2 | 4/2008 | Yun et al. | |
| 7,617,005 B2 | 11/2009 | Demarais et al. | |
| 7,628,785 B2 | 12/2009 | Hadjicostis et al. | |
| 7,736,360 B2 | 6/2010 | Mody et al. | |
| 7,738,952 B2 | 6/2010 | Yun et al. | |
| 7,766,961 B2 | 8/2010 | Patel et al. | |
| 7,853,333 B2 | 12/2010 | Demarais | |
| 7,901,450 B2 | 3/2011 | Johnson et al. | |
| 7,922,663 B2 | 4/2011 | Tran et al. | |
| 7,925,352 B2 | 4/2011 | Stack et al. | |
| 7,959,628 B2 | 6/2011 | Schaer et al. | |
| 8,002,728 B2 | 8/2011 | Chang | |
| 8,060,206 B2 * | 11/2011 | Kieval | A61B 5/02028 607/17 |
| 8,075,554 B2 | 12/2011 | Malecki et al. | |
| 8,116,883 B2 | 2/2012 | Williams et al. | |
| 8,157,760 B2 | 4/2012 | Criado et al. | |
| 8,167,805 B2 | 5/2012 | Emery et al. | |
| 8,192,425 B2 | 6/2012 | Mirza et al. | |
| 8,192,760 B2 | 6/2012 | Hossainy et al. | |
| 8,292,879 B2 | 10/2012 | Manwaring et al. | |
| 8,295,912 B2 | 10/2012 | Gertner | |
| 8,308,709 B2 | 11/2012 | Chang | |
| 8,326,429 B2 | 12/2012 | Wenzel et al. | |
| 8,364,237 B2 | 1/2013 | Stone et al. | |
| 8,374,674 B2 | 2/2013 | Gertner | |
| 8,396,548 B2 | 3/2013 | Perry et al. | |
| 8,409,200 B2 | 4/2013 | Holcomb et al. | |
| 8,433,423 B2 | 4/2013 | Demarais | |
| 8,465,752 B2 | 6/2013 | Seward | |
| 8,469,904 B2 | 6/2013 | Gertner | |
| 8,568,399 B2 | 10/2013 | Azamian et al. | |
| 8,620,423 B2 | 12/2013 | Demarais et al. | |
| 9,060,784 B2 | 6/2015 | Coe et al. | |
| 9,089,541 B2 | 7/2015 | Azamian | |
| 2001/0041890 A1 | 11/2001 | Hassett et al. | |
| 2002/0087151 A1 | 7/2002 | Mody et al. | |
| 2002/0128639 A1 | 9/2002 | Pless et al. | |
| 2003/0009125 A1 | 1/2003 | Nita et al. | |
| 2004/0116921 A1 | 6/2004 | Sherman et al. | |
| 2004/0210239 A1 | 10/2004 | Nash et al. | |
| 2005/0096642 A1 | 5/2005 | Appling et al. | |
| 2005/0096710 A1 | 5/2005 | Kieval | |
| 2005/0143378 A1 | 6/2005 | Yun et al. | |
| 2005/0153885 A1 | 7/2005 | Yun et al. | |
| 2005/0288656 A1 | 12/2005 | Koerner et al. | |
| 2006/0064137 A1 | 3/2006 | Stone | |
| 2006/0111754 A1 | 5/2006 | Rezai et al. | |
| 2006/0135962 A1 | 6/2006 | Kick et al. | |
| 2006/0195149 A1 | 8/2006 | Hopper et al. | |
| 2006/0224110 A1 | 10/2006 | Scott et al. | |
| 2006/0253161 A1 | 11/2006 | Libbus et al. | |
| 2006/0259084 A1 | 11/2006 | Zhang et al. | |
| 2006/0282131 A1 | 12/2006 | Caparso et al. | |
| 2006/0287679 A1 | 12/2006 | Stone | |
| 2007/0015006 A1 | 1/2007 | Lee et al. | |
| 2007/0112327 A1 | 5/2007 | Yun et al. | |
| 2007/0135875 A1 | 6/2007 | Demarais et al. | |
| 2007/0142879 A1 * | 6/2007 | Greenberg | A61F 2/07 607/62 |
| 2007/0150006 A1 | 6/2007 | Libbus et al. | |
| 2007/0156179 A1 | 7/2007 | Karashurov | |
| 2007/0265609 A1 | 11/2007 | Thapliyal et al. | |
| 2007/0299476 A1 | 12/2007 | Park et al. | |
| 2008/0009916 A1 | 1/2008 | Rossing et al. | |
| 2008/0009917 A1 | 1/2008 | Rossing et al. | |
| 2008/0039727 A1 | 2/2008 | Babaev | |
| 2008/0045936 A1 | 2/2008 | Vaska et al. | |
| 2008/0058871 A1 | 3/2008 | Libbus et al. | |
| 2008/0086181 A1 | 4/2008 | Amurthur et al. | |
| 2009/0299362 A1 | 12/2009 | Long et al. | |
| 2010/0063564 A1 | 3/2010 | Libbus et al. | |
| 2010/0070004 A1 | 3/2010 | Hlavka | |
| 2010/0152590 A1 | 6/2010 | Moore et al. | |
| 2010/0168731 A1 | 7/2010 | Wu et al. | |
| 2010/0168739 A1 | 7/2010 | Wu et al. | |
| 2010/0217151 A1 | 8/2010 | Gostout et al. | |
| 2010/0262013 A1 | 10/2010 | Smith et al. | |
| 2010/0268307 A1 | 10/2010 | Demarais et al. | |
| 2010/0274219 A1 | 10/2010 | Wenzel et al. | |
| 2011/0009854 A1 | 1/2011 | Babkin et al. | |
| 2011/0040297 A1 | 2/2011 | Babkin et al. | |
| 2011/0066085 A1 | 3/2011 | Weng et al. | |
| 2011/0098699 A1 | 4/2011 | Pachon Mateos et al. | |
| 2011/0104060 A1 | 5/2011 | Seward | |
| 2011/0118598 A1 | 5/2011 | Gertner | |
| 2011/0118600 A1 * | 5/2011 | Gertner | A61B 8/06 600/439 |
| 2011/0130708 A1 | 6/2011 | Perry et al. | |
| 2011/0144631 A1 | 6/2011 | Elkins et al. | |
| 2011/0172529 A1 | 7/2011 | Gertner | |
| 2011/0208096 A1 | 8/2011 | Demarais et al. | |
| 2011/0208174 A1 | 8/2011 | Baust | |
| 2011/0208175 A1 | 8/2011 | Sobotka et al. | |
| 2011/0251487 A1 | 10/2011 | Magnin et al. | |
| 2011/0251607 A1 | 10/2011 | Kruecker et al. | |
| 2011/0257561 A1 | 10/2011 | Gertner et al. | |
| 2011/0257562 A1 | 10/2011 | Schaer | |
| 2011/0301587 A1 | 12/2011 | Deem et al. | |
| 2012/0016226 A1 | 1/2012 | Gertner | |
| 2012/0059437 A1 * | 3/2012 | Shalev | A61N 1/05 607/62 |
| 2012/0065492 A1 | 3/2012 | Gertner et al. | |
| 2012/0065494 A1 | 3/2012 | Gertner et al. | |
| 2012/0078248 A1 | 3/2012 | Worrell et al. | |
| 2012/0095335 A1 | 4/2012 | Sverdlik et al. | |
| 2012/0095371 A1 | 4/2012 | Sverdlik et al. | |
| 2012/0095372 A1 | 4/2012 | Sverdlik et al. | |
| 2012/0095461 A1 | 4/2012 | Herscher et al. | |

(56) References Cited

U.S. PATENT DOCUMENTS

| | | |
|---|---|---|
| 2012/0101018 A1 | 4/2012 | Miracle et al. |
| 2012/0109018 A1 | 5/2012 | Gertner et al. |
| 2012/0130368 A1 | 5/2012 | Jenson |
| 2012/0157992 A1 | 6/2012 | Smith et al. |
| 2012/0157993 A1 | 6/2012 | Jenson et al. |
| 2012/0172680 A1 | 7/2012 | Gelfand et al. |
| 2012/0172723 A1 | 7/2012 | Gertner |
| 2012/0184952 A1 | 7/2012 | Jenson et al. |
| 2012/0199616 A1 | 8/2012 | Lamb et al. |
| 2012/0232436 A1 | 9/2012 | Warnking |
| 2012/0238918 A1 | 9/2012 | Gertner |
| 2012/0245494 A1 | 9/2012 | Gertner |
| 2012/0265227 A1 | 10/2012 | Sverdlik et al. |
| 2012/0277763 A1 | 11/2012 | Greenblatt et al. |
| 2013/0066316 A1 | 3/2013 | Steinke et al. |
| 2013/0123778 A1 | 5/2013 | Richardson et al. |
| 2013/0131668 A1 | 5/2013 | Schaer |
| 2013/0197555 A1 | 8/2013 | Schaer |
| 2013/0197614 A1 | 8/2013 | Gustus et al. |
| 2014/0039450 A1 | 2/2014 | Green et al. |
| 2014/0243809 A1 | 8/2014 | Gelfand et al. |
| 2014/0288015 A1 | 9/2014 | Venkateswara-Rao et al. |
| 2014/0350401 A1 | 11/2014 | Sinelnikov |
| 2015/0328452 A1 | 11/2015 | Hlavka et al. |
| 2016/0000499 A1 | 1/2016 | Lennox et al. |

FOREIGN PATENT DOCUMENTS

| | | |
|---|---|---|
| EP | 0819014 B1 | 2/2003 |
| EP | 2008600 A2 | 12/2008 |
| EP | 2488250 A | 8/2012 |
| EP | 1299035 B1 | 2/2013 |
| WO | WO97/25916 A1 | 7/1997 |
| WO | WO98/43701 A1 | 10/1998 |
| WO | WO00/25685 A1 | 5/2000 |
| WO | WO02/069862 A1 | 9/2002 |
| WO | WO03/076008 A1 | 9/2003 |
| WO | WO2004/086936 A2 | 10/2004 |
| WO | WO2004/105807 A2 | 12/2004 |
| WO | WO2007/092330 A1 | 8/2007 |
| WO | WO2007/146834 A2 | 12/2007 |
| WO | WO2008/025855 A2 | 3/2008 |
| WO | WO2009/120953 A2 | 10/2009 |
| WO | WO2010/093603 A1 | 8/2010 |
| WO | WO2010/121738 A1 | 10/2010 |
| WO | WO2010/124120 A1 | 10/2010 |
| WO | WO2010/132703 A1 | 11/2010 |
| WO | WO2011/082278 A1 | 7/2011 |
| WO | WO2011/130531 A2 | 10/2011 |
| WO | WO2012/015720 A1 | 2/2012 |
| WO | WO2012/015721 A1 | 2/2012 |
| WO | WO2012/015722 A1 | 2/2012 |
| WO | WO2012/016135 A1 | 2/2012 |
| WO | WO2012/057916 A1 | 5/2012 |
| WO | WO2012/112165 A1 | 8/2012 |
| WO | WO2012/125172 A1 | 9/2012 |
| WO | WO2013/018083 A2 | 2/2013 |
| WO | WO2013/074813 A1 | 5/2013 |
| WO | WO2013/157011 A2 | 10/2013 |
| WO | WO2015/103539 A1 | 7/2015 |

OTHER PUBLICATIONS

Pennes; Analysis of tissue and arterial blood temperatures in the resting human forearm; J. Appl. Physiol.; 1(2); pp. 93-122; Aug. 1948.

Chernomorsky; U.S. Appl. No. 14/516,312; entitled Percutaneous methods and devices for carotid body ablation, filed Oct. 16, 2014.

Khan et al.; Anatomical variations in human carotid bodies; J. Clin. Pathol.; 41(11); pp. 1196-1199; Nov. 1988.

Holton et al.; The effects of bilateral removal of the carotid bodies and denervation of the carotid sinuses in two human subjects; J. Physiol.; 181(2); pp. 365-378; Nov. 1965.

Petersen et al.; Lesion dimensions during temperature-controlled radiofrequency catheter ablation of left ventricular porcine myocardium impact of ablation site; electrode size, and convective cooling; Circulation; 99(2); pp. 319-325; Jan. 1999.

Sapareto et al.; Thermal dose determination in cancer therapy; Int. J. Radiat. Biol. Phys.; 10(6); pp. 787-800; Jun. 1984.

Sehirli et al.; The diameters of common carotid artery and its branches in newborns; Surg. Radiol. Anat.; 27(4); pp. 292-296; Nov. 2005.

Wittkampf et al.; Control of radiofrequency lesion size by power regulation; Circulation; 80(4); pp. 962-968; Oct. 1989.

Sinelnikov et al.; U.S. Appl. No. 14/656,635 entitled "Carotid body ablation with a transvenous ultrasound imaging and ablation catheter," filed Mar. 12, 2015.

Abboud, F.; In search of autonomic balance: the good, the bad, and the ugly; Am J Physiol Regul Integr Comp Physiol; 298; pp. R1449-R1467; Jun. 2010.

Abdala et al; Hypertension is critically dependent on the carotid body input in the spontaneously hypertensive rat; J Physiol; 590(17); pp. 4269-4277; Sep. 2012.

Abdala et al; Peripheral chemoreceptor inputs contribute to the development of high blood pressure in spontaneously hypertensive rats(proceeding abstract); Proc Physiol Soc 23; PC22; Oxford, England; Jul. 2011 (printed Sep. 24, 2013 from: http://www.physoc.org/proceedings/abstract/Proc%20Physiol%20Soc%2023PC22).

Al-Rawi et al.; Effect of lignocaine injection in carotid sinus on baroreceptor sensitivity during carotid endarterectomy; J Vasc Surg; 39(6); pp. 1288-1294; Jun. 2004.

Anand et al.; Management of the internal carotid artery during carotid body tumor surgery; Laryngoscope; 105; pp. 231-235; Mar. 1995.

Anderson et al. (executive committee); Carotid body resection; J. Allergy Clin. Immunol.; 78(2); pp. 273-275; Aug. 1986.

Arena et al.; Prognostic value of resting end-tidal carbon dioxide in patients with heart failure; Int J Cardiol; 109(3); pp. 351-358; May 2006.

Banzett et al.; Dyspnea and pain: similarities and contrasts between two very unpleasant sensations; APS Bulletin; 11(1); 6 pgs.; Mar./Apr. 2001.

Bencini et al.; The carotid bodies in bronchial asthma; Histopathology; 18; pp. 195-200; Mar. 1991.

Bencini, A.; Reduction of reflex bronchotropic impulses as a result of carotid body surgery; International Surgery; 54(6); pp. 415-423; Dec. 1970.

Bernstein et al.; Current status of glomectomy; (The Amer. Acad. of Allergy, Abstracts of papers given at Ann. Meeting, Feb. 3-7, 1978, Boston MA; J. Allergy; 41(2); pp. 88-89; Feb. 1968.

Bishop, Jr. et al.; Paragangliomas of the neck; Arch Surg.; 127; pp. 1441-1445; Dec. 1992.

Braunwald et al.; Carotid sinus nerve stimulation for the treatment of intractable angina pectoris: surgical technic; Annals of Surgery; 172(5); pp. 870-876; Nov. 1970.

Braunwald et al.; Carotid sinus nerve stimulation in the treatment of angina pectoris and supraventricular tachycardia; The Western Journal of Medicine; 112(3); pp. 41-50; Mar. 1970.

Capps et al.; The late effects of bilateral carotid sinus denervation in man; J Clin Invest; 17(4); pp. 385-389; Jul. 1938.

Chang et al.; Impaired response to hypoxia after bilateral carotid body resection for treatment of bronchial asthma; Chest; 73; pp. 667-669; May 1978.

Curran et al.; Glomectomy for severe bronchial asthma. A double-blind study; Am Rev Respir Dis; 93(1); pp. 84-89; Jan. 1966.

Davidson et al.; Role of the carotid bodies in breath-holding; N Engl J Med; 290(15); pp. 819-822; Apr. 1974.

de Weerd et al.; Prevalence of asymptomatic carotid artery stenosis according to age and sex: Systematic review and metaregression analysis; Stroke; 40(4); pp. 1105-1113; Apr. 2009.

Dickinson et al.; Carotid body tumour: 30 years experience; Br. J. Surg.; 73 (1); pp. 14-16; Jan. 1986.

Ding et al.; Role of blood flow in carotid body chemoreflex function in heart failure; J Physiol; 589(1); pp. 245-258; Jan. 2011.

Doumas et al.; Benefits from treatment and control of patients with resistant hypertension; Int. J Hypertension; 8 pgs; Dec. 2011.

(56) References Cited

OTHER PUBLICATIONS

Fletcher, Jr. et al.; The surgical treatment of bronchial asthma by excision of the carotid body; J Christ Med Assoc India; 38; pp. 492-496; Sep. 1963.
Gain et al.; Anaesthesia for glomectomy in the asthmatic patient; Can Aneas Soc J; 11(4); pp. 417-424; Jul. 1964.
Giannoni et al.; Combined increased chemosensitiviy to hypoxia and hypercapnia as a prognosticator in heart failure; JACC; 53(21); pp. 1975-1980; May 2009.
Grassi, G.; Renal denervation in cardiometabolic disease: Concepts, achievements and perspectives; Nutr Metab Cardiovasc Dis; 23(2); pp. 77-83; Feb. 2013 (Epub Nov. 10, 2012).
Green, M.; Observations on glomectomized asthmatic patients; Annals of Allergy; 23(5); pp. 213-219; May 1965.
Gudovsky et al.; Surgical treatment of bronchial asthma (with translation); Khirurgiia; 7; pp. 14-18; 2002 (year of pub. sufficiently earlier than effective US filing date and any foreign priority date).
Guz et al.; Peripheral chemoreceptor block in man; Respiration Physiology; 1; pp. 38-40; 1966 (year of pub. sufficiently earlier than effective US filing date and any foreign priority date).
Gwon et al.; Risk factors for stroke during surgery for carotid body tumors; World J Surg; 35(9); pp. 2154-2158; Sep. 2011.
Handelsman, H.; Bilateral carotid body resection as a treatment for chronic intractable bronchospastic diseases; Health Technology Assessment Series: Health Technology Assessment Report; No. 12; 13 pgs.; 1985 (year of pub. sufficiently earlier than effective US filing date and any foreign priority date).
Hickey et al.; Bilateral carotid endarterectomy with attempted preservation of the carotid body function; Ann. Surg.; 175(2); pp. 268-273; Feb. 1972.
Honda et al.; Hypoxic chemosensitivity in asthmatic patients two decades after carotid body resection; J Appl Physiol.; 46(4); pp. 632-638; Apr. 1979.
Honda, Y.; Respiratory and circulatory activities in carotid body-resected humans; J Appl Physiol; 73(1); pp. 1-8; Jul. 1992.
Karashurov et al.; Radiofrequency electrostimulation of synocarotid for the treatment of bronchial asthma (with translation); Khirurgiia (Mosk); 12; pp. 4-6; 1999 (year of pub. sufficiently earlier than effective US filing date and any foreign priority date).
Keim, W. F.; Carotid glomectomy in bronchial asthma; Archives of Otolaryngology; 79; pp. 225-228; Mar. 1964.
Kim et al.; Carotid artery-hypoglossal nerve relationships in the neck: an anatomical work; Neurol Res; 31; pp. 895-899; Nov. 2009.
Kline et al.; Cervical glomectomy for bronchial asthma; Journal of the Medical Society of New Jersey; 61(5); pp. 176-178; May 1964.
Leggate, J. M.; Treatment of asthma by excision of the carotid body; Postgraduate Med. Journal; 26(292)pp. 71-77; Feb. 1950.
Lesske et al.; Hypertension caused by chronic intermittent hypoxia—influence of chemoreceptors and sympathetic nervous system; J Hypertens; 15(12); pp. 1593-1603; Dec. 1997.
Lo et al.; Anatomical variations of the common carotid artery bifurcation; Anz J. Surg.; 76(11); pp. 970-972; Nov. 2006.
Lugliani et al.; A role for the carotid body in cardiovascular control in man; Chest; 63(5); pp. 744-750; May 1973.
Lugliani et al.; Effect of bilateral carotid-body resection on ventilatory control at rest and during exercise in man; New England J Med; 285(20); pp. 1105-1111; Nov. 1971.
Lusiani et al.; Prevalence of atherosclerotic involvement of the internal carotid artery in hypertensive patients; Int J Cardiol; 17; pp. 51-56; Oct. 1987.
Lyons et al.; Anatomical variants of the cervical sympathetic chain to be considered during neck dissection; Br J Oral Maxillofac Surg; 36(3); pp. 180-182; Jun. 1998.
Ma et al.; A retrospective study in management of carotid body tumour; Br J Oral Maxillofac Surg; 47(6); pp. 461-465; Sep. 2009.
MacGowan, W.; Removal of the carotid body for asthma: A report of 19 treated patients; Dis Chest; 51(3); pp. 278-281; Mar. 1967.
Marschke et al.; Carotid-body removal in asthma; JAMA; 191(5); p. 397; Feb. 1965.

Marshall, J.; Peripheral chemoreceptors and cardiovascular regulation; Physiological Reviews; 74(3); pp. 543-594; Jul. 1994.
Meyerson, Sheldon; A histological study of the morphology of the cervical carotid bifurcation, including descriptions of intramural neural elements (Thesis); Ohio State University; 47 pgs.; 1968 (year of pub. sufficiently earlier than effective US filing date and any foreign priority date).
Myers et al.; End-tidal CO2 pressure and cardiac performance during exercise in heart failure; Med Sci Sports Exerc; 41(1); pp. 18-24; Jan. 2009.
Nadel et al.; Effect of changes in blood gas tensions and carotid sinus pressure on tracheal volume and total lung resistance to airflow; J Physiol; 163(1); pp. 13-33; Aug. 1962.
Nakayama, K.; Surgical removal of the carotid body for bronchial asthma; Chest; 40(6); pp. 595-604; Dec. 1961.
Nakayama, K.; Surgical removal of the carotid body for bronchial asthma; The Australian and the New Zealand Journal of Surgery; 31(3); pp. 214-221; Feb. 1962.
Nakayama, K.; The surgical significance of the carotid body in relation to bronchial asthma; Thoracic Surgery; Journal of the International College of Surgeons; 39(4); pp. 374-389; Apr. 1963.
Nespoulet et al.; Altitude illness is related to low hypoxic chemoresponse and low oxygenation during sleep; Eur Respir J; 40(3); pp. 673-680; Sep. 2012 (ERJ Express; epub Apr. 20, 2012).
Nguyen et al.; Carotid body detection on CT angiography; Am J Neuroradiol; 32; pp. 1096-1099; Jun.-Jul. 2011.
O'Donnell et al.; Pathophysiology of dyspnea in chronic obstructive pulmonary disease: a rountable; Proc Am Thorac Soc; 4(2); pp. 145-168; May 2007.
O'Rourke et al.; Removal of the carotid body for asthma: A preliminary report of 40 cases; The Medical Journal of Australia; 2; pp. 1040-1043; Dec. 1963.
O'Rourke et al.; Removal of the carotid body for asthma: An appraisal of results; The Medical Journal of Australia; 2; pp. 869-870; Nov. 1964.
Overholt et al.; Hidden or unsuspected brochiectasis in the asthmatic patient; JAMA; 150(5); pp. 438-441; Oct. 1952.
Overholt, R.; Glomectomy for asthma; Chest; 40; pp. 605-610; Dec. 1961.
Paliwoda et al.; Surgical removal of the carotid body and denervation of the carotid sinus for bronchial asthma; East African Medical Journal; 44(7); pp. 285-287; Jul. 1967.
Paton et al.; The carotid body as a therapeutic target for the treatment of sympathetically mediated diseases; Hypertension; 61; pp. 5-13; Jan. 2013.
Perret et al.; High prevalence of peripheral atherosclerosis in a rapidly developing country; Atherosclerosis; 153(1); pp. 9-21; Nov. 2000.
Phillips et al.; Results of glomectomy in chronic obstructive pulmonary disease: A four year follow-up report of 57 cases; Chest; 58(4); pp. 358-362; Oct. 1970.
Phillips, J.; Removal of the carotid body for asthma and emphysema; Southern Medical Journal; 57; pp. 1278-1281; Nov. 1964.
Phillips, J.; Treatment of obstructive bronchial diseases; Geriatrics; 21 (7); pp. 137-143; Jul. 1966.
Ponikowski et al.; Peripheral chemoreceptor hypersensitivity; Circulation; 101; pp. 544-549; Jul. 2001.
Rabl et al.; Diagnosis and treatment of carotid body tumors; Thorac Cardiovasc Surg.; 41(6); pp. 340-343; Dec. 1993.
Sanghvi et al.; Carotid body tumors; Journal of Surgical Oncology; 54 (3); pp. 190-192; Nov. 1993.
Sedwitz et al.; Should the carotid body be removed in the treatment of asthma and emphysema?; International Surgery; 57(6); pp. 467-469; Jun. 1972.
Sedwitz et al.; Unilateral excision of the carotid body in the treatment of 500 asthma patients; Vascular Diseases; 2; pp. 91-98; Mar. 1965.
Sedwitz, J.; Unilateral carotid body resectin for asthma; Jounal of the National Medical Association; 55(5); pp. 384-388; Sep. 1963.
Segal et al.; Glomectomy in the treatment of chronic bronchial asthma; NEJM; 272(2); pp. 57-63; Jan. 1965.
Segal, M.; Glomectomy for chronic bronchial asthma: A three phase study; Annals of Allergy; 23; pp. 377-384; Aug. 1965.

(56) References Cited

OTHER PUBLICATIONS

Severinghaus, J.; Carotid body resection for COPD?; CHEST; 95(5); pp. 1128-1129; May 1989.
Shalev, Alon; U.S. Appl. No. 61/178,049 entitled "Endovascular systems for performing interventions during ischemic conditions of the CNS by utilizing the carotid baroreceptors and chemoreceptors and methods for using same," filed May 14, 2009.
Shamblin et al.; Carotid Body Tumor; Am J Surg; 122; pp. 732-739; Dec. 1971.
Shek, J.; Excision of carotid body for advanced emphysema; Michigan State Medical Society Journal; 63; pp. 211-212; Mar. 1964.
Silva et al.; Welcome the carotid chemoreflex to the 'neural control of the circulation during exercise' club; J Physiol; 590(Pt 12) ; pp. 2835-2836; Jun. 2012.
Somfay et al.; Dose-response effect of oxygen on hyperinflation and exercise endurance in non-hypoxaemic COPD patients; European Respiratory Journal 18; pp. 77-84; Jul. 2001.
Somfay et al.; Effect of hyperoxia on gas exchange and lactate kinetics following exercise on set in nonhypoxemic COPD patients; Chest; 121(2); pp. 393-400; Feb. 2002.
Stickland et al.; Distribution during exercise in health and chronic heart failure; Circ Res; 100; pp. 1371-1378; May 2007.
Streian et al.; Glomectomy in carotid sinus syncope and associated arrythmias: Symptomatic bradycardia, atrial flutter and atrial fibrillation; Rom J Intern Med; 44(2); pp. 153-163; 2006 (year of pub. sufficiently earlier than effective US filing date and any foreign priority date).
Streian et al.; Glomectomy in carotid sinus syncope; Rev. Roum. Med.—Med. Int.; 26(1); pp. 47-52; Jan.-Mar. 1988.
Syed et al.; Percutaneous superficial temporal artery access for carotid artery stenting in patients with a hostile aortic arch; J Endovasc Ther; 18(5); pp. 729-733; Oct. 2011.
Tamura et al.; A morphometric study of the carotid sinus nerve in patients with diabetes mellitus and chronic alchoholism; Journal of the Autonomic Nervous System; 23; pp. 9-15; Jun. 1988.
Tchibukmacher, N.; Surgical anatomy of carotid sinus nerve and intercarotid ganglion; Surgery, Gynecology and Obstetrics; 67; pp. 740-745; 1938 (year of pub. sufficiently earlier than effective US filing date and any foreign priority date).
Timmers et al.; Denervation of carotid baro- and chemoreceptors in humans; J Physiol; 553(1); pp. 3-11; Nov. 2003.
Toorop et al.; Anatomy of the carotid sinus nerve and surgical implications in carotid sinus syndrome; J Vasc Surg; 50; pp. 177-182; Jul. 2009.
Toorop et al.; Effective surgical treatment of the carotid sinus syndrome; J Cardiovasc Surg.; 50; pp. 683-686; Oct. 2009.
Tubbs et al.; Anatomic landmarks for nerves of the neck: a vade mecum for neurosurgeons; Operative Neurosurgery; 56(ONS Suppl 2); pp. ONS256-ONS260; Apr. 2005.
Van Der Mey et al.; Management of carotid body tumors; Otolaryngol Clin North Am.; 34(5); pp. 907-924; Oct. 2001.
Vermeire et al.; Carotid body resection in patients with severe chronic airflow limitation; Bull Eur Physiopathol Respir; 23 Suppl 11; pp. 165s-166s; Aug. 1987.
Ward et al.; Embolization: An adjunctive measure for removal of carotid body tumors; Laryngoscope; 98; pp. 1287-1291; Dec. 1988.
Wasserman et al.; Effect of carotid body resection on ventilatory and acid-base control during exercise; Journal of Applied Physiology; 39(3); pp. 354-358; Aug. 1975.
Wasserman et al.; Ventilation during exercise in chronic heart failure; Basic Res Cardiol; 91(suppl. 1); pp. 1-11; 1996 (year of pub. sufficiently earlier than effective US filing date and any foreign priority date).
Whipp et al.; Physiologic changes following bilateral carotid-body resection in patients with chronic obstructive pulmonary disease; Chest; 101(3); pp. 656-661; Mar. 1992.
Whipp, B.J.; Carotid bodies and breathing in humans; Thorax; 49(11); pp. 1081-1084; Nov. 1994.
Williams et al.; Carotid body tumor; Arch Surg.; 127; pp. 963-968; Aug. 1992.
Winter et al.; Immediate effects of bilateral carotid body resection on total respiratory resistance and compliance in humans; Adv Exp Med Biol; 551; pp. 15-21; 2005 (year of pub. sufficiently earlier than effective US filing date and any foreign priority date).
Winter, B.; Bilateral carotid body resection for asthma and emphysema; International Surgery; 57(6); pp. 458-466; Jun. 1972.
Winter, B.; Carotid body resection in chronic obstructive pulmonary disease; Chest; 100(3); p. 883; Sep. 1991.
Winter, B.; Carotid body resection: Controversy—confusion—conflict; Ann thorac Surg.; 16(6); pp. 648-659; Dec. 1973.
Wood et al.; Bilateral removal of carotid bodies for asthma; thorax; 20(6); pp. 570-573; Nov. 1965.
Gelfand et al.; U.S. Appl. No. 13/852,895 entitled "Carotid Body Modulation Planning and Assessment," filed Mar. 28, 2013.
Gelfand et al.; U.S. Appl. No. 13/869,765 entitled "Endovascular Catheters and Methods for Carotid Body Ablation," filed Apr. 24, 2013.
Gelfand et al.; U.S. Appl. No. 13/933,023 entitled "Carotid Body Ablation Via Directed Energy," filed Jul. 1, 2013.
Engelman et al.; U.S. Appl. No. 13/936,121 entitled "Devices and Systems for Carotid Body Ablation," filed Jul. 5, 2013.
Leung et al.; U.S. Appl. No. 13/908,995 entitled "Percutaneous Methods and Devices for Carotid Body Ablation," filed Jun. 3, 2013.

\* cited by examiner

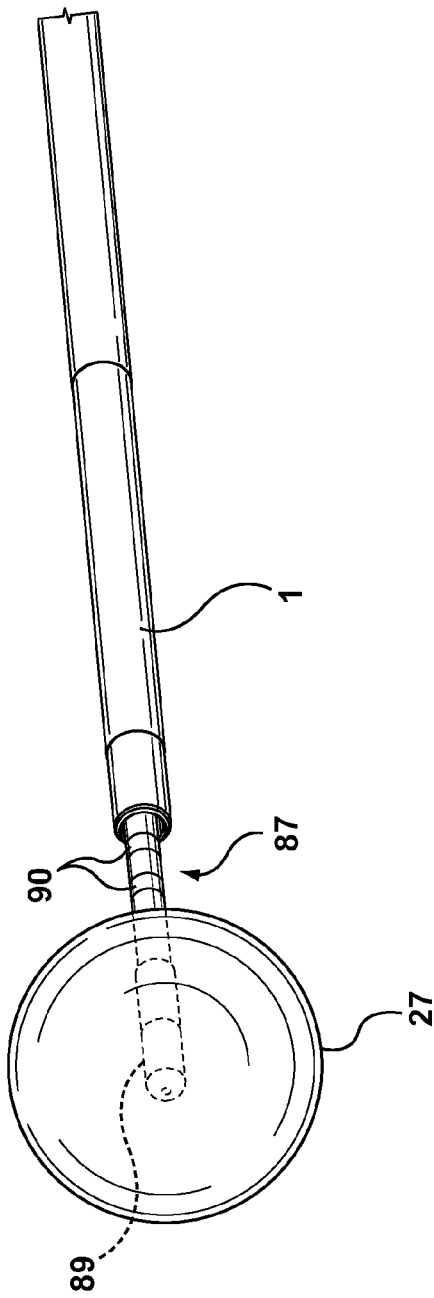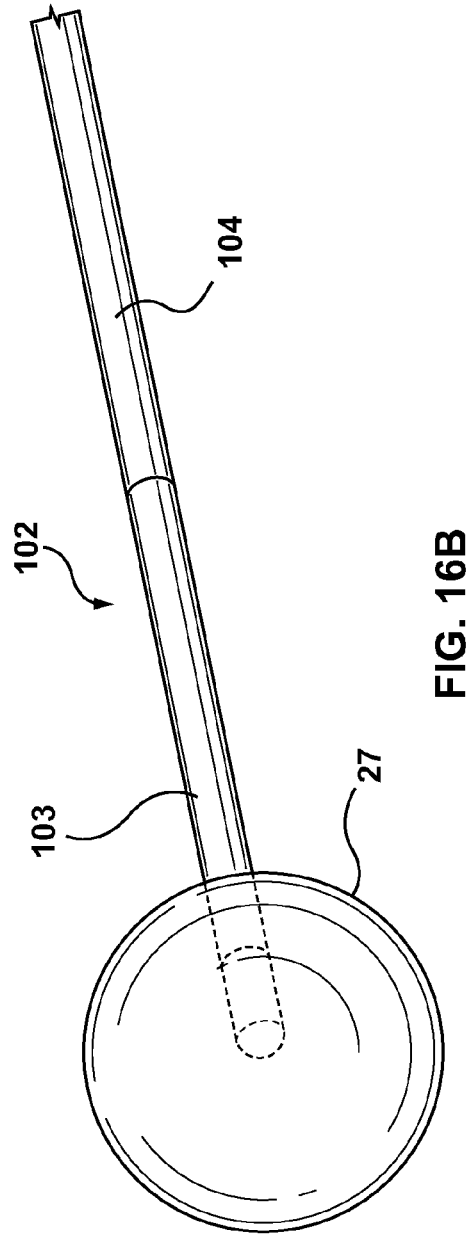
FIG. 16A
FIG. 16B

METHODS AND DEVICES FOR CRYOGENIC CAROTID BODY ABLATION

CROSS REFERENCE TO RELATED APPLICATIONS

This application claims priority to the following applications, the disclosures of which are incorporated by reference herein: U.S. Prov. App. No. 61/654,221, filed Jun. 1, 2012; U.S. Prov. App. No. 61/666,384, filed Jun. 29, 2012; and U.S. Prov. App. No. 61/798,847, filed Mar. 15, 2013.

This application is related to the following applications, the disclosures of which are incorporated by reference herein: U.S. application Ser. No. 13/852,895, filed Mar. 28, 2013; and U.S. application Ser. No. 13/869,765, filed Apr. 24, 2013.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure is directed generally to cryogenic systems and methods for treating patients having sympathetically mediated disease associated at least in part with augmented peripheral chemoreflex or heightened sympathetic activation by ablating at least one peripheral chemoreceptor (e.g., carotid body).

BACKGROUND

It is known that an imbalance of the autonomic nervous system is associated with several disease states. Restoration of autonomic balance has been a target of several medical treatments including modalities such as pharmacological, device-based, and electrical stimulation. For example, beta blockers are a class of drugs used to reduce sympathetic activity to treat cardiac arrhythmias and hypertension; Gelfand and Levin (U.S. Pat. No. 7,162,303) describe a device-based treatment used to decrease renal sympathetic activity to treat heart failure, hypertension, and renal failure; Yun and Yuarn-Bor (U.S. Pat. No. 7,149,574; U.S. Pat. No. 7,363,076; U.S. Pat. No. 7,738,952) describe a method of restoring autonomic balance by increasing parasympathetic activity to treat disease associated with parasympathetic attrition; Kieval, Burns and Serdar (U.S. Pat. No. 8,060,206) describe an electrical pulse generator that stimulates a baroreceptor, increasing parasympathetic activity, in response to high blood pressure; Hlavka and Elliott (US 2010/0070004) describe an implantable electrical stimulator in communication with an afferent neural pathway of a carotid body chemoreceptor to control dyspnea via electrical neuromodulation. More recently, Carotid Body Ablation (CBA) has been conceived for treating sympathetically mediated diseases.

SUMMARY

A method, device, and system have been conceived for cryo-ablation of a carotid body. Cryo-ablation of a carotid body generally refers to delivering a device with a cryo-ablation element in the region of its distal tip through a patient's body proximate to a peripheral chemosensor (e.g., carotid body) or an associated nerve of the patient and then activating the cryo-ablation element to ablate the tissue surrounding the cryo-ablation element resulting in carotid body ablation.

A carotid body may be ablated by placing a cryo-ablation element within and against the wall of a carotid artery adjacent to the carotid body of interest, then activating the cryo-ablation element thereby lowering the temperature of the periarterial space containing the carotid body to an extent and duration sufficient to ablate the carotid body.

A carotid body may also be ablated by placing a cryo-ablation element within and against the wall of an internal jugular vein adjacent to the carotid body of interest, then activating the cryo-ablation element thereby lowering the temperature of the perivenous space containing the carotid body to an extent and duration sufficient to ablate the carotid body.

A carotid body may also be ablated by placing a cryo-ablation element within and against the wall of a branch vein draining into a jugular vein, such as a facial vein, adjacent to the carotid body of interest, then activating the cryo-ablation element thereby lowering the temperature of the perivenous space containing the carotid body to an extent and duration sufficient to ablate the carotid body.

A carotid body may also be ablated by placing a cryo-ablation element within an extravascular space proximate to a carotid body of interest, then activating the cryo-ablation element thereby lowering the temperature of the extravascular space containing the carotid body to an extent and duration sufficient to ablate the carotid body.

In another exemplary procedure a location of periarterial space associated with a carotid body is identified, then a cryo-ablation element is placed against the interior wall of a carotid artery adjacent to the identified location, then cryo-ablation parameters are selected and the cryo-ablation element is activated thereby ablating the carotid body, whereby the position of the cryo-ablation element and the selection of cryo-ablation parameters provides for ablation of the carotid body without substantial collateral damage to adjacent functional structures.

In a further exemplary procedure a location of perivenous space associated with a carotid body is identified, then a cryo-ablation element is placed against the interior wall of an internal jugular vein adjacent to the identified location, then cryo-ablation parameters are selected and the cryo-ablation element is activated thereby ablating the carotid body, whereby the position of the cryo-ablation element and the selection of cryo-ablation parameters provides for ablation of the carotid body without substantial collateral damage to adjacent functional structures.

In a further exemplary procedure a location of extravascular space associated with a carotid body is identified, then a cryo-ablation element is placed proximate to the identified location, then cryo-ablation parameters are selected and the cryo-ablation element is activated thereby ablating the carotid body, whereby the position of the cryo-ablation element and the selection of cryo-ablation parameters provides for ablation of the carotid body without substantial collateral damage to adjacent functional structures.

In further example the location of the periarterial space associated with a carotid body is identified, as well as the location of vital structures not associated with the carotid body, then a cryo-ablation element is placed against the interior wall of a carotid artery adjacent to the identified location, cryo-ablation parameters are selected and the cryo-ablation element is then activated thereby ablating the carotid body, whereby the position of the cryo-ablation element and the selection of cryo-ablation parameters provides for ablation of the target carotid body without substantial collateral damage to vital structures in the vicinity of the carotid body.

In another example the location of the perivenous space associated with a carotid body is identified, as well as the location of vital structures not associated with the carotid body, then a cryo-ablation element is placed against the interior wall of an internal jugular vein, or alternatively a facial vein adjacent to the identified location, cryo-ablation parameters are selected and the cryo-ablation element is then activated thereby ablating the carotid body, whereby the position of the cryo-ablation element and the selection of cryo-ablation parameters provides for ablation of the target carotid body without substantial collateral damage to vital structures in the vicinity of the carotid body.

In another example the location of the extravascular space associated with a carotid body is identified, as well as the location of vital structures not associated with the carotid body, then a cryo-ablation element is placed within or adjacent to the identified location, cryo-ablation parameters are selected and the cryo-ablation element is then activated thereby ablating the carotid body, whereby the position of the cryo-ablation element and the selection of cryo-ablation parameters provides for ablation of the target carotid body without substantial collateral damage to vital structures in the vicinity of the carotid body.

In another example the location of the extravascular space associated with a carotid body is identified, as well as the location of vital structures not associated with the carotid body, then a cryo-ablation element and an associated warming element is placed within or adjacent to the identified location, cryo-ablation and warming parameters are selected and the cryo-ablation element and warming element are then activated thereby cryo-ablating the carotid body while protecting vital neural structures, by the position of the cryo-ablation element and the selection of cryo-ablation parameters in addition to the protective warming provides for ablation of the target carotid body without substantial collateral damage to vital structures in the vicinity of the carotid body.

In another example the location of the extravascular space associated with a carotid body is identified, as well as the location of vital structures not associated with the carotid body, then a cryo-ablation element is placed within or adjacent to the identified location, an extracorporeal high frequency focused ultrasound (HIFU) transducer is focused on the location of vital structures not associated with the carotid body that are proximate the identified location, cryo-ablation and HIFU parameters are selected and the cryo-ablation element and HIFU transducer are then activated thereby cryo-ablating the carotid body while protecting vital neural structures via selective warming with HIFU; by the position of the cryo-ablation element and the selection of cryo-ablation parameters in addition to the protective warming provides for ablation of the target carotid body without substantial collateral damage to vital structures in the vicinity of the carotid body.

Selectable carotid body cryo-ablation parameters include cryo-ablation element temperature, duration of cryo-ablation element activation, cryo-ablation element force of contact with a vessel wall, cryo-ablation element size, cryo-ablation modality (reversible or not reversible), number of cryo-ablation element activations, and cryo-ablation element position within a patient.

The location of the perivascular space associated with a carotid body is determined by means of a non-fluoroscopic imaging procedure prior to carotid body cryo-ablation, where the non-fluoroscopic location information is translated to a coordinate system based on fluoroscopically identifiable anatomical and/or artificial landmarks.

A function of a carotid body is stimulated and at least one physiological parameter is recorded prior to and during the stimulation, then the carotid body is cryo-ablated, and the stimulation is repeated, whereby the change in recorded physiological parameter(s) prior to and after cryo-ablation is an indication of the effectiveness of the cryo-ablation.

A function of a carotid body is blocked and at least one physiological parameter(s) is recorded prior to and during the blockade, then the carotid body is cryo-ablated, and the blockade is repeated, whereby the change in recorded physiological parameter(s) prior to and after cryo-ablation is an indication of the effectiveness of the cryo-ablation.

A device configured to prevent embolic debris from entering the brain is deployed in an internal carotid artery associated with a carotid body, then a cryo-ablation element is placed proximate with the carotid body, the cryo-ablation element is activated resulting in carotid body ablation, the cryo-ablation element is then withdrawn from the proximate location, then the embolic prevention device is withdrawn from the internal carotid artery, whereby the device in the internal carotid artery prevents debris resulting from the use of the cryo-ablation element from entering the brain.

A method has been conceived in which the location of the perivascular space associated with a carotid body is identified, then a cryo-ablation element is placed in a predetermined location against the interior wall of vessel adjacent to the identified location, then cryo-ablation parameters are selected and the cryo-ablation element is activated and then deactivated, the cryo-ablation element is then repositioned in at least one additional predetermined location against the same interior wall and the cryo-ablation element is then reactivated using the same or different cryo-ablation parameters, whereby the positions of the cryo-ablation element and the selection of cryo-ablation parameters provides for ablation of the carotid body without substantial collateral damage to adjacent functional structures.

A method has been conceived in which the location of the extravascular space associated with a carotid body is identified, then a cryo-ablation element is placed within the extravascular location or adjacent to the extravascular location, then cryo-ablation parameters are selected and the cryo-ablation element is activated and then deactivated, the cryo-ablation element is then repositioned in at least one additional location and the cryo-ablation element is then reactivated using the same or different cryo-ablation parameters, whereby the positions of the cryo-ablation element and the selection of cryo-ablation parameters provides for ablation of the carotid body without substantial collateral damage to adjacent functional structures.

A method has been conceived by which the location of the perivascular space associated with a carotid body is identified, then a cryo-ablation element configured for tissue freezing is placed against the interior wall of a vessel adjacent to the identified location, then cryo-ablation parameters are selected for reversible cryo-ablation and the cryo-ablation element is activated, the effectiveness of the ablation is then determined by at least one physiological response to the ablation, and if the determination is that the physiological response is favorable, then the cryo-ablation element is reactivated using the cryo-ablation parameters selected for permanent carotid body ablation.

A method has been conceived by which the location of the extravascular space associated with a carotid body is identified, then a cryo-ablation element configured for tissue freezing is placed into or adjacent to the identified location, an ultrasonic imaging device configured for imaging a boundary between frozen tissue and not frozen tissue in the located extravascular space is positioned for said imaging, cryo-ablation parameters are selected and the cryo-ablation element is activated while the tissue freezing is monitored by the ultrasonic imaging device, and the cryo-ablation is deactivated when the boundary between frozen tissue and not frozen tissue approaches a predetermined boarder for cryo-ablation.

A system has been conceived comprising a vascular catheter configured with a cryo-ablation element in the vicinity of the distal end, and a connection between the cryo-ablation element and a source of cryo-ablation fluid at the proximal end, whereby the distal end of the catheter is constructed to be inserted into a peripheral artery of a patient and then maneuvered into an internal or external carotid artery using standard fluoroscopic guidance techniques.

A system has been conceived comprising a catheter configured with a cryo-ablation element in the vicinity of the distal end, and a means to connect the ablation element to a source of cryo-ablation fluid at the proximal end, whereby the distal end of the catheter is constructed to be inserted into a peripheral vein of a patient and then maneuvered into an internal jugular vein, or alternately a facial vein using standard fluoroscopic guidance techniques.

A system has been conceived comprising a vascular catheter configured with a cryo-ablation element in the vicinity of the distal end configured for carotid body cryo-ablation and further configured for at least one of the following: neural stimulation, neural blockade, carotid body stimulation and carotid body blockade; and a connection between the cryo-ablation element and a source of cryo-ablation fluid, and stimulation energy and/or blockade energy.

A system has been conceived comprising a vascular catheter configured with a cryo-ablation element and at least one electrode configured for at least one of the following: neural stimulation, neural blockade, carotid body stimulation and carotid body blockade; and a connection between the cryo-ablation element to a source of cryo-ablation fluid, and a connection between the cryo-ablation element and/or electrode(s) to a source of stimulation energy and/or blockade energy.

A system has been conceived comprising a vascular catheter with an ablation element mounted in the vicinity of the distal end configured for tissue freezing, whereby, the ablation element comprises at least one cryogenic expansion chamber and at least one temperature sensor, and a connection between the ablation element expansion chamber and temperature sensor(s) to a cryogenic agent source, with the cryogenic agent source being configured to maintain the ablation element at a predetermined temperature in the range of 0 to −180 degrees centigrade during ablation using signals received from the temperature sensor(s). System contains computer logic that controls delivery of cryogen in order to maintain set temperature. Specifically temperature can be more than one setting: (a) low cold setting in order to test response of nerves, (b) high cold setting in order to cause ablation with consequential destruction of tissue by necrosis and apoptosis of living cells.

A system has been conceived comprising a probe configured for percutaneous access to the extravascular space including a carotid body with a cryo-ablation element mounted in the vicinity of the distal end configured for tissue freezing, whereby, the cryo-ablation element comprises at least one cryogenic chamber and at least one temperature sensor, and a connection between the cryogenic chamber and temperature sensor(s) to a cryogenic fluid source, with the cryogenic fluid source being configured to maintain the cryo-ablation element at a predetermined temperature in the range of 0 to −180 degrees centigrade during ablation using signals received from the temperature sensor(s).

A system has been conceived comprising a vascular catheter with an ablation element mounted in the vicinity of the distal end configured to freeze tissue, and to heat tissue, whereby, the ablation element comprises at least one cryogenic chamber constructed of an electrically conductive material and configured as an electrode, and at least one temperature sensor, and a connection between the ablation element cryogenic chamber/electrode and temperature sensor(s) to an ablation source consisting of cryogenic fluid source and an electrical heating energy source.

A system has been conceived comprising a probe configured for percutaneous access to an extravascular space including a carotid body with an ablation element mounted in the vicinity of the distal end configured to freeze tissue, and to heat tissue, whereby, the ablation element comprises at least one cryogenic chamber constructed of an electrically conductive material and configured as an electrode, and at least one temperature sensor, and a connection between the ablation element cryogenic chamber/electrode and temperature sensor(s) to an ablation source consisting of cryogenic fluid source and an electrical heating energy source.

A vascular cryo-ablation catheter has been conceived with a user deflectable segment in the vicinity of the distal end and a non-deflectable segment proximal to the deflectable segment, where the deflection of the distal segment is facilitated by a pull wire within the catheter in communication between the distal segment and a handle containing a deflection actuator at the proximal end, and a cryo-ablation element mounted in the vicinity of the distal end, whereby the deflection mechanism is configured to provide the user with a means for placing the cryo-ablation element against the wall of a vessel adjacent to a carotid body.

In accordance with another aspect of this invention is a vascular catheter with a structure configured for user actuated radial expansion in the vicinity of the distal end, a radiopaque cryo-ablation element mounted on one side of the structure and at least one radiopaque element mounted on the opposite side of the structure, whereby the structure provides the user with a means for pressing the cryo-ablation element against the wall of a vessel, and the combination of the radiopaque cryo-ablation element and the radiopaque element provide the user with a substantially unambiguous fluoroscopic determination of the location of the cryo-ablation element within the vessel.

A system for endovascular transmural cryo-ablation of a carotid body has been conceived comprising an endovascular catheter with a cryo-ablation element mounted in the vicinity of the distal end, a means for pressing the cryo-ablation element against the wall of a carotid artery at a specific location, a means for providing the user with a substantially unambiguous fluoroscopic determination of the position of the ablation element in a carotid artery, a means for connecting the cryo-ablation element to a source of cryogenic fluid mounted in the vicinity of the proximal end, and a console comprising a source of cryogenic fluid, a means for controlling the cryogenic fluid, a user interface configured to provide the user with a selection of cryo-ablation parameters, indications of the status of the console and the status of the cryo-ablation activity, a means to activate and deactivate a cryo-ablation, and an umbilical to provide a means for connecting the catheter to the console.

A method has been conceived to reduce or inhibit chemoreflex function generated by a carotid body in a mammalian patient, to reduce afferent nerve sympathetic activity of carotid body nerves to treat a sympathetically mediated disease, the method comprising: positioning a catheter in a vascular system of the patient such that a distal section of the catheter is in a lumen proximate to the carotid body of the patient; pressing a cryo-ablation element against the wall of the lumen adjacent to the carotid body, supplying cryogenic fluid to the cryo-ablation element wherein the fluid is supplied by a fluid supply apparatus outside of the patient; applying the fluid from the fluid supply to the cryo-ablation element to ablate tissue proximate to or included in the carotid body; and removing the cryo-ablation device from the patient; wherein a carotid body chemoreflex function is inhibited or sympathetic afferent nerve activity of carotid body nerves is reduced due to the ablation.

A method has been conceived to treat a patient having a sympathetically mediated disease by reducing or inhibiting chemoreflex function generated by a carotid body including steps of inserting a catheter into the patient's vasculature, positioning a portion of the catheter proximate a carotid body (e.g., in a carotid artery), positioning a cryo-ablation element toward a target ablation site (e.g., carotid body, intercarotid septum, carotid plexus, carotid sinus nerve), holding position of the catheter, applying cryogenic fluid to the cryo-ablation element, and removing the catheter from the patient's vasculature.

The methods and systems disclosed herein may be applied to satisfy clinical needs related to treating cardiac, metabolic, and pulmonary diseases associated, at least in part, with enhanced chemoreflex (e.g., high chemosensor sensitivity or high chemosensor activity) and related sympathetic activation. The treatments disclosed herein may be used to restore autonomic balance by reducing sympathetic activity, as opposed to increasing parasympathetic activity. It is understood that parasympathetic activity can increase as a result of the reduction of sympathetic activity (e.g., sympathetic withdrawal) and normalization of autonomic balance. Furthermore, the treatments may be used to reduce sympathetic activity by modulating a peripheral chemoreflex. Furthermore, the treatments may be used to reduce afferent neural stimulus, conducted via afferent carotid body nerves, from a carotid body to the central nervous system. Enhanced peripheral and central chemoreflex is implicated in several pathologies including hypertension, cardiac tachyarrhythmias, sleep apnea, dyspnea, chronic obstructive pulmonary disease (COPD), diabetes and insulin resistance, and CHF. Mechanisms by which these diseases progress may be different, but they can commonly include contribution from increased afferent neural signals from a carotid body. Central sympathetic nervous system activation is common to all these progressive and debilitating diseases. Peripheral chemoreflex may be modulated, for example, by modulating carotid body activity. The carotid body is the sensing element of the afferent limb of the peripheral chemoreflex. Carotid body activity may be modulated, for example, by cryo-ablating a carotid body or afferent nerves emerging from the carotid body. Such nerves can be found in a carotid body itself, in a carotid plexus, in an intercarotid septum, in periarterial space of a carotid bifurcation and internal and external carotid arteries, and internal jugular vein, or facial vein. Therefore, a therapeutic method has been conceived that comprises a goal of restoring or partially restoring autonomic balance by reducing or removing carotid body input into the central nervous system.

BRIEF DESCRIPTION OF THE DRAWINGS

FIG. 16A is a schematic view of an endovascular ablation catheter having a point-ablate cryogenic ablation element, contained in a steerable sheath, showing an ice ball formed around the cryogenic ablation element.

FIG. 16B is a schematic view of a steerable endovascular ablation catheter having a point-ablate cryogenic ablation element showing an ice ball formed around the cryogenic ablation element.

DETAILED DESCRIPTION

Figure 1:
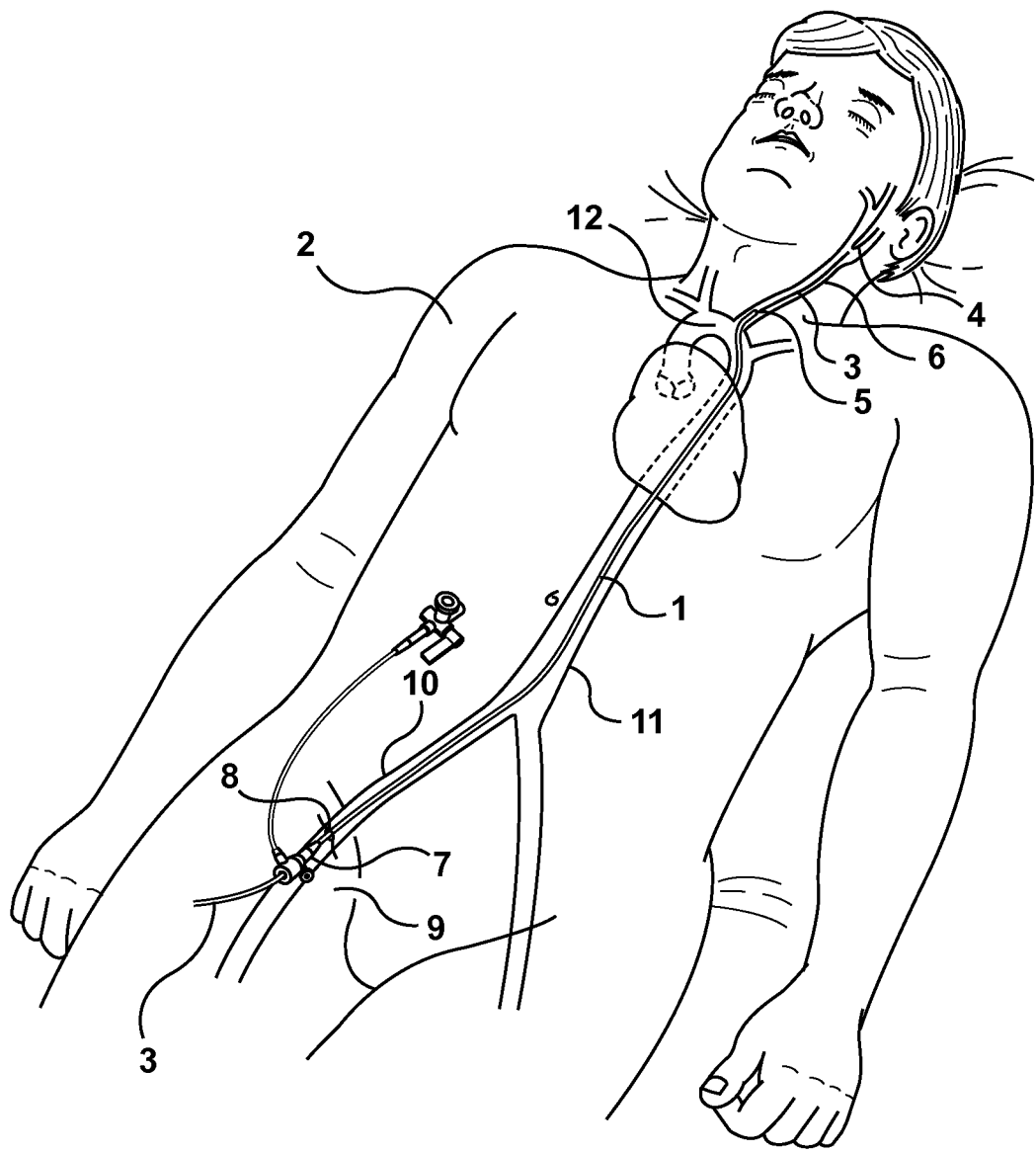
FIG. 1 is an illustration showing endovascular access of a catheter to a left common carotid artery of a patient lying in supine position.

Cryogenic systems, devices, and methods have been conceived to ablate fully or partially one or both carotid bodies or peripheral chemoreceptors to treat patients having a sympathetically mediated disease (e.g., cardiac, renal, metabolic, or pulmonary disease such as hypertension, CHF, or sleep apnea, sleep disordered breathing, diabetes or insulin resistance) at least partially resulting from augmented peripheral chemoreflex (e.g., peripheral chemoreceptor hypersensitivity) or heightened sympathetic activation. A reduction of peripheral chemoreflex (e.g., chemosensitivity or afferent nerve hyperactivity) or reduction of afferent nerve signaling from a carotid body (CB) resulting in a reduction of central sympathetic tone is a main therapy pathway. Higher than normal chronic or intermittent activity of afferent carotid body nerves is considered enhanced chemoreflex for the purpose of this application regardless of its cause. Other important benefits such as increase of parasympathetic tone, vagal tone and specifically baroreflex and baroreceptor activity reduction of dyspnea, hyperventilation and breathing rate may be expected in some patients. Secondary to reduction of breathing rate additional increase of parasympathetic tone can be expected in some cases. Augmented peripheral chemoreflex (e.g., carotid body activation) leads to increases in sympathetic nervous system activity, which is in turn primarily responsible for the progression of chronic disease as well as debilitating symptoms and adverse events seen in our intended patient populations. The patients are mammalian patients, including humans. Carotid bodies contain cells that are sensitive to oxygen and carbon dioxide. Carotid bodies also respond to blood flow, pH acidity, glucose level in blood and possibly other variables. Thus carotid body ablation may be a treatment for patients, for example having heart disease or diabetes, even if chemosensitive cells are not activated.

An inventive treatment, cryogenic carotid body ablation, may involve inserting a cryo-ablation device in to a patient, positioning a distal region of the cryo-ablation device proximate a carotid body (e.g., in a common carotid artery, internal carotid artery, external carotid artery, at a carotid bifurcation, proximate or in an intercarotid septum, in an internal jugular vein), positioning an ablation element proximate to a target site (e.g., a carotid body, an afferent nerve associated with a carotid body, a peripheral chemosensor, an intercarotid septum), optionally delivering non-ablative cryogenic energy from the ablation element to temporarily block the target site, and delivering ablative cryogenic energy from the ablation element to ablate the target site. Other methods and devices for chemoreceptor ablation are described.

Targets:

To inhibit or suppress a peripheral chemoreflex, anatomical targets for cryo-ablation (also referred to as targeted tissue, target ablation sites, or target sites) may include at least a portion of at least one carotid body, an aortic body, nerves associated with a peripheral chemoreceptor (e.g., carotid body nerves, carotid sinus nerve, carotid plexus), small blood vessels feeding a peripheral chemoreceptor, carotid body parenchyma, chemosensitive cells (e.g., glomus cells), tissue in a location where a carotid body is suspected to reside (e.g., a location based on pre-operative imaging or anatomical likelihood), an intercarotid septum, a substantial part of an intercarotid septum or a combination thereof. As used herein, ablation of a carotid body may refer to ablation of any of these target ablation sites.

Figure 3A:
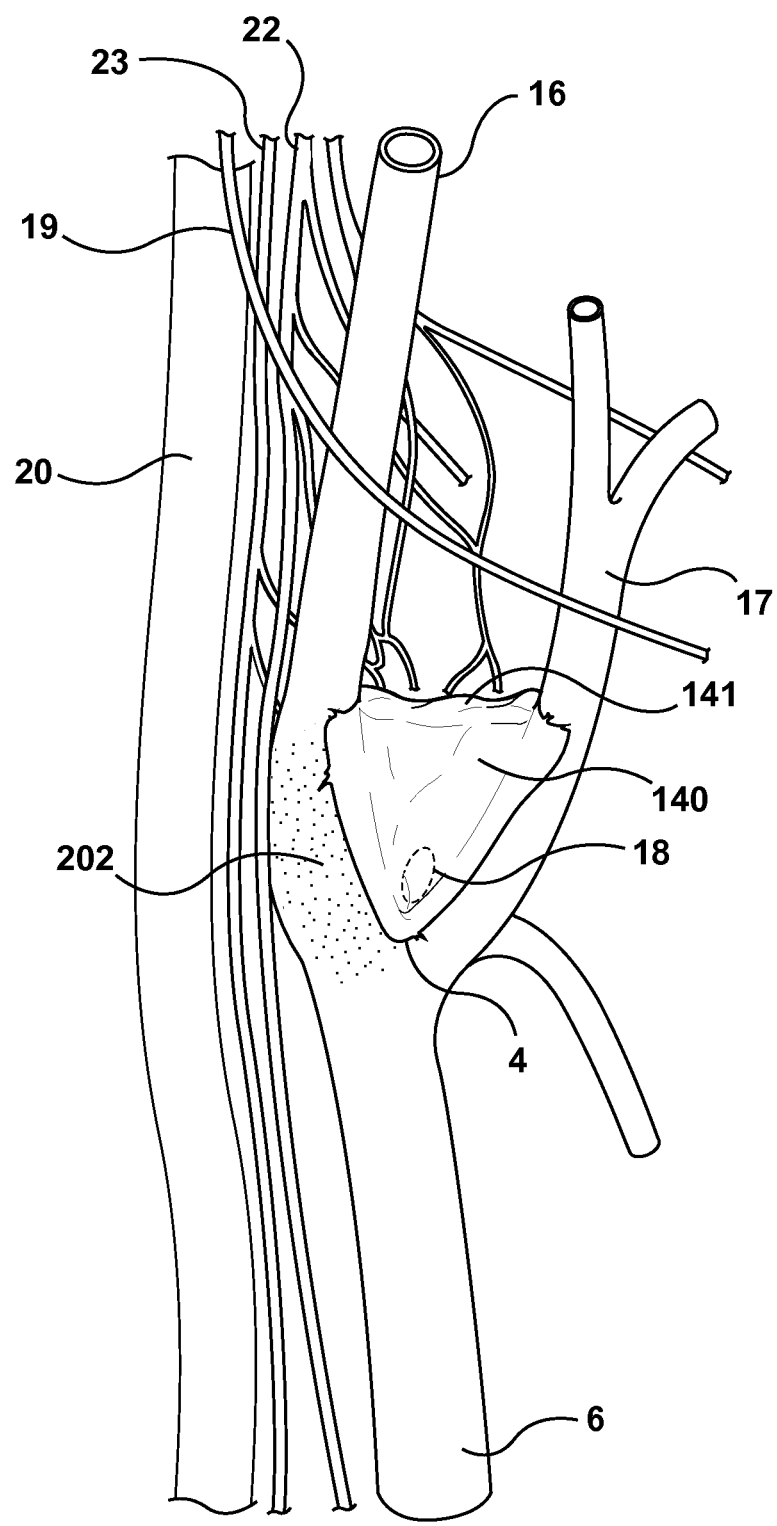
FIG. 3A is an illustration of a target region for carotid body cryo-ablation showing the carotid body associated with an intercarotid septum of a carotid bifurcation.
Figure 3B:
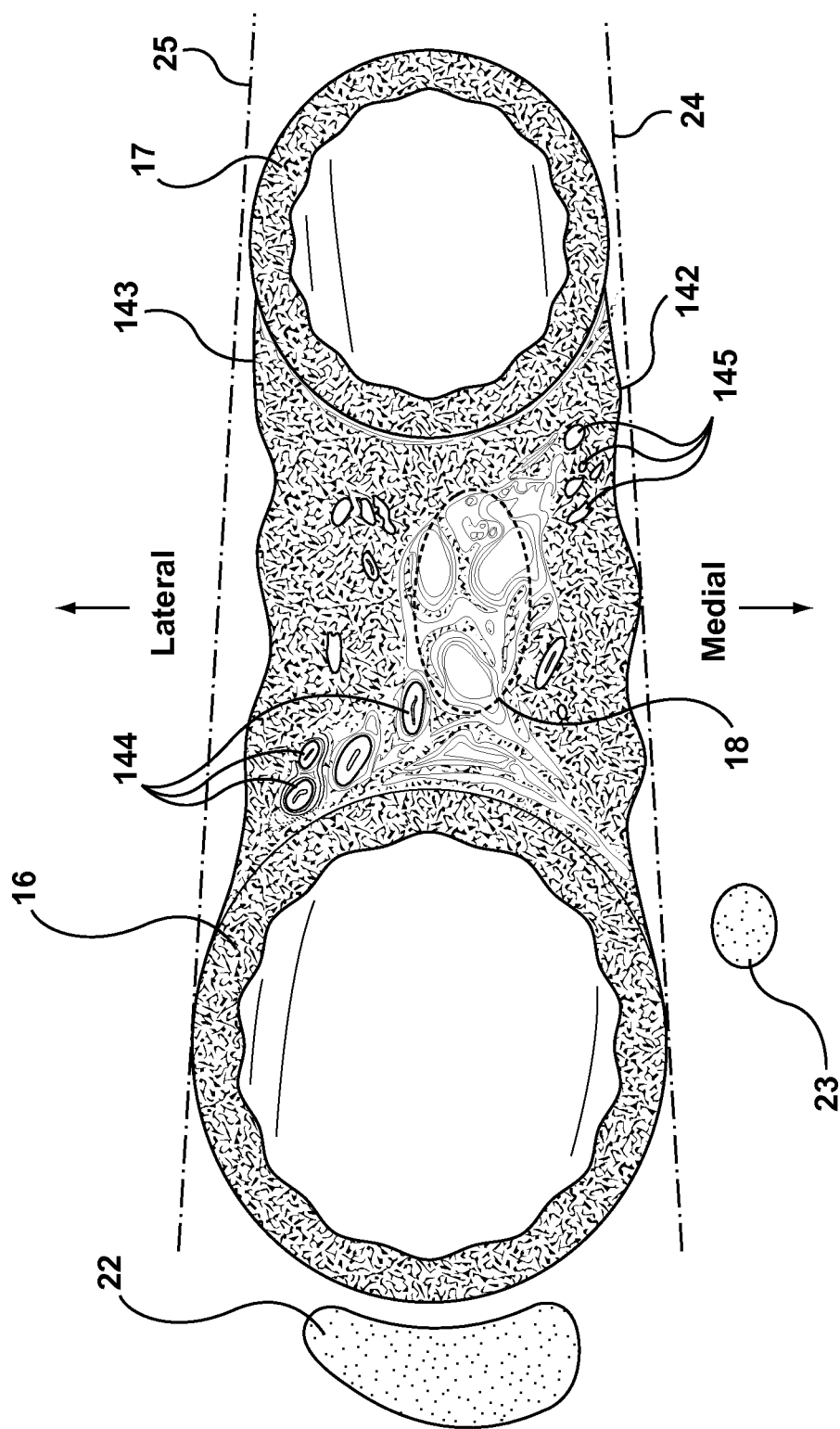
FIG. 3B is an illustration of a cross section of an intercarotid septum.

An intercarotid septum 140 (also referred to as carotid septum) shown in FIGS. 3A and 3B is herein defined as a wedge or triangular segment of tissue with the following boundaries: A saddle of a carotid bifurcation 4 defines a caudal aspect (an apex) of a carotid septum 140; Facing walls of internal 16 and external 17 carotid arteries define two sides of a carotid septum; A cranial boundary 141 of a carotid septum extends between these arteries and may be defined as cranial to a carotid body but caudal to any vital nerve structures (e.g., hypoglossal nerve) that might be in the region, for example a cranial boundary may be about 10 mm (possibly 15 mm) from the saddle of the carotid bifurcation 4; Medial 142 and lateral 143 walls of the carotid septum 140 are generally defined by planes approximately tangent to the internal and external carotid arteries; One of the planes 25 is tangent to the lateral wall of the internal and external carotid arteries and the other plane 24 is tangent to the medial walls of these arteries. An intercarotid septum is between medial and lateral walls. An intercarotid septum 140 may contain a carotid body 18 and may be absent of vital structures such as a vagus nerve 22 or vital sympathetic nerves 23 or a hypoglossal nerve 19. An intercarotid septum may include some baroreceptors 202 or baroreceptor nerves. An intercarotid septum may also include various nerves of intercarotid plexus, small blood vessels 144 and fat 145.

Carotid body nerves are anatomically defined herein as carotid plexus nerves and carotid sinus nerves. Carotid body nerves are functionally defined herein as nerves that conduct information from a carotid body to a central nervous system.

A cryo-ablation may be focused exclusively on targeted tissue, or be focused on the targeted tissue while safely ablating tissue proximate to the targeted tissue (e.g., to ensure the targeted tissue is ablated or as an approach to gain access to the targeted tissue). An ablation may be as big as the peripheral chemoreceptor (e.g., carotid body or aortic body) itself, somewhat smaller, or bigger and can include tissue surrounding the chemoreceptor such as blood vessels, adventitia, fascia, small blood vessels perfusing the chemoreceptor, or nerves connected to and innervating the glomus cells. An Intercarotid plexus or carotid sinus nerve may be a target of ablation with an understanding that some baroreceptor nerves will be ablated together with carotid body nerves. Baroreceptors are distributed in the human arteries and have high degree of redundancy.

Tissue may be ablated to inhibit or suppress a chemoreflex of only one of a patient's two carotid bodies. Another embodiment involves ablating tissue to inhibit or suppress a chemoreflex of both of a patient's carotid bodies. For example a therapeutic method may include ablation of one carotid body, measurement of resulting chemosensitivity, sympathetic activity, respiration or other parameter related to carotid body hyperactivity and ablation of the second carotid body if needed to further reduce chemosensitivity following unilateral ablation.

An embodiment of a therapy may substantially reduce chemoreflex without excessively reducing the baroreflex of the patient. The proposed ablation procedure may be targeted to substantially spare the carotid sinus, baroreceptors distributed in the walls of carotid arteries (specifically internal carotid artery), and at least some of the carotid sinus nerves that conduct signals from said baroreceptors. For example, the baroreflex may be substantially spared by targeting a limited volume of ablated tissue possibly enclosing the carotid body, tissues containing a substantial number of carotid body nerves, tissues located in periadventitial space of a medial segment of a carotid bifurcation, or tissue located at the attachment of a carotid body to an artery. Said targeted ablation is enabled by visualization of the area or carotid body itself, for example by CT, CT angiography, MRI, ultrasound sonography, fluoroscopy, blood flow visualization, or injection of contrast, and positioning of an instrument in the carotid body or in close proximity while avoiding excessive damage (e.g., perforation, stenosis, thrombosis) to carotid arteries, baroreceptors, carotid sinus nerves or other vital nerves such as vagus nerve or sympathetic nerves located primarily outside of the carotid septum. Thus imaging a carotid body before ablation may be instrumental in (a) selecting candidates if a carotid body is present, large enough and identified and (b) guiding therapy by providing a landmark map for an operator to guide an ablation instrument to the carotid septum, center of the carotid septum, carotid body nerves, the area of a blood vessel proximate to a carotid body, or to an area where carotid body itself or carotid body nerves may be anticipated. It may also help exclude patients in whom the carotid body is located substantially outside of the carotid septum in a position close to a vagus nerve, hypoglossal nerve, jugular vein or some other structure that can be endangered by ablation. In one embodiment only patients with carotid body substantially located within the intercarotid septum are selected for ablation therapy.

Once a carotid body is ablated, removed or denervated, the carotid body function (e.g., carotid body chemoreflex) does not substantially return in humans (in humans aortic chemoreceptors are considered undeveloped). To the contrary, once a carotid sinus baroreflex is removed it is generally compensated, after weeks or months, by the aortic or other arterial baroreceptor baroreflex. Thus, if both the carotid chemoreflex and baroreflex are removed or substantially reduced, for example by interruption of the carotid sinus nerve or intercarotid plexus nerves, baroreflex may eventually be restored while the chemoreflex may not. The consequences of temporary removal or reduction of the baroreflex can be in some cases relatively severe and require hospitalization and management with drugs, but they generally are not life threatening, terminal or permanent. Thus, it is understood that while selective removal of carotid body chemoreflex with baroreflex preservation may be desired, it may not be absolutely necessary in some cases.

Cryo-Ablation:

The term "cryo-ablation" may refer to the act of altering a tissue to suppress or inhibit its biological function or ability to respond to stimulation permanently or for an extended period of time (e.g., greater than 3 weeks, greater than 6 months, greater than a year, for several years, or for the remainder of the patient's life) by removing heat energy from tissue. Selective denervation may involve, for example, interruption of afferent nerves from a carotid body while substantially preserving nerves from a carotid sinus, which conduct baroreceptor signals. Another example of selective denervation may involve interruption of a carotid sinus nerve, or intercarotid plexus which is in communication with both a carotid body and some baroreceptors wherein chemoreflex from the carotid body is reduced permanently or for an extended period of time (e.g., years) and baroreflex is substantially restored in a short period of time (e.g., days or weeks). As used herein, the term "ablate" refers to interventions that suppress or inhibit natural chemoreceptor or afferent nerves functioning, which is in contrast to neuromodulating or reversibly deactivating and reactivating chemoreceptor functioning.

Cryogenic Carotid Body Ablation (CBA) herein refers to cryo-ablation of a target tissue wherein the desired effect is to reduce or remove the afferent neural signaling from a chemosensor (e.g., carotid body) or reducing a chemoreflex. Chemoreflex or afferent nerve activity cannot be directly measured in a practical way, thus indexes of chemoreflex such as chemosensitivity can sometimes be uses instead. Chemoreflex reduction is generally indicated by a reduction of an increase of ventilation and ventilation effort per unit of blood gas concentration, saturation or partial pressure change or by a reduction of central sympathetic nerve activity that can be measured indirectly. Sympathetic nerve activity can be assessed by measuring activity of peripheral nerves leading to muscles (MSNA), heart rate (HR), heart rate variability (HRV), production of hormones such as renin, epinephrine and angiotensin, and peripheral vascular resistance. All these parameters are measurable and can lead directly to the health improvements. In the case of CHF patients, blood pH, blood $PCO_2$, degree of hyperventilation and metabolic exercise test parameters such as peak $VO_2$, and $VE/VCO_2$ slope are also important. It is believed that patients with heightened chemoreflex have low $VO_2$ and high $VE/VCO_2$ slope (index of respiratory efficiency) as a result of, for example, tachypnea and low blood $CO_2$. These parameters are also related to exercise limitations that further speed up patient's status deterioration towards morbidity and death. It is understood that all these indexes are indirect and imperfect and intended to direct therapy to patients that are most likely to benefit or to acquire an indication of technical success of ablation rather than to prove an exact measurement of effect or guarantee a success. It has been observed that some tachyarrhythmias in cardiac patients are sympathetically mediated. Thus carotid body ablation may be instrumental in treating reversible atrial fibrillation and ventricular tachycardia.

Carotid body ablation may at least in part be due to alteration of vascular or peri-vascular structures (e.g., arteries, arterioles, capillaries or veins), which perfuse the carotid body and neural fibers surrounding and innervating the carotid body (e.g., nerves that transmit afferent information from carotid body chemoreceptors to the brain). Additionally or alternatively ablation may include tissue disruption due to a healing process, fibrosis, or scarring of tissue following cryogenic injury, particularly when prevention of regrowth and regeneration of active tissue is desired. Cryo-ablation may include reducing the temperature of target neural fibers below a desired threshold (e.g., to achieve freezing thermal injury). It is generally accepted that temperatures below $-40°$ C. applied over a minute or two results in irreversible necrosis of tissue and scar formation. It is recognized that tissue ablation by cold involves mechanisms of necrosis and apoptosis. At a low cooling rate freeze, tissue is destroyed by cellular dehydration and at high cooling rate freeze by intracellular ice formation and lethal rupture of plasma membrane.

The mechanisms of cryotherapeutic tissue damage include, for example, direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion).

In some embodiments, cryo-ablation of carotid body or carotid body nerves may be achieved via direct application of thermal cooling to target tissue. For example, a cryogenic element may be applied at least proximate to the target, or cryogenic elements (e.g., cryogenic point-ablate tip, balloon, probe, cryo-tube) can be placed in a vicinity of a chemosensor (e.g., carotid body). Additional and alternative methods and apparatuses may be utilized to achieve cryogenically induced ablation, as described hereinafter.

The devices described herein may also be used to temporarily stun or block nerve conduction by cooling to non-ablative temperatures or at non-ablative cooling rates. A temporary nerve block may be used to confirm position of a cryo-ablation element prior to cryo-ablation. For example, a temporary nerve block may block nerves associated with a carotid body, which may result in a physiological effect to confirm the position may be effective for cryo-ablation. Furthermore, a temporary nerve block may block vital nerves such as vagal, hypoglossal or sympathetic nerves that are preferably avoided, resulting in a physiological effect (e.g., physiological effects may be noted by observing the patient's eyes, tongue, throat or facial muscles or by monitoring patient's heart rate and respiration). This may alert a user that the position is not in a safe location. Likewise absence of a physiological effect indicating a temporary nerve block of such vital nerves in combination with a physiological effect indicating a temporary nerve block of carotid body nerves may indicate that the position is in a safe and effective location for carotid body ablation.

Cryo-ablation is a function of time as well as temperature. Thus cryogenic cooling can be applied to the ablation target site (e.g., carotid body, carotid body nerves or carotid septum) and neural effects may be observed. If undesired neural effects are observed immediately after cooling, cryo-ablation can be interrupted while the process of ablation is still in the reversible phase. If only desired effects are observed, cooling can continue maintaining low temperature for a duration long enough to ensure irreversible cryo-ablation of affected tissues.

Important nerves may be located in proximity of the target site and may be inadvertently and unintentionally injured. Non-ablative cooling can help identify that these nerves are in the ablation zone before the irreversible ablation occurs. These nerves may include the following:

Vagus Nerve Bundle—The vagus is a bundle of nerves that carry separate functions, for example a) branchial motor neurons (efferent special visceral) which are responsible for swallowing and phonation and are distributed to pharyngeal branches, superior and inferior laryngeal nerves; b) visceral motor (efferent general visceral) which are responsible for involuntary muscle and gland control and are distributed to cardiac, pulmonary, esophageal, gastric, celiac plexuses, and muscles, and glands of the digestive tract; c) visceral sensory (afferent general visceral) which are responsible for visceral sensibility and are distributed to cervical, thoracic, abdominal fibers, and carotid and aortic bodies; d) visceral sensory (afferent special visceral) which are responsible for taste and are distributed to epiglottis and taste buds; e) general sensory (afferent general somatic) which are responsible for cutaneous sensibility and are distributed to auricular branch to external ear, meatus, and tympanic membrane. Dysfunction of the vagus may be detected by a) vocal changes caused by nerve damage (damage to the vagus nerve can result in trouble with moving the tongue while speaking, or hoarseness of the voice if the branch leading to the larynx is damaged); b) dysphagia due to nerve damage (the vagus nerve controls many muscles in the palate and tongue which, if damaged, can cause difficulty with swallowing); c) changes in gag reflex (the gag reflex is controlled by the vagus nerve and damage may cause this reflex to be lost, which can increase the risk of choking on saliva or food); d) hearing loss due to nerve damage (hearing loss may result from damage to the branch of the vagus nerve that innervates the concha of the ear): e) cardiovascular problems due to nerve damage (damage to the vagus nerve can cause cardiovascular side effects including irregular heartbeat and arrhythmia); or f) digestive problems due to nerve damage (damage to the vagus nerve may cause problems with contractions of the stomach and intestines, which can lead to constipation).

Superior Laryngeal Nerve—the superior laryngeal nerve is a branch of the vagus nerve bundle. Functionally, the superior laryngeal nerve function can be divided into sensory and motor components. The sensory function provides a variety of afferent signals from the supraglottic larynx. Motor function involves motor supply to the ipsilateral cricothyroid muscle. Contraction of the cricothyroid muscle tilts the cricoid lamina backward at the cricothyroid joint causing lengthening, tensing and adduction of vocal folds causing an increase in the pitch of the voice generated. Dysfunction of the superior laryngeal nerve may change the pitch of the voice and causes an inability to make explosive sounds. A bilateral palsy presents as a tiring and hoarse voice.

Cervical Sympathetic Nerve—The cervical sympathetic nerve provides efferent fibers to the internal carotid nerve, external carotid nerve, and superior cervical cardiac nerve. It provides sympathetic innervation of the head, neck and heart. Organs that are innervated by the sympathetic nerves include eyes, lacrimal gland and salivary glands. Dysfunction of the cervical sympathetic nerve includes Homer's syndrome, which is very identifiable and may include the following reactions: a) partial ptosis (drooping of the upper eyelid from loss of sympathetic innervation to the superior tarsal muscle, also known as Müllers muscle); b) upside-down ptosis (slight elevation of the lower lid); c) anhidrosis (decreased sweating on the affected side of the face); d) miosis (small pupils, for example small relative to what would be expected by the amount of light the pupil receives or constriction of the pupil to a diameter of less than two millimeters, or asymmetric, one-sided constriction of pupils); e) enophthalmos (an impression that an eye is sunken in); f) loss of ciliospinal reflex (the ciliospinal reflex, or pupillary-skin reflex, consists of dilation of the ipsilateral pupil in response to pain applied to the neck, face, and upper trunk. If the right side of the neck is subjected to a painful stimulus, the right pupil dilates about 1-2 mm from baseline. This reflex is absent in Horner's syndrome and lesions involving the cervical sympathetic fibers.)

Transmural Cryo-Ablation:

An endovascular catheter for transmural ablation may be designed and used to deliver an ablation element through a patient's vasculature to an internal surface of a vessel wall proximate a target ablation site. A cryo-ablation element may be, for example, a cryoablation balloon, a point-ablate cryo-applicator, a flexible cryotube. The ablation element may be made from radiopaque material or comprise a radiopaque marker and it may be visualized using fluoroscopy to confirm position. Alternatively, a contrast solution may be injected through a lumen in the ablation element to verify position. Cyro-ablation energy may be delivered, for example from a source external to the patient such as a canister holding a cryogen or a console, to the cryo-ablation element and through the vessel wall and other tissue to the target ablation site. FIG. 1 depicts in simplified schematic form the placement of a carotid access sheath 1 into a patient 2 via an endovascular approach with a femoral artery puncture. The sheath is depicted in position for insertion of an endovascular transmural cryo-ablation catheter 3 into the vicinity of the left carotid artery bifurcation 4 through a central lumen of the carotid access sheath 1. A distal region of the sheath 5 is shown residing in the left common carotid artery 6. The proximal region of the sheath 7 is shown residing outside of the patient 2, with the sheath's entry point into the patient 8 being in the vicinity of the groin 9. From the sheath's entry point 8, the sheath enters a femoral artery 10, and traverses the abdominal aorta 11, the aortic arch 12, and into the left common carotid artery 6. The carotid access sheath 1 may be commercially available, or may be configured specifically for endovascular transmural cryo-ablation of a carotid body. The techniques for placing a carotid access sheath 1 into position as depicted are known to those skilled in the art of endovascular carotid procedures.

Alternatively, an endovascular approach may involve access via a radial or brachial artery. In addition, the superficial temporal artery may be a potential access route to the external carotid artery at the level of the carotid bifurcation and carotid septum. Trans-superficial temporal artery access refers to puncturing a superficial temporal artery and inserting the distal end of an endovascular transmural carotid body ablation catheter into the superficial temporal artery in a retrograde direction and into the vicinity of the associated intercarotid septum for the purpose of modulating a function of a carotid body.

A method has been conceived to reduce or inhibit chemoreflex generated by a carotid body in a patient, to reduce afferent nerve sympathetic activity of carotid body nerves to treat a sympathetically mediated disease, the method comprising: inserting a catheter into a superficial temporal artery of the patient in the retrograde direction, positioning the catheter such that a distal section of the catheter adopted to delivery of cryogenic cooling is positioned in the external carotid artery proximate to a carotid body of the patient; pressing an ablation element against the wall of an external carotid artery, and/or an internal carotid artery adjacent to the carotid body, supplying cooling refrigerant to the ablation element(s) wherein the refrigerant is supplied by an supply apparatus outside of the patient; applying the cryogenic energy to the ablation element(s) to ablate tissue proximate to or included in the carotid body; achieving cryoadhesion (contact freezing, the bond between the external surface of the ablation element and the tissue being treated; facilitated by moisture on the tissue) in order to retain the energy element in the desired position adhering to the wall of the external carotid artery, optionally rewarming the cryogenic element, and removing the ablation device from the patient; wherein a carotid body chemoreflex function is inhibited or sympathetic afferent nerve activity of carotid body nerves is reduced due to the ablation.

Figure 2A:
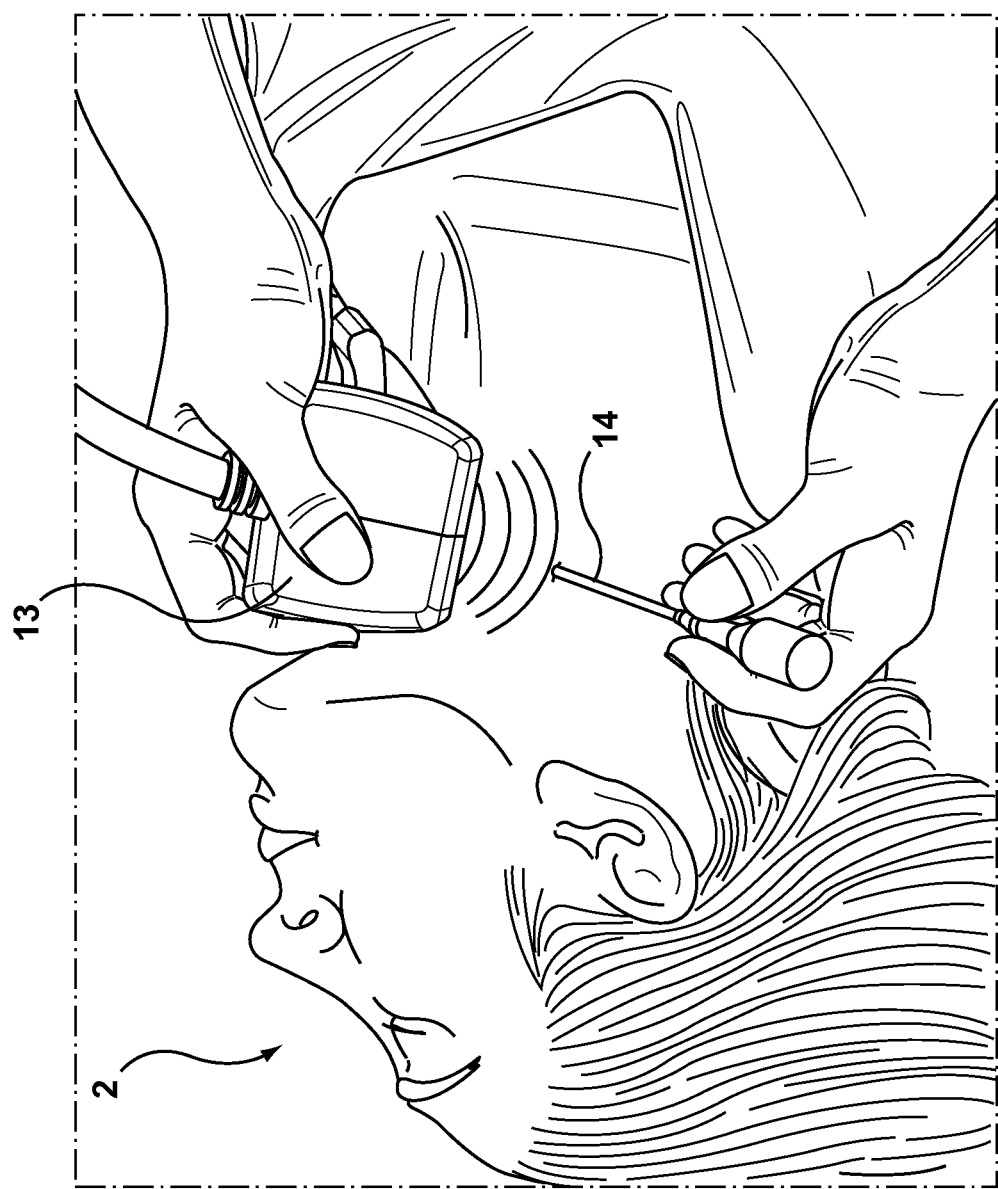
FIG. 2A is an illustration showing a percutaneous access needle being inserted into the target region for carotid body ablation using ultrasonic imaging guidance.
Figure 2B:
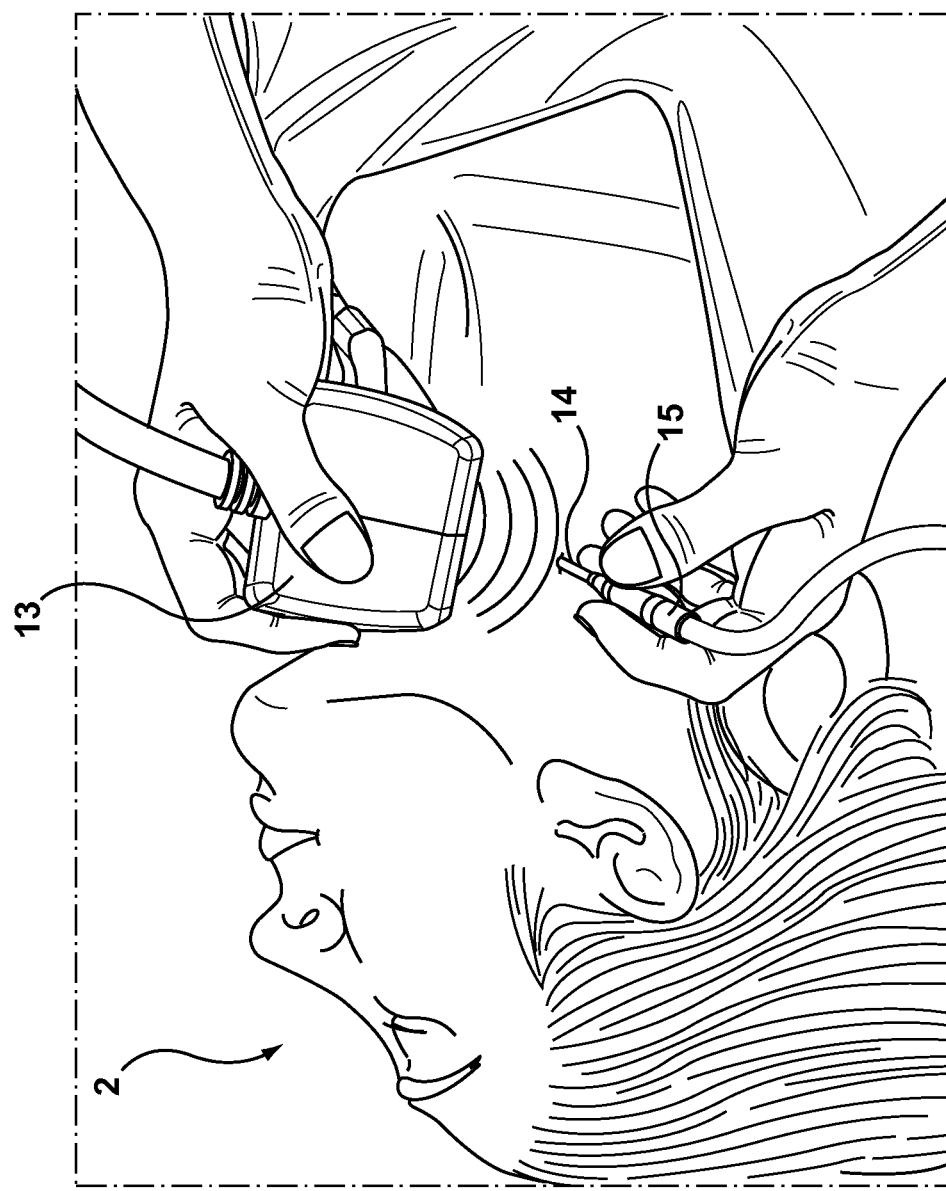
FIG. 2B is an illustration showing a percutaneous cryo-ablation probe in position for carotid body ablation with an ultrasonic imaging probe being used to monitor the boundary of frozen tissue.

Percutaneous Cryo-Ablation:

FIGS. 2A and 2B are illustrations of percutaneous access procedures for percutaneous carotid body cryo-ablation. FIG. 2A shows an extracorporeal ultrasonic imaging transducer guiding insertion of percutaneous cannula 14 into a target site for carotid body cryo-ablation. The cannula 14 may have an echogenic coating to facilitate visualization with sonography. The echogenic coating may include microbubbles of gas immobilized in the polymeric coating. Once the cannula 14 is positioned with its distal end near or in a target ablation site, for example as confirmed using visualization such as ultrasound sonography, a trocar may be removed from the cannula 14 and a cryo-ablation probe 15 may be inserted into a lumen of the cannula 14 as shown in FIG. 2B. As shown, an operator is holding an ultrasonic imaging probe 13 against the skin on the neck. Alternatively, an imaging probe may incorporate a cannula guide in order to facilitate cannula positioning and visibility by keeping it in plane of a monographic image.

Biplane transducer arrays that are rotated (for example 90 degrees) relative to each other (e.g., form a T shape) are used to allow a doctor to view two image planes at once. The purpose of biplane imaging is to enable doctor to visualize simultaneously the cannula or ablation needle and the carotid arteries. The imaging plane for visualization of carotid arteries or a jugular vein may include Doppler imaging modes such as pulsed wave Doppler mode. A color Doppler image of blood vessels can enable distinction of veins and arteries and assist navigation of ablation instruments into the carotid septum.

Optionally, once an initial cannula is placed in a desired location the channel made in the tissue by the cannula may be dilated from a small diameter to a larger diameter cannula by exchanging the larger diameter cannula over the smaller diameter cannula or over a wire. This may provide a larger working channel for a percutaneous ablation probe if needed while allowing the use of a smaller diameter cannula for initial placement. Alternatively, a cryo-ablation probe may be inserted through tissue to a target ablation site directly (e.g., without the use of a cannula as shown in FIG. 2B).

Figure 4:
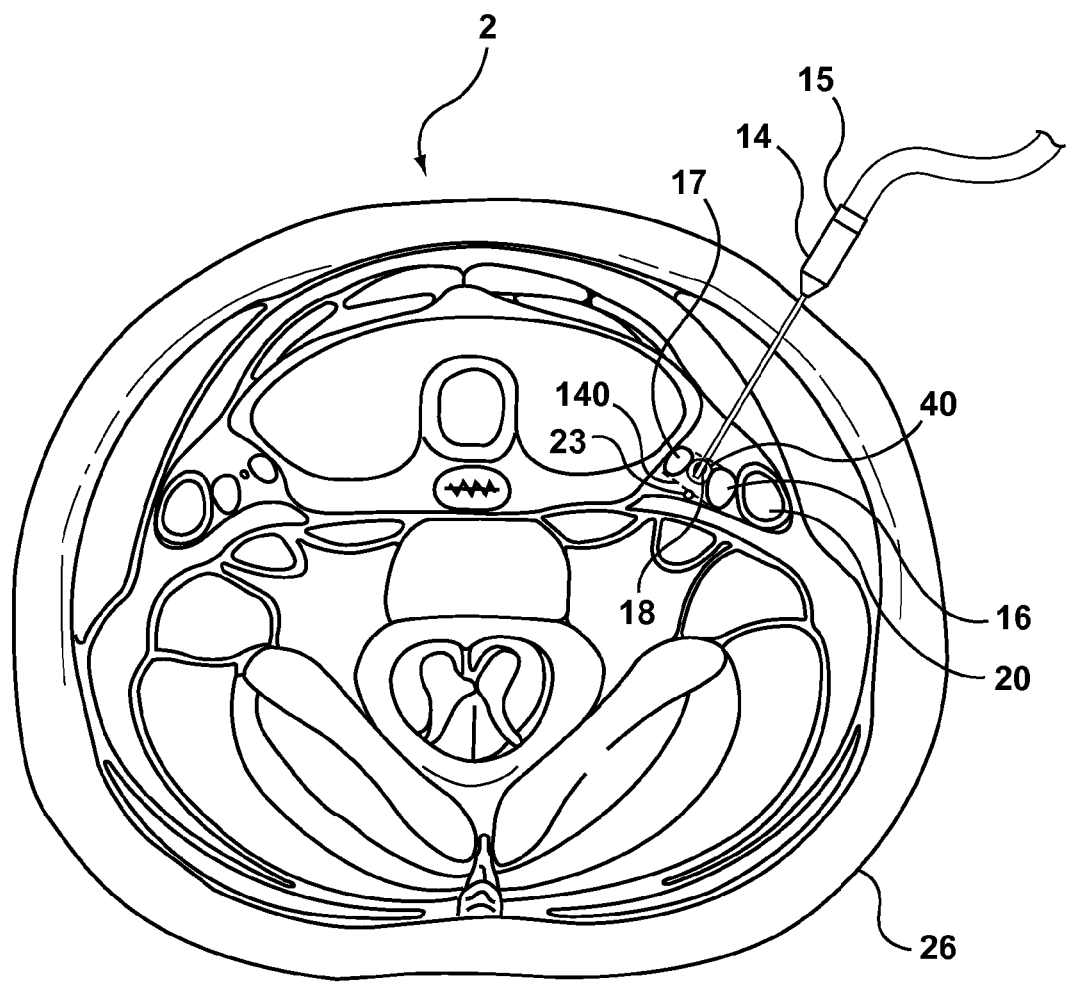
FIG. 4 is an illustration of a cross sectional view of a patient's neck showing a percutaneous cryo-ablation probe in position for cryo-ablation of a carotid body.

FIG. 4 is a cross sectional illustration of a neck of a patient 2 depicting a percutaneous cryo-ablation probe 15 ablating a carotid body 18 and other tissue within an intercarotid septum 140, showing a zone of frozen tissue 40 between external carotid artery 17 and internal carotid artery 16. It may be desired to avoid injury of important non-target nerves, for example a sympathetic nerve 23 or other important non-target nerves located medially to the septum 140. Such nerves may be located just outside of a medial plane of a carotid sheath. Jugular vein 20 may obscure access to the carotid septum 140 with the straight cannula 14. A jugular vein may be repositioned relative to carotid arteries 17 and 16 by rotating of the patient's neck 26 or external manipulation of the vein.

Embodiments of Cryogenic CBA Devices

Figure 5:
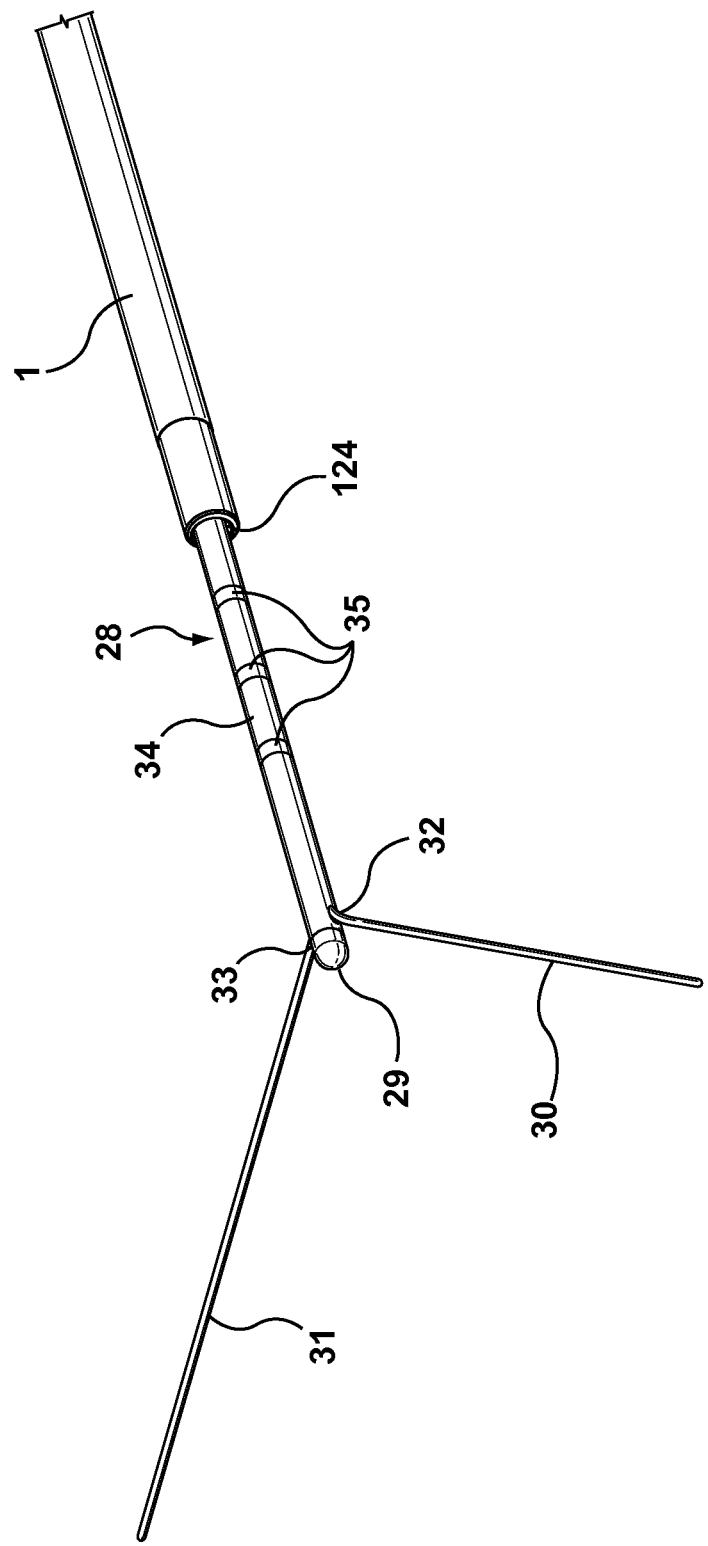
FIG. 5 is a schematic view of a cryo-ablation catheter with two side exiting guide wires.

FIG. 5 depicts the distal region of a carotid access sheath 1 with distal region of an Endovascular Transmural Cryo-Ablation (ETCA) catheter comprising two side-exiting guide wire ports, which will hereby be referred to as the 2-Wire ETCA catheter 28, extending from the central lumen 124 of carotid access sheath 1. The 2-Wire ETCA catheter 28 may comprise a cryo-ablation element 29 mounted in a vicinity of a distal end of the catheter, at least two side exiting guide wire ports 32 and 33 in substantial diametric opposition to each other in the vicinity of the distal end, a catheter shaft 34 comprising at least two guide wire lumens, not shown, in communication with guide wire ports 32 and 33, a means to connect the cryo-ablation element 29 to a cryogenic fluid source in the vicinity of the proximal end, not shown, and a means for inserting a guide wire into the guide wire lumens at the proximal end consisting of female luer fittings or Touy Borst fittings, not shown. The 2-Wire ETCA catheter 28 is depicted here with two guide wires 30 & 31 exiting guide wire ports 32 and 33. Guide wire ports 32 and 33 may be configured such that guide wires 30 and 31 exit the guide wire ports 32 and 33 at an angle of approximately 45 degrees as depicted, or may be configured for a guide wire exit angle that is greater than or less than that depicted. Guide wire ports 32 and 33 and corresponding lumens may be configured for use with guide wires 30 and 31 between 0.014" and 0.018" diameter. The distance of the guide wire ports from the distal tip may be fixed as depicted, or may be user selectable by a distance selection means, not shown. The distance between guide wire port 32 and the distal tip may be the same or different than the distance between guide wire port 33 and the distal tip. The distance between the distal tip and either guide wire port 32 and 33 may be independently selectable by the user. Cryo-ablation element 29 may be associated with at least one temperature sensor, not shown. In addition cryo-ablation element 29 may also be configured for monopolar or bipolar RF ablation, neuroprotective warming, or tissue thawing. Catheter shaft 34 may comprise at least one catheter shaft electrode 35 configured for electrical neuro-modulation. Cryo-ablation element 29 may be configured for electrical neuro-modulation independently or in conjunction with catheter shaft electrode(s) 35. The 2-Wire ETCA catheter 28 may be configured for use with a carotid access sheath 1 having a working length between 100 cm and 140 cm, and a diameter of 5 French to 8 French. The techniques for constructing the 2-Wire ETCA catheter 28 as depicted is familiar to those skilled in the art of catheter making, and therefore are not further elaborated.

Figure 6:
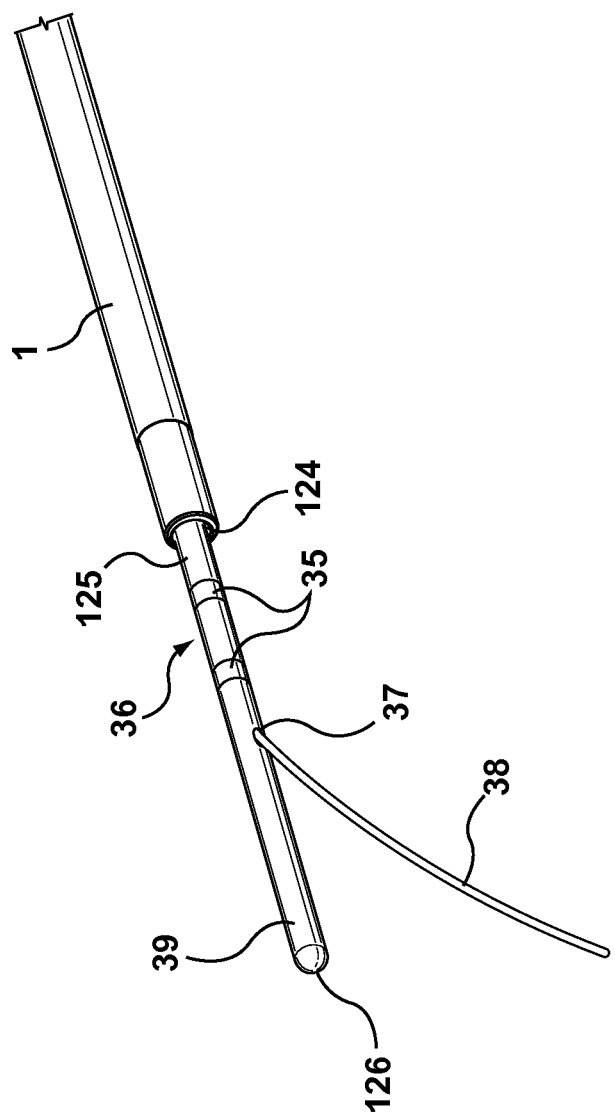
FIG. 6 is a schematic view of a cryo-ablation catheter with a single side exiting guide wire

FIG. 6 depicts a distal end of a carotid access sheath 1 with an Endovascular Transmural Cryo-Ablation (ETCA) catheter comprising a single side-exiting guide wire port 37, which will hereby be referred to as the Side-Wire ETCA catheter 36, extending from the central lumen 124 of carotid access sheath 1. Side-Wire ETCA catheter 36 comprises a cryo-ablation element 39 mounted in vicinity of a distal end, and a side exiting guide wire port 37 in vicinity of the distal end but proximal to the cryo-ablation element 39, catheter shaft 125 comprising a guide wire lumen, not shown, in communication with guide wire port 37, a connector that connects cryo-ablation element 39 to a cryogen fluid source in the vicinity of a proximal end, not shown, and a means for inserting a guide wire into the guide wire lumen at the proximal end consisting of female luer fitting or Touy Borst fitting, not shown. Side-Wire ETCA catheter 36 is depicted here with guide wire 38 exiting guide wire port 37. Guide wire port 37 may be configured such that guide wire 38 exits guide wire port 37 at an angle of approximately 45 degrees as depicted, or may be configured for a guide wire exit angle that is greater than or less than that depicted. Guide wire port 37 and corresponding lumen may be configured for use with a guide wire between 0.014" and 0.018" diameter. The distance of the guide wire port 37 from the distal tip 126 may be fixed as depicted, or may be user selectable by a distance selection means, not shown. For example, the distance between a guide wire port 37 and the distal tip 126 may be between about 10 to 20 mm, which may position a cryo-ablation element 39 at an ideal location on a carotid septum to target a carotid body or its nerves for cryo-ablation. Cryo-ablation element 39 may be associated with at least one temperature sensor, not shown. Cryo-ablation element 39 may also be configured for monopolar or bipolar RF ablation, neuroprotective warming, or tissue thawing. Catheter shaft 125 may comprise at least one catheter shaft electrode 35 configured for electrical neuro-modulation. Cryo-ablation element 39 may be configured for electrical neuro-modulation independently or in conjunction with catheter shaft electrode(s) 35. Side-Wire ETA catheter 36 is configured for use with a carotid access sheath 1 having a working length between 100 cm and 140 cm, and a diameter of 5 French to 8 French. The techniques for constructing the Side-Wire ETA catheter 36 as depicted is familiar to those skilled in the art of catheter making, and therefore are not further elaborated.

Figure 7:
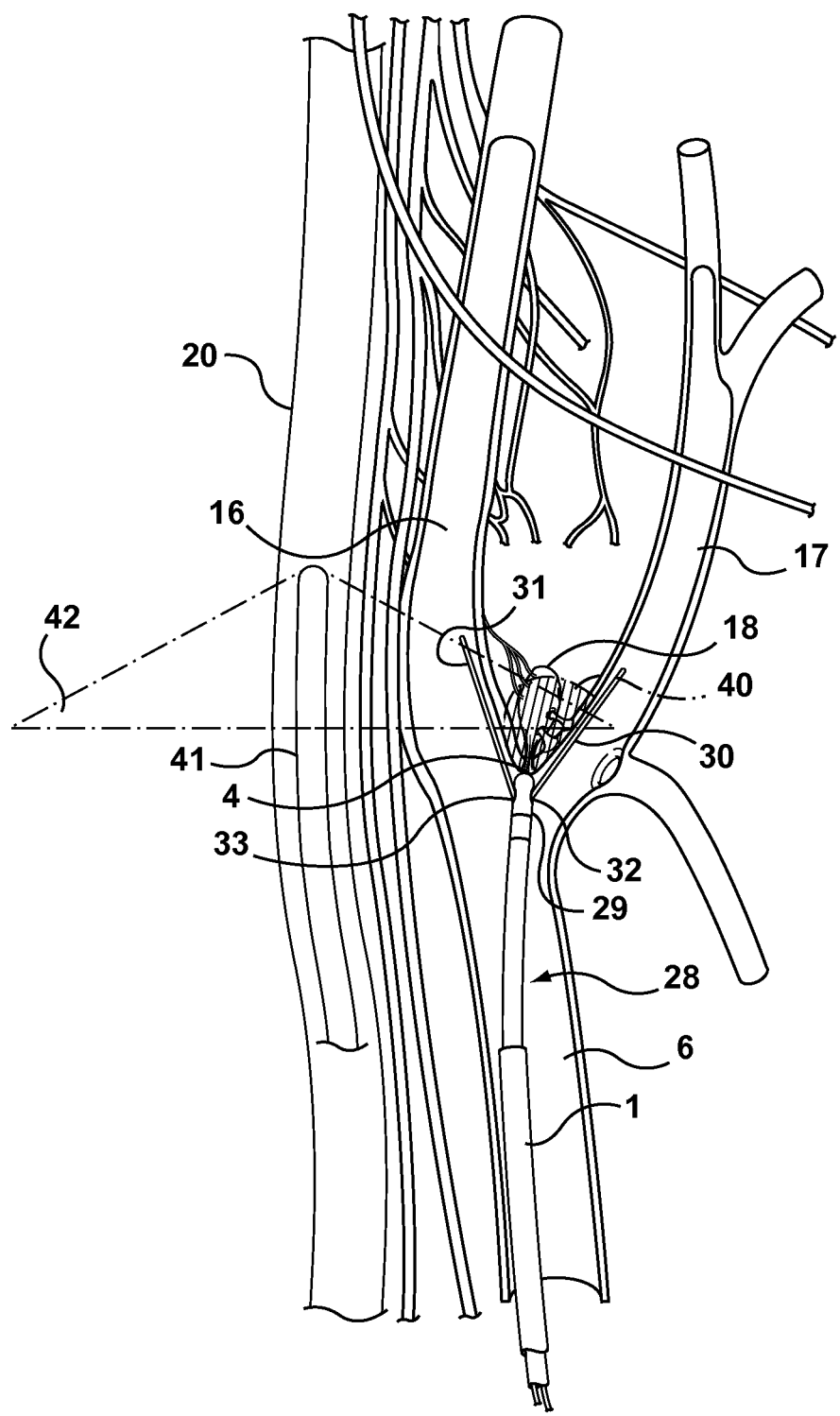
FIG. 7 is a cutaway illustration of a lateral view of a patient's right carotid artery system with a schematic view of a cryo-ablation catheter, with side exiting guide wires, positioning a cryo-ablation element on an inner wall of a carotid bifurcation to transmurally cryo-ablate a carotid body while the boundary of the frozen tissue is monitored by an ultrasonic imaging catheter positioned in the internal jugular vein.

FIG. 7 depicts in simplified schematic form the 2-Wire ETCA catheter 28 in position for ablation of a carotid body 18 immediately following an ablation. As depicted the distal tip of ablation element 29 is positioned against a carotid bifurcation 4, with a guide wire 31 exiting side guide wire port 33 into the internal carotid artery 16, and a second guide wire 30 exiting side port 32 into the external carotid artery 17 as shown. Guide wires 30 and 31 provide a means for positioning and maintaining the distal tip of ablation element 29 centered at the bifurcation 4 in a stable manner during ablation. The cryo-ablation zone 40 of frozen tissue is depicted encompassing the periarterial space comprising the carotid body 18. Also depicted is the carotid access sheath 1 used for placement of the 2-Wire ETA catheter 28 into the common carotid artery 6. Also, an optional intravascular ultrasonic imaging catheter 41 configured for imaging the boundary between frozen tissue, and not frozen tissue is depicted residing in internal jugular vein 20 with ultrasonic imaging beam 42 penetrating the cryo-ablation zone 40. Ultrasonic imaging provides the user with an indication that the zone of frozen tissue is, or is not within the determined boundary for safe cryo-ablation. Alternatively, extracorporeal ultrasound sonography may be used to visualize the zone of frozen tissue.

Figure 8:
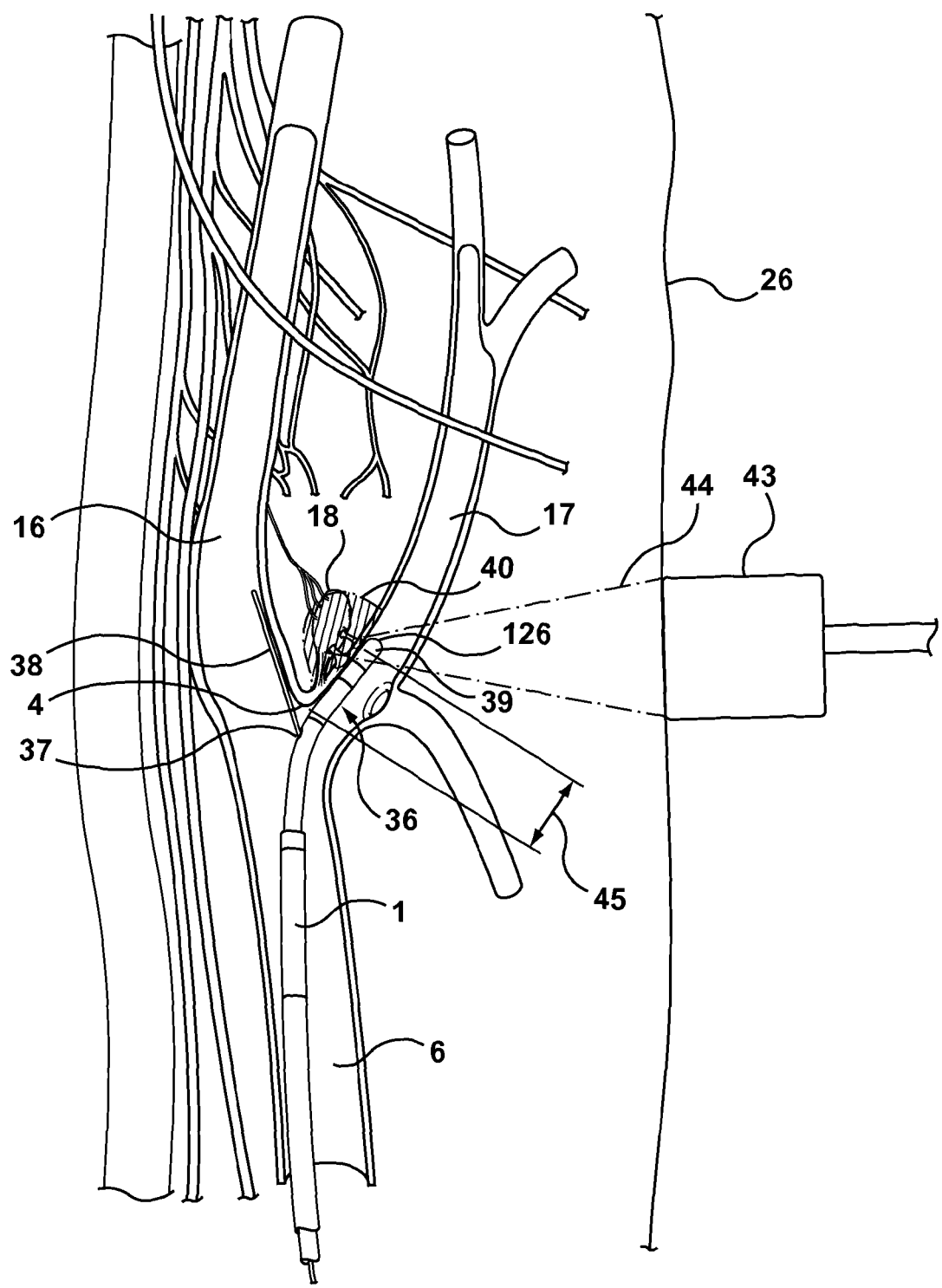
FIG. 8 is a cutaway illustration of a lateral view a patient's right carotid artery system with a schematic view of a cryo-ablation catheter, with a side exiting guide wire, positioning a cryo-ablation element on an inner wall of an external carotid artery to transmurally cryo-ablate a carotid body while the boundary of frozen tissue is monitored by an extracorporeal ultrasonic imaging probe.

FIG. 8 depicts in simplified schematic form Side-Wire ETCA catheter 36 in position for ablation of a carotid body 18 immediately following a cryo-ablation. As depicted cryo-ablation element 39 is positioned against the wall of the external carotid artery 17 at a position distal to the carotid bifurcation 4, which distance 45 as shown may be predetermined prior to the placement of the Side-Wire ETCA catheter 36, or may be a distance suitable for positioning a cryo-ablation element 39 proximate a majority of patients' carotid bodies and carotid body nerves relative to carotid bifurcation 4, for example approximately 5 mm to 20 mm. Guide wire 38 is shown exiting side guide wire port 37 into an internal carotid artery 16. The guide wire 38 in conjunction with guide wire port 37 provide a means for positioning cryo-ablation element 39 against a wall of an external carotid artery 17 at a predetermined distance 45 based on the distance between the distal tip 126 and the guide wire port 37. The force of contact between cryo-ablation element 39 and the wall of external carotid artery 17 can be influenced by the selection of the stiffness and/or diameter of the guide wire 38, the angle of exit of the guide wire 38, as well as the distance between distal tip 126 and guide wire port 37. The cryo-ablation zone 40 of frozen tissue is depicted encompassing the periarterial space comprising the carotid body 18. Also depicted is a carotid access sheath 1 used for placement of Side-Wire ETCA catheter 36 into a common carotid artery 6. Also, an optional extracorporeal ultrasonic imaging probe 43 configured for imaging a boundary between frozen tissue, and not frozen tissue is depicted imaging from the surface of the patient's neck 26 with ultrasonic imaging beam 44 focused on an area around the cryo-ablation zone 40. Ultrasonic imaging provides a user with an indication that the zone of frozen tissue is, or is not within the determined boundary for safe cryo-ablation. Ultrasonic imaging probe 43 may have Doppler flow detection and visualization capability in order to assist an operator in monitoring location of the ETCA catheter and blood flow in the carotid arteries.

Figure 9:
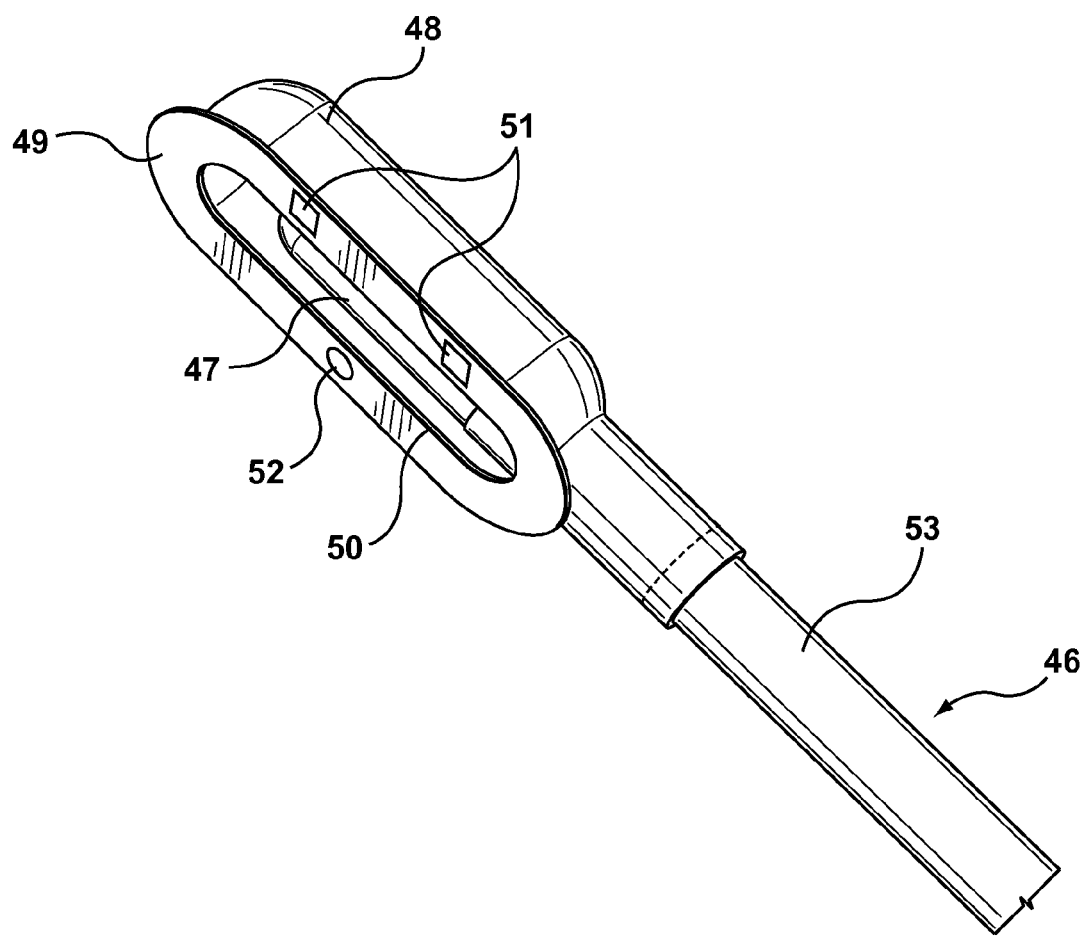
FIG. 9 is a schematic view of an endovascular cryo-ablation catheter having a side suction element with a cryo-ablation element.

FIG. 9 depicts the distal end of an Endovascular Transmural Cryo-Ablation Lateral Suction (ETCALS) catheter 46. ETCALS catheter 46 comprises a catheter shaft 53, a cryo-ablation element 47 mounted in the vicinity of the distal end of the catheter shaft as shown, a lateral suction cup 48 also mounted in the vicinity of the distal end of the catheter shaft 53, and partially surrounding ablation element 47 as shown, a proximal terminal, not shown, comprising a cryogen fluid connector, and a suction connector. Catheter shaft 53 comprises a lumen in fluidic communication between the lateral suction cup 48 and the suction connector of the proximal terminal of the catheter located outside of the body (not shown), and a cryogen fluid supply conduit and a cryogen fluid return conduit in fluidic communication with cryo-ablation element 47 and cryogen supply and return connectors at the proximal terminal. Catheter shaft 53 is fabricated from a polymer suited for catheter construction such as Pebax or polyurethane, and may comprise a braided structure within its wall to provide torsional rigidity while maintaining axial flexibility to aid in directional positioning of lateral suction cup 48. In addition, cryo-ablation element 47 may be configured for monopolar or bipolar RF ablation, neuroprotective warming, or to thaw frozen tissue, monopolar or bipolar neural stimulation, or monopolar or bipolar neural blockade. Lateral suction cup 48 is fabricated from an elastomer such as silicone rubber or polyurethane, and may have radiopaque markers 51 and 52 molded into a wall, or disposed upon a wall using an adhesive. The number of radiopaque markers, size, shape, and their positions provide the user with a substantially unambiguous indication of the position of lateral suction cup 48 within a carotid artery. Lateral suction cup 48 is bonded to the distal end of catheter shaft 53 with the ablation element 47 substantially surrounded by lateral suction cup 48 except for ablation aperture 50. Lateral suction cup 48 may comprise a suction flange 49 to facilitate suction fixation to the wall of a carotid artery during cryo-ablation. The ETCALS catheter 46 is configured for use through a carotid access sheath, with a central lumen between 6 French and 12 French, not shown. The working length of the ETCALS catheter may be between about 100 cm to 140 cm.

Figure 10:
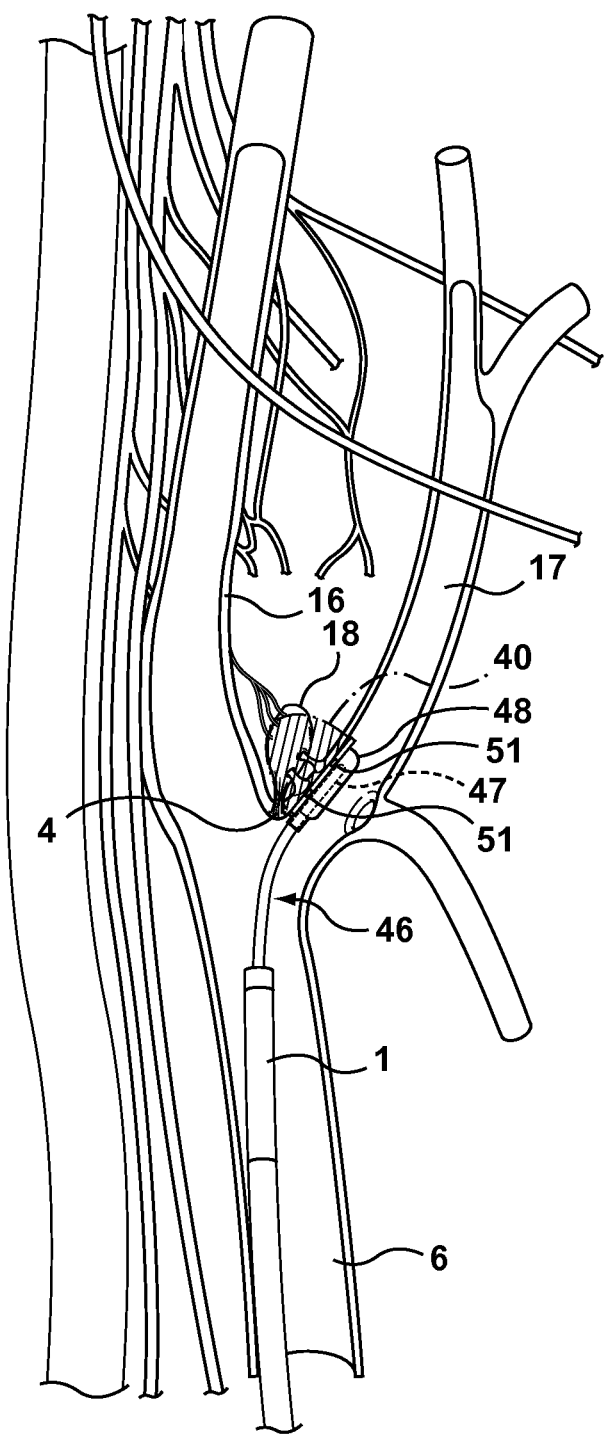
FIG. 10 is a cutaway illustration of a lateral view a patient's right carotid artery system with a schematic view of an endovascular cryo-ablation catheter having a side suction element with a cryo-ablation element positioned in an external carotid artery for transmural cryo-ablation of a carotid body.

FIG. 10 depicts a, ETCALS catheter 46 in position for ablation of a carotid body 18 immediately following a cryo-ablation 40. The ETCALS catheter suction cup 48 is shown in position against the wall of external carotid artery 17 immediately adjacent to carotid body 18 being held in place by suction applied to lateral suction cup 48 during cryo-ablation element 47 activation.

Figure 11:
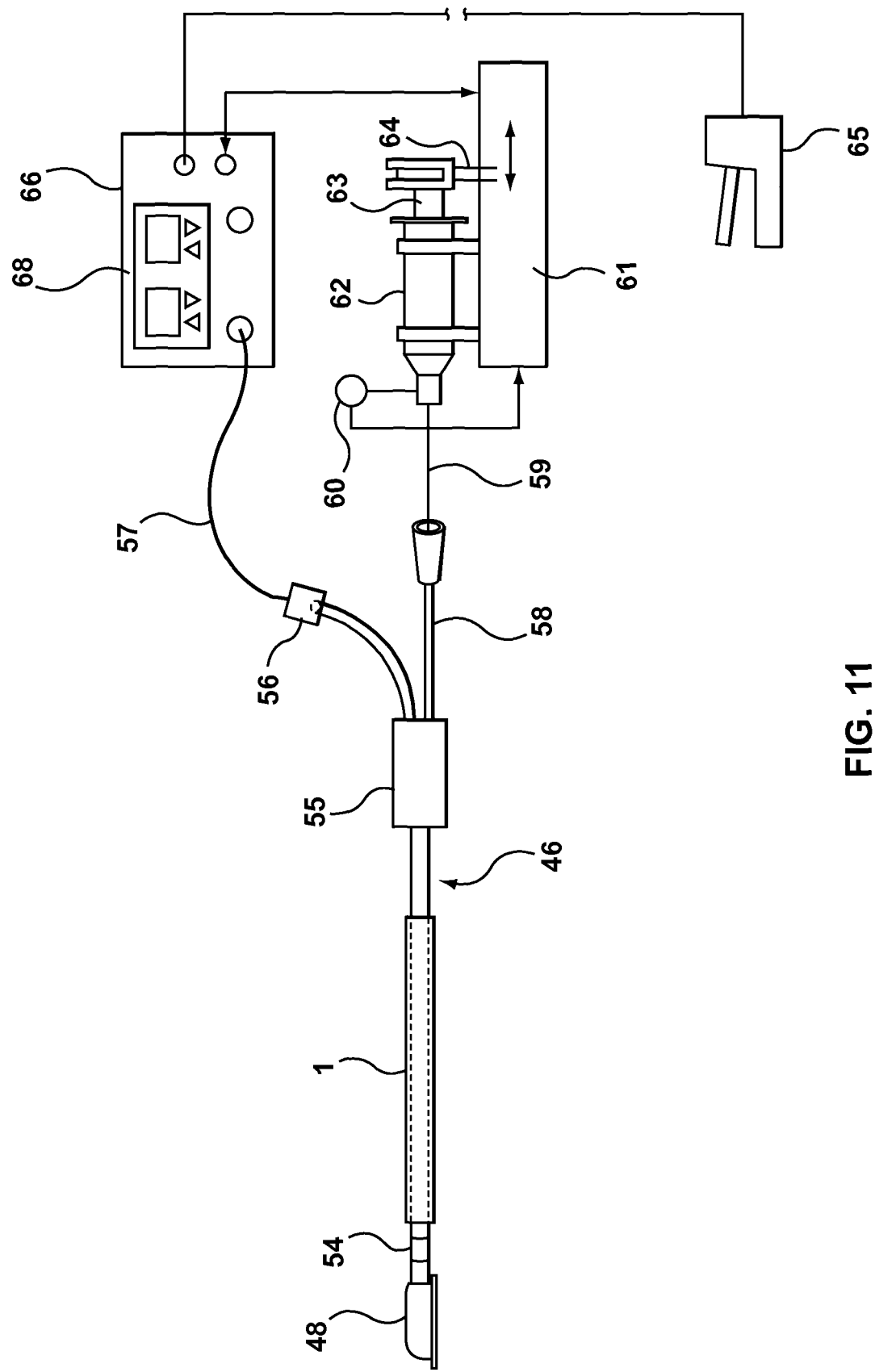
FIG. 11 is a schematic view of an endovascular cryo-ablation system comprising a suction fixation means.
Figure 12:
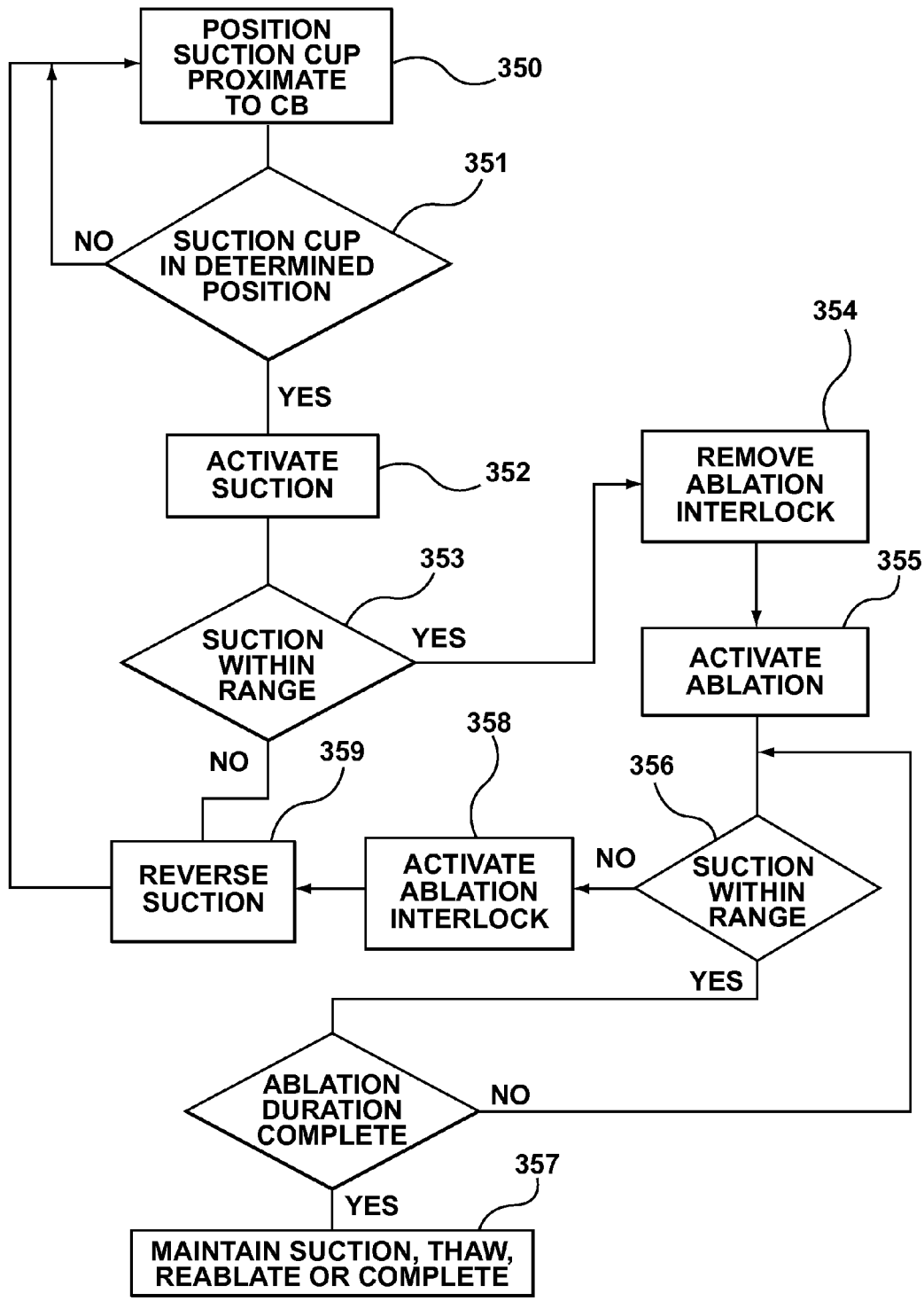
FIG. 12 is a flow chart of an algorithm for operating an endovascular ablation catheter having a suction element with a cryo-ablation element.

FIG. 11 depicts in schematic form a system for carotid body cryo-ablation using an ETCALS catheter 46. The system comprises an ETCALS catheter 46, a carotid access sheath 1, control module 66, a suction module 61, a foot-switch 65, and umbilical 57 that connects the ETCALS catheter 46 to the control module 66. The control module 66 comprises a source of cryogenic fluid, not shown, a means to control cryo-ablation based on user selection of power control algorithms, and or by means of temperature control algorithms based on signals from temperature sensor(s) associated with cryo-ablation element 47, not shown, a means for controlling the suction module 61 in response to vacuum sensor 60, and foot switch 65, a user interface 68 that provides the selection of cryo-ablation parameters, an indication of the status of the system, a means to initiate an ablation, and a means to terminate an ablation. Suction module 61 may comprise a syringe cylinder 62, syringe plunger 63, syringe actuator 64, and a vacuum sensor 60. Alternatively a suction module may comprise a pump with an actuator and vacuum sensor not shown. Foot switch 60 is configured to actuate suction by switch depression, and deactivate suction upon removal of said depression. As shown in FIG. 12, the system may be used in the following manner:

Step i 350, the carotid access sheath 1 is inserted into a patient and the distal end is positioned within the common carotid artery 6. The ETCALS catheter 46 is inserted into the proximal central lumen 124 of carotid access sheath 1 and advanced through central lumen 124 until the suction cup 48 extends beyond the carotid access sheath 1. The suction cup 48 is maneuvered using visual guidance (e.g., fluoroscopy, sonography) into contact with external carotid artery 17 proximate a carotid body 18.

Step ii 351, the suction cup position is determined to be in a desired position or not, if yes proceed to step iii, if not proceed to step i;

Step iii 352, foot switch 65 is depressed activating suction module 61, for example: Syringe actuator 64 is opened resulting in suction, or alternatively vacuum pump is activated;

Step iv 353, vacuum pressure is continuously monitored by vacuum sensor 60 to determine if suction is within range or not, if yes proceed to step v, if not proceed to step i;

Step v 354, when vacuum pressure reaches a predetermined level (e.g., between 10 mmHg and 100 mmHg) the syringe movement is stopped, or alternatively vacuum pump is stopped, and a cryo-ablation interlock is removed allowing user actuated cryo-ablation;

Step vi 355, a cryo-ablation or a temporary cryo-block is activated (e.g., cryogen fluid flow is initiated);

Step vii 356, If the vacuum pressure decays to a level below the predetermined level, then the syringe actuator 64 is again moved to open, or alternatively the vacuum pumps is activated until the predetermined vacuum level is re-achieved. If the predetermined level cannot be achieved initially, or re-achieved within a syringe volume displacement between 1cc and 20 cc then the ablation interlock remains in activation, or is reactivated, and the blood removed from the patient by the suction module is reinserted back into the patient. User interface 68 is configured to provide the user with an indication of the status of suction module 61, as well as the status of the cryo-ablation interlock.

Step viii 357, once the cryo-ablation or temporary cryo-block is complete, suction may be continued so position is maintained while tissue thaws. Maintaining position may allow a repeat cryo-ablation to be performed in the same location, which may improve efficacy.

The ETCALS catheter 46, and the carotid access sheath 1 are withdrawn from the target area.

Control module 66, shown in FIG. 11, may be configured to supply electrode(s) mounted in the region of the distal region of ETCALS catheter 46, not shown with neural stimulation energy, and/or neural blockade energy. The ETCALS catheter 46 may also be configured to work with a needle device used to access the periarterial space of the carotid septum 140 for the purposes of applying ablation energy, neural stimulation energy, neural blockade energy, neural stimulation chemicals, neural blockade chemical, neuro-protective warming, or placement of a temperature sensor, not shown. The control module 66 may be configured to supply and control the function of said needle device(s).

Figures 13A, 13B:
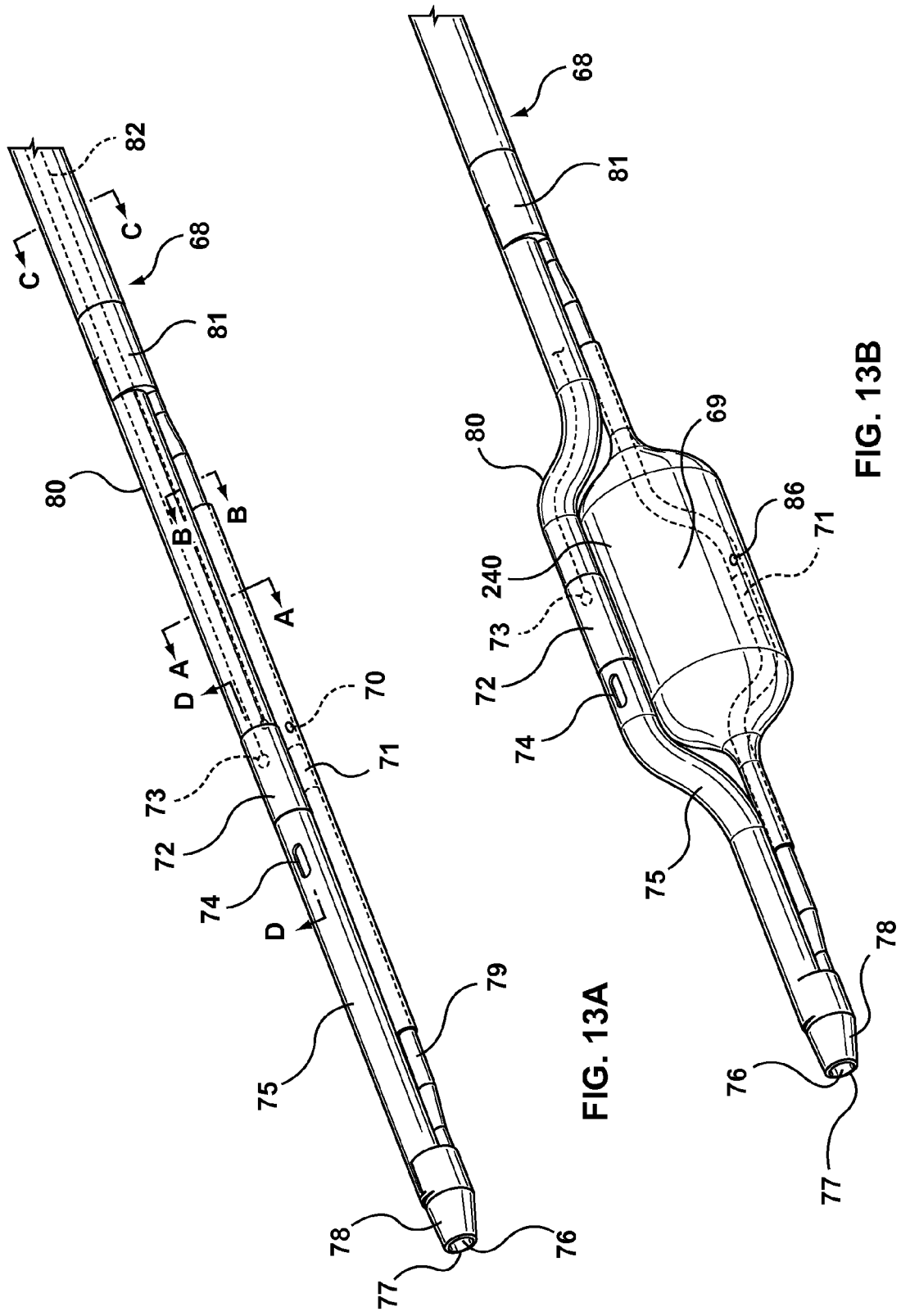
FIG. 13A is a schematic view of an endovascular catheter having a deployable balloon and a cryo-ablation element, in an undeployed state.
FIG. 13B is a schematic view of an endovascular catheter having a deployable balloon and a cryo-ablation element, in a deployed state.
Figure 13C:
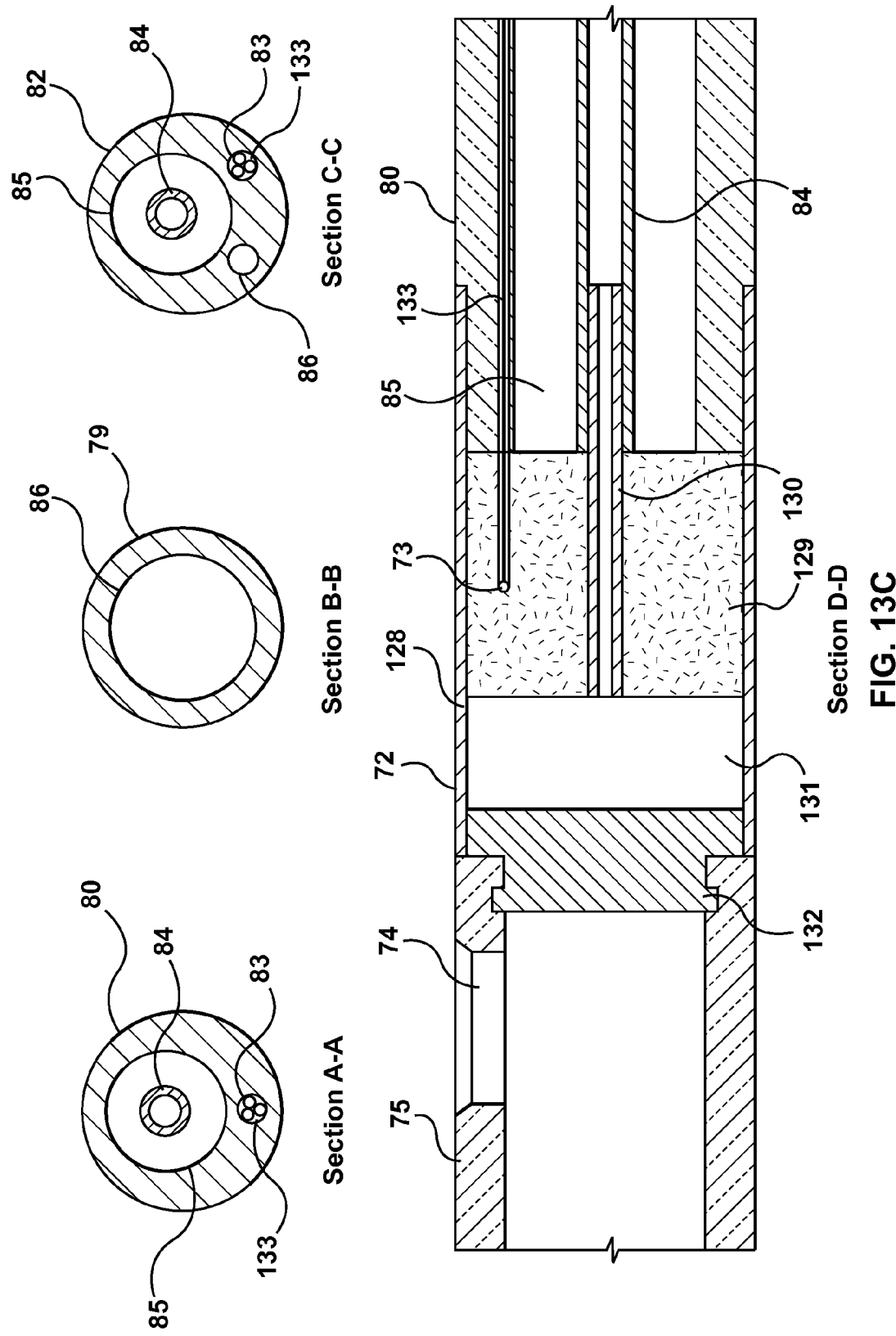
FIG. 13C depicts the cross sectional views from FIG. 13A.

FIG. 13A depicts an Endovascular Transmural Cryo Ablation Balloon (ETCAB) catheter 68 with a balloon not inflated. FIG. 13B depicts the ETCAB catheter 68 with the balloon inflated. FIG. 13C depicts sectional views A-A, B-B, C-C, and D-D from FIG. 13A. ETCAB catheter 68 comprises common catheter shaft 82, cryo catheter shaft 80, guide wire shaft 75 in extension of cryo catheter shaft, distal melt liner 78, balloon shaft 79, cryo-ablation element 72, balloon 69, proximal melt liner 81, and a proximal terminal, not shown. The proximal terminal comprises a cryogen fluid supply and return connector, an electrical connector, and a fluid connector for inflation of balloon 69. Common catheter shaft 82 comprises balloon inflation lumen 86, electrical wire lumen 83, and cryogen gas return lumen 85. Cryo catheter shaft segment 80 comprises electrical wire lumen 83 and cryogen gas return lumen 85. Balloon shaft segment 79 comprises balloon inflation lumen 86. Electrical wire lumen 83 runs from the distal end of cryo shaft segment 80 through proximal melt liner 81, common catheter shaft 82, to the electrical connector of the proximal terminal, not shown. Electrical wire lumen 83 contains wires to connect temperature sensor 73 with the electrical connector of the proximal terminal. Balloon inflation lumen 86 runs from the distal end of balloon shaft 79, through melt liner 81, common catheter shaft 82 to the fluid connector configured for balloon inflation of the proximal terminal, not shown. Distal melt liner 78 forms a connection between guide wire shaft segment 75 and balloon shaft segment 79. Proximal melt liner 81 connects cryo shaft segment 80 and balloon shaft segment 79 to common catheter shaft 82 by thermal bonding technique, which preserves the continuity of cryogen gas return lumen 85, electrical wire lumen 83, and balloon inflation lumen 86. Common catheter shaft 82, distal melt liner 78, cryo shaft segment 80, guide wire shaft segment 75, balloon shaft segment 79, and proximal melt liner 81 are fabricated from a thermoplastic material such as Pebax, or polyurethane. Cryo-ablation element 72 is mounted between cryo shaft segment 80 and guide wire shaft segment 75 as shown. Cryo-ablation element 72 comprises cryo ablation element housing 128, optional heat exchanger 129, capillary tube 130, cryo-ablation element bulkhead 132 and temperature sensor 73. Cryo-ablation element 72 may be a thin-walled metallic structure with high thermal conductivity. Heat exchanger 129 may be a porous metallic structure with high thermal conductivity and is disposed within cryo-ablation element housing 128 in an intimate heat transfer relationship. Heat exchanger 129 may be fabricated using a sintering process of a metal with high thermal conductivity such as copper. Capillary tube 130 is configured to meter the flow of cryogen from cryogen supply tube 84 into expansion/evaporation chamber 131 at a determined rate. Capillary tube 130 may be fabricated, for example, from a stainless steel hypodermic tube or polyimide tube. Optionally a capillary tube may be omitted if a cryogen supply tube 84 and exhaust lumen 85 are sized appropriately. Cryogen supply tube 84 may be bonded by adhesive to capillary tube 130 as shown. Cryogen supply tube 84 may be configured for delivery of a cryogen under high pressure on the order of 100 psi to 2000 psi (for example N2O may be delivered at a pressure around 760 psi). Cryogen supply tube 84 may be fabricated from a polymer such as polyimide, or from a super elastic metal alloy such as Nitinol. Cryogen supply tube 84 is in fluidic communication with cryogen fluid supply connector of the proximal terminal, not shown. Cryogen gas exhaust lumen 85 is in fluidic communication with cryogen return connector of the proximal terminal not shown. Electrical conductor 133 connects temperature sensor 73, and optional neural modulation electrodes, not shown to the electrical connector of the proximal terminal, not shown. Cryo-ablation element 72 may be bonded to the distal end of cryo catheter shaft segment 80. Guide wire shaft segment 75 is bonded to cryo-ablation element bulkhead 132, as shown. Guide wire entry port 74 is distal and in close proximity to cryo-ablation element 72, as shown. An example of a method for placing the catheter 68 includes advancing a guide wire through a patient's vasculature to the patient's external carotid artery then advancing the catheter 68 over the guide wire, that is, the guide wire may pass in to a port at the distal tip 77, through lumen 76 in the guide wire shaft segment 75 and out of the guide wire entry port 74. In an alternate embodiment, the cryo-ablation element is a balloon configured as an evaporator that receives a liquid cryogen, which evaporates and absorbs heat from adjacent tissue and exits the balloon as a gas. The techniques for constructing the alternate embodiment described is familiar to those skilled in the art of cryo-balloon catheter making, and therefore are not further elaborated. Balloon 69 is fabricated from an elastomer such as silicone rubber, and is centrally mounted on balloon shaft segment 79 as shown using adhesive. The wall thickness of balloon 69 may be between 0.1 mm and 0.4 mm when the balloon is un-inflated as depicted in FIG. 13A, and may be inflated to a diameter of 4 mm to 10 mm as depicted in FIG. 13B. Alternatively, balloon 69 may be fabricated from a non-elastomeric material such as PET. Radiopaque marker 71 is mounted centrally on balloon shaft segment 79 as shown. Balloon shaft segment 79 is configured to bend in the opposite direction of the bend in cryo and guide wire shaft segments 80 and 75 respectively as shown in FIG. 13B to provide the user with a substantially unambiguous fluoroscopic indication of the position of cryo-ablation element 72 within a carotid artery using the fluoroscopic spatial relationship between cryo-ablation element 72 and radiopaque marker 71. The inflation fluid enters balloon 69 and is in fluidic communication with balloon inflation lumen 86. Balloon 69 may be configured to contract in the axial direction in reaction to balloon expansion in the radial direction due to balloon inflation. Axial contraction results in balloon shaft 79 buckling and displacing radiopaque marker 71 off the centerline of balloon 69 as shown. Radiopaque marker 71 is shown in substantial diametric opposition to cryo-ablation element 72. The configuration of balloon 69 for axial contraction and radial expansion may comprise inelastic filaments 240 disposed axially within the wall of balloon 69, or inelastic filaments disposed axially on the outer surface of balloon 69, or a woven or knitted structure disposed within the wall of balloon 69 or disposed on the surface of balloon 69. The buckled position of radiopaque marker 71 in substantially diametric opposition to cryo-ablation element 72 may be facilitated by embedding at least one flat metallic wire, not shown, within balloon shaft 79 with the flat side of the wire facing cryo-ablation element 72. The flat wire may be a shape memory alloy such Nitinol, that is formed with a bias, which results in the buckling of balloon shaft 79 in the direction opposite cryo-ablation element 72.

Figure 14:
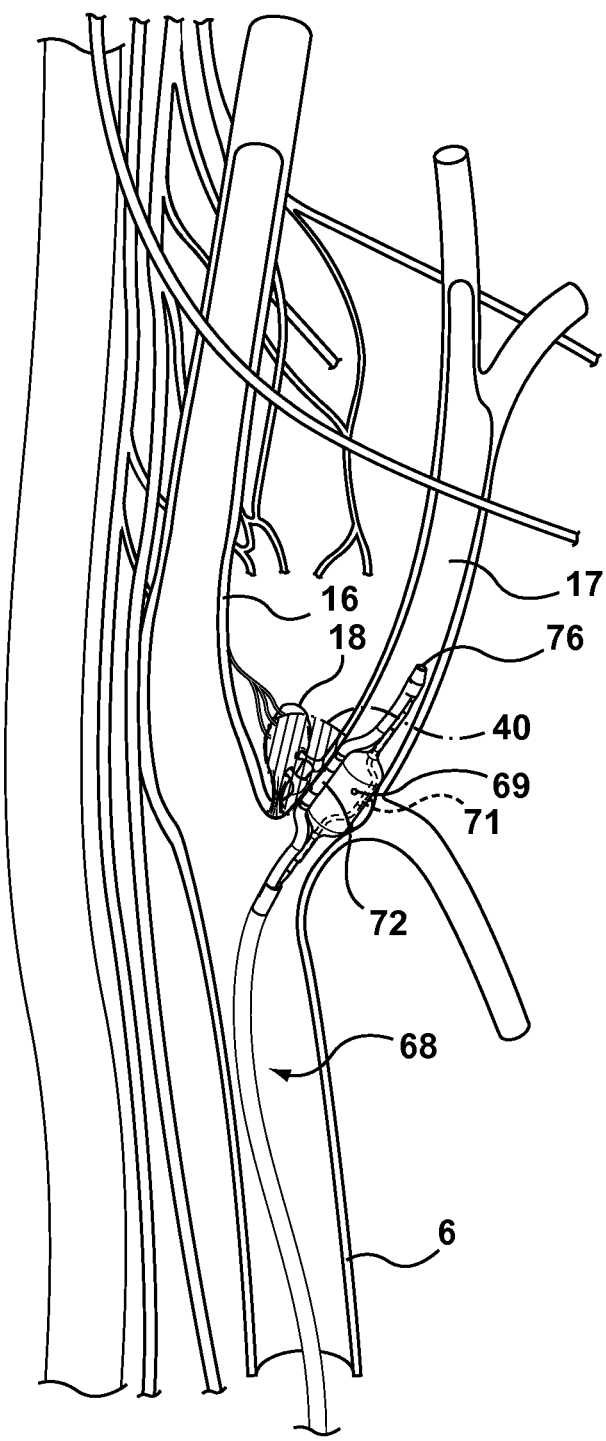
FIG. 14 is a cutaway illustration of a lateral view a patient's right carotid artery system with a schematic view of an endovascular cryo-ablation catheter having a deployable balloon with a cryo-ablation element positioned in the patient's external carotid artery for transmural cryo-ablation of a carotid body.

FIG. 14 depicts ETCAB catheter 68 in position for cryo-ablation of a carotid body 18 immediately following an ablation. As depicted, cryo-ablation element 72 is pressed against the wall of the external carotid artery 17 and adjacent to carotid body 18 by balloon 69. In this depiction, a guide wire is absent. The ablation of carotid body 18 may be accomplished using ETCAB catheter comprising the steps of:

Determining the position and size of a target ablation zone, for example an intercarotid septum 140 (see FIGS. 3A and 3B), for example using fluoroscopy with use of radiocontrast.

Positioning the distal end of ETCAB catheter 68 into the external carotid artery 17 associated with carotid body 18 as shown using a guide wire and fluoroscopic imaging using cryo-ablation element 72, and radiopaque marker 71 as references.

Inflating balloon 69 using the fluid connector of the proximal terminal.

Fluoroscopically confirming cryo-ablation element 72 is in a desired position for carotid body ablation.

Selecting cryo-ablation parameters.

Initiating the ablation.

Maintaining and monitoring low temperature in the balloon for the duration known to cause irreversible tissue damage in the tissue volume defined as carotid septum.

Terminating the ablation.

Deflating balloon 69.

Withdrawing ETCAB catheter 69.

Figure 15A:
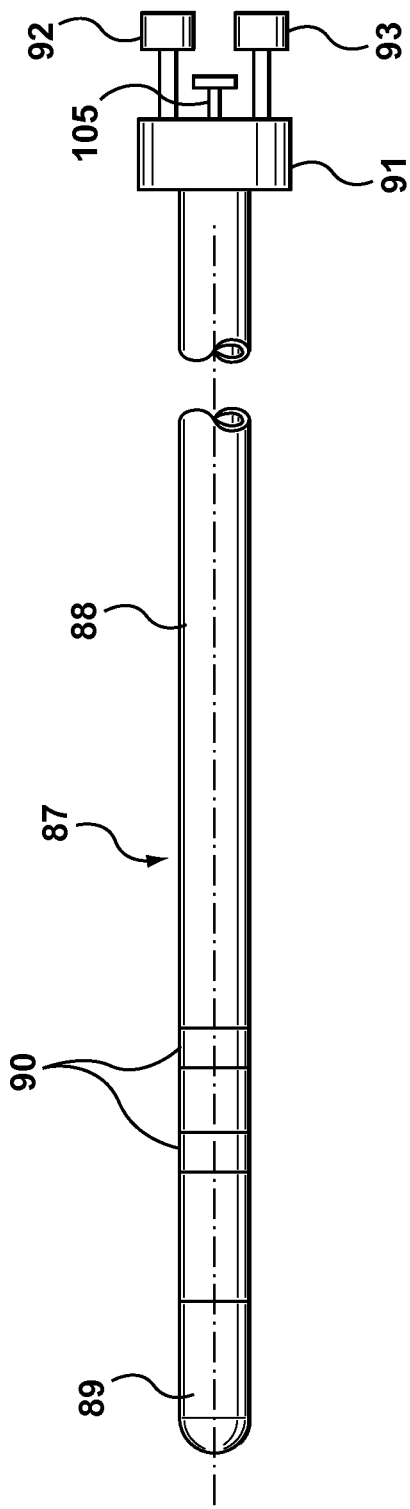
FIGS. 15A and 15B are schematic views of an endovascular cryo-ablation catheter configured for transmural cryo-ablation of a carotid body.
Figure 15B:
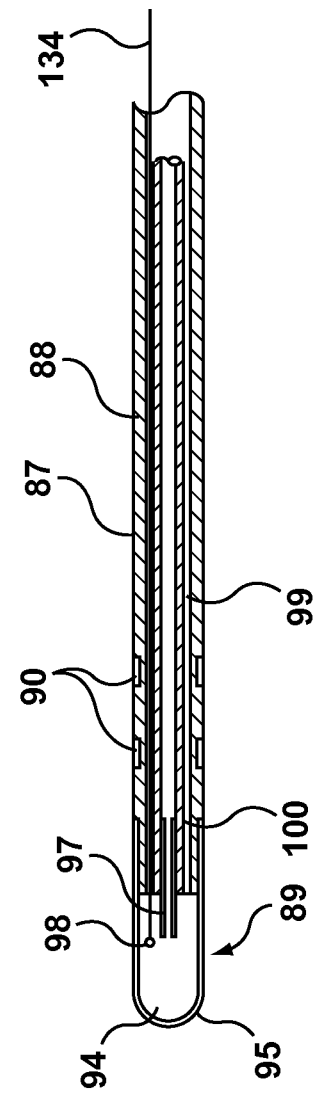

FIG. 15A depicts in simplified schematic form an Endovascular Transmural Cryo Ablation (ETCA) catheter 87. FIG. 15B depicts in cross section view ETCA catheter 87. ETCA catheter 87 comprises cryo-ablation element 89, catheter shaft 88, proximal terminal 91, and optional neural modulation electrodes 90. Proximal terminal 91 comprises electrical connector 93, cryogen supply connector 92, and cryogen gas return connector 105. Alternatively, a cryogen gas return connector may be omitted and cryogen gas may be exhausted to atmosphere. Cryo-ablation element 89 comprises cryo cap 95, optional capillary tube 97, and temperature sensor 98. Cryo cap 95 may be a thin walled metallic structure with high thermal conductivity. Capillary tube 97 is configured to meter the flow of cryogen from cryogen supply tube 100 into expansion/evaporation chamber 94 at a determined rate. Optionally a capillary tube may be omitted if a cryogen supply tube 100 and exhaust lumen 99 are sized appropriately. Capillary tube 97 may be fabricated for example from a stainless steel hypodermic tube or a polymer such as polyimide. Temperature sensor 98 may be positioned in expansion chamber 94, for example in contact with an inner wall of the cryo cap 95. Cryogen supply tube 100 may be bonded by adhesive to capillary tube 97 as shown. Cryo-ablation element 89 may be bonded to the distal end of catheter shaft 87. Catheter shaft 87 may be fabricated from a polymer such as Pebax or polyurethane, with an outer diameter between 5 French and 12 French. The working length of catheter 87 is between 90 cm and 140 cm. Cryogen supply tube 100 is configured for delivery of a cryogen under high pressure on the order of 100 psi to 2000 psi. Cryogen supply tube 100 may be fabricated from a polymer, or from a superelastic metal alloy such as Nitinol. Cryogen supply tube 100 is in fluidic communication with cryogen connector 92. Exhaust lumen 99 may be in fluidic communication with cryogen gas return connector 105 or be exhausted to atmosphere. Electrical cable 134 may connect temperature sensor 98, or neural modulation electrodes 90 to electrical connector 93.

FIG. 16A depicts the distal end of ETCA catheter 87 in working configuration with steerable carotid access sheath 1. FIG. 16B depicts an alternate embodiment of ETCA catheter 102 with steering capability comprising a user deflectable segment 103 and a non-deflectable segment 104 proximal to deflectable segment 103. Deflectable segment 103 may be actuated by a pull wire, and a deflection actuator disposed on a handle of proximal terminal, not shown. An ice ball 27 is depicted to represent a cryo-ablation functional modality.

Figure 17:
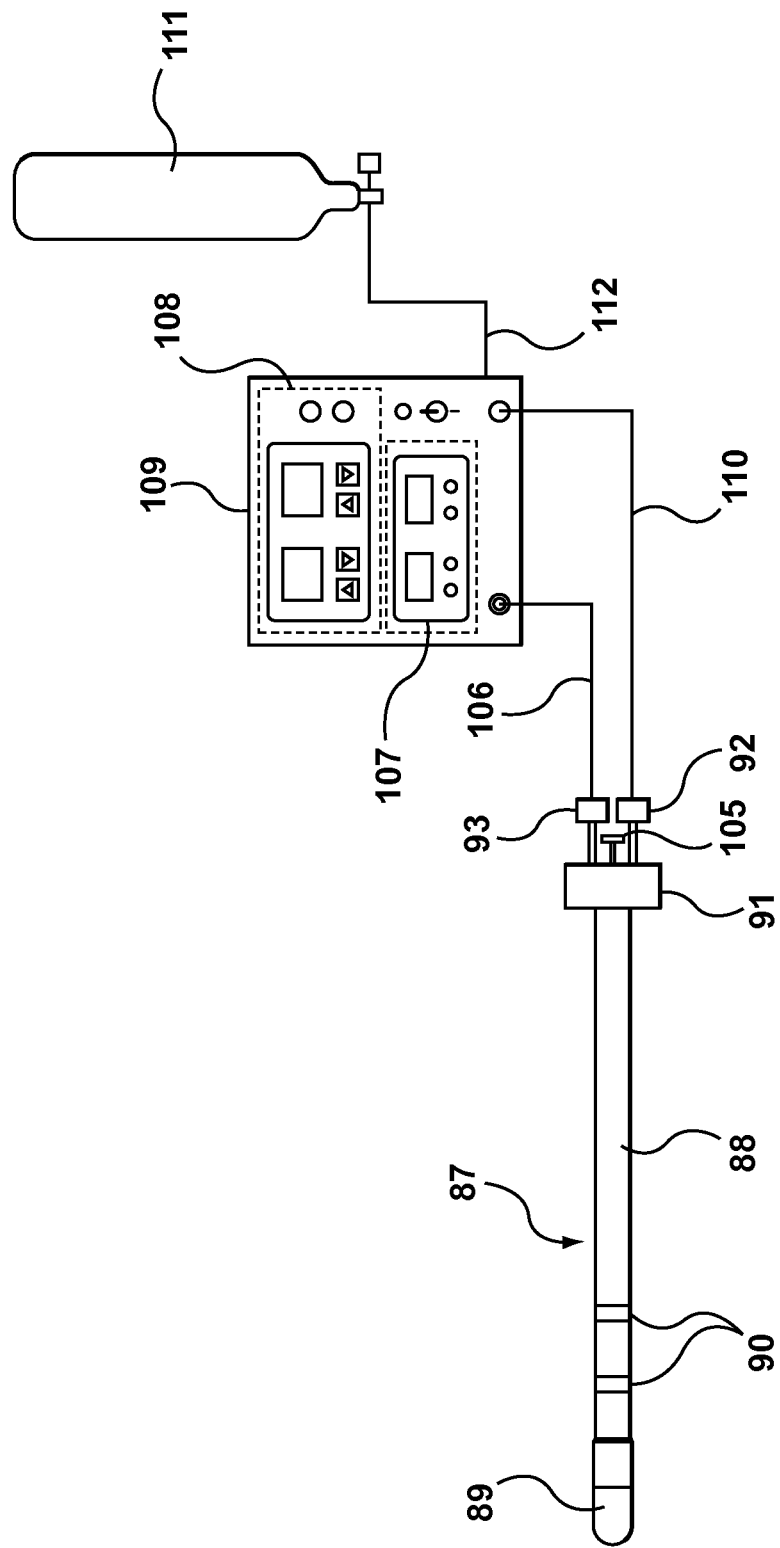
FIG. 17 is a schematic view of an endovascular ablation catheter having a point-ablate cryogenic ablation element.

FIG. 17 depicts in simplified schematic form an ETCA system. The ETCA system comprises ETCA catheter 87, control console 109, cryogen source 111, electrical umbilical 106, cryogen umbilical 110, and cryogen supply line 112. Control console 109 may have a user interface 108 that provides the user with a means to select cryo-ablation parameters, activate and deactivate a cryo-ablation, and to monitor the progress of a cryo-ablation. In addition, control console 109 may have second user interface 107 that allows the user to select electrical neuro-modulation parameters, activate neuro-modulation, deactivate neuro-modulation, and to monitor neuro-modulation. Control console 109 comprises a means to control the flow of cryogen from cryogen source 111 to ETCA catheter 87 according to user settings of user interface 108. Referring to FIG. 15A and FIG. 15B, an example of operation of an ETCA system may involve the following steps: ETCA ablation element 89 receives cryogen under high pressure from cryogen source 111 via control console 109, cryogen umbilical 110, cryogen connector 92, and cryogen supply tube 100. Cryogen under high pressure enters expansion/evaporation chamber 94 where a lower pressure allows the cryogen to change phase from a substantially liquid state to a substantially gas state resulting in a drop in temperature, which is dependent on the cryogen used, pressure and temperature of the cryogen prior to expansion/evaporation, and expansion/evaporation pressure. Temperature sensor 98 may be used by the control console 109 to control the flow the cryogen from control console 109 to ETCA catheter 87 by means of flow or pressure modulation, or the flow of cryogen gas out of the exhaust lumen 99, which would affect the pressure in the expansion chamber and thus the temperature of cryogen at phase change. Alternatively and optionally temperature sensor 98 may be used to determine that the ETCA system is working properly, or to determine following cryo-ablation if temperature has risen enough for tissue to thaw and cryo-adhesion to be released. The cryogen exits expansion chamber 94 into exhaust lumen 99 and out cryogen return gas connector 105 or released to atmosphere.

Cryogen may be supplied to cryo-ablation element 89 in the form of a fluid that is substantially liquid such liquid nitrogen, liquid carbon dioxide, or liquid nitrous oxide resulting in an endothermic phase change or an evaporative cooling process. Alternatively, a cryogen may be supplied to cryo-ablation element 89 in the form of a gas such as argon, nitrous oxide, nitrogen, or carbon dioxide where the cooling process is by Joule-Thomson effect, which is an adiabatic expansion. The surface temperature of cryo-ablation element 89 may be controlled by control console 109 at a temperature between zero degrees centigrade and −120 degrees centigrade during ablation by controlling the flow rate, or temperature of the cryogen or pressure in the expansion chamber. The system described may also be configured for use with an Endovascular Transmural Cryo Ablation catheter described above, or with a Percutaneous Cryo Ablation Probe described below.

Figure 18:
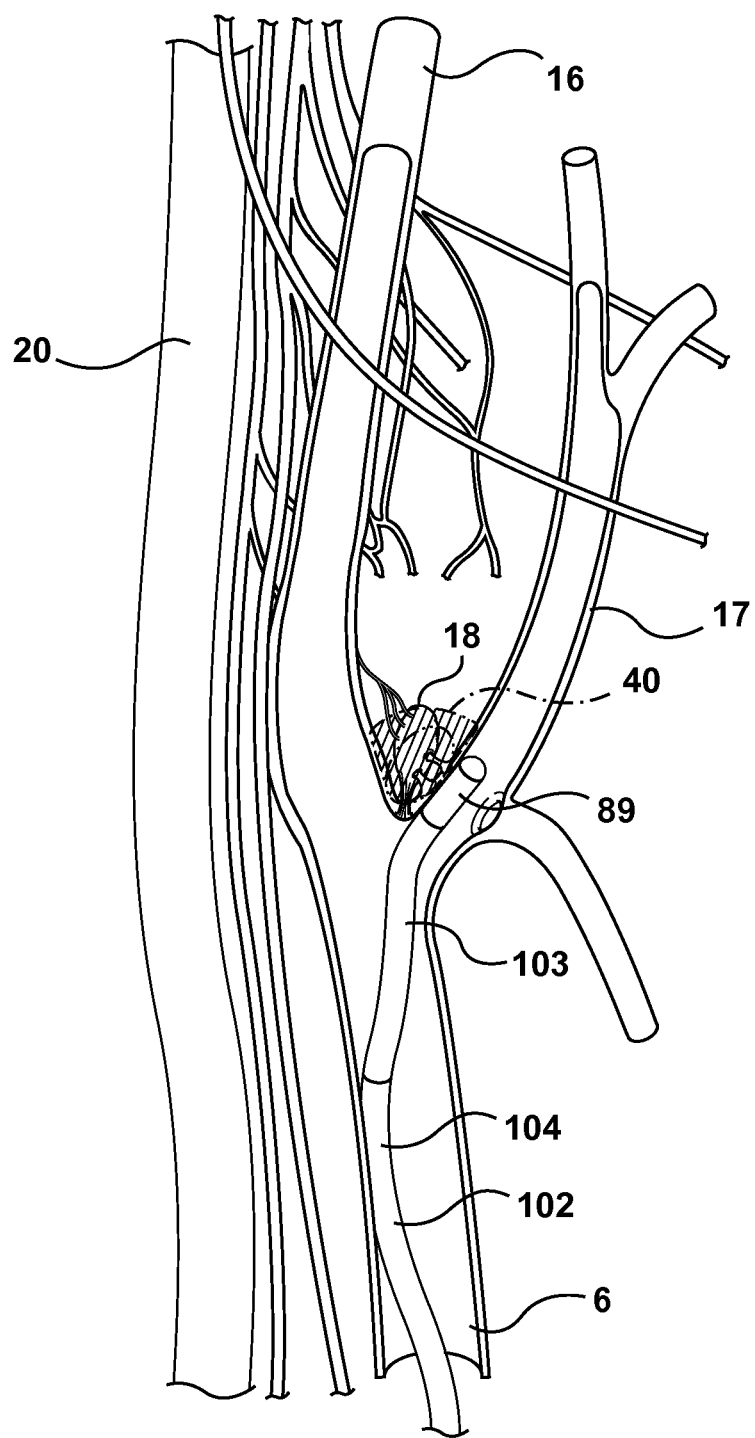
FIG. 18 is a cutaway illustration of a lateral view a patient's right carotid artery system with a schematic view of an endovascular ablation catheter having a point-ablate cryogenic ablation element, contained in a sheath, showing an ice ball formed around the cryogenic ablation element.

FIG. 18 depicts a steerable configuration of ETCA catheter 102 in position for ablation of carotid body 18 immediately following an ablation with a zone of frozen tissue 40 depicted. As depicted cryo-ablation element 89 has been positioned against a wall of external carotid artery 17 proximate to carotid body 18 by a user using fluoroscopic guidance and the steering capability of ETCA catheter 102 comprising deflectable distal segment 103, and non-deflectable segment 104. ETCA catheter 102 may also be positioned within the internal carotid artery 16, and alternately the internal jugular vein 20 for transmural cryo-ablation of carotid body 18, not shown.

Figures 19A, 19B, 19C:
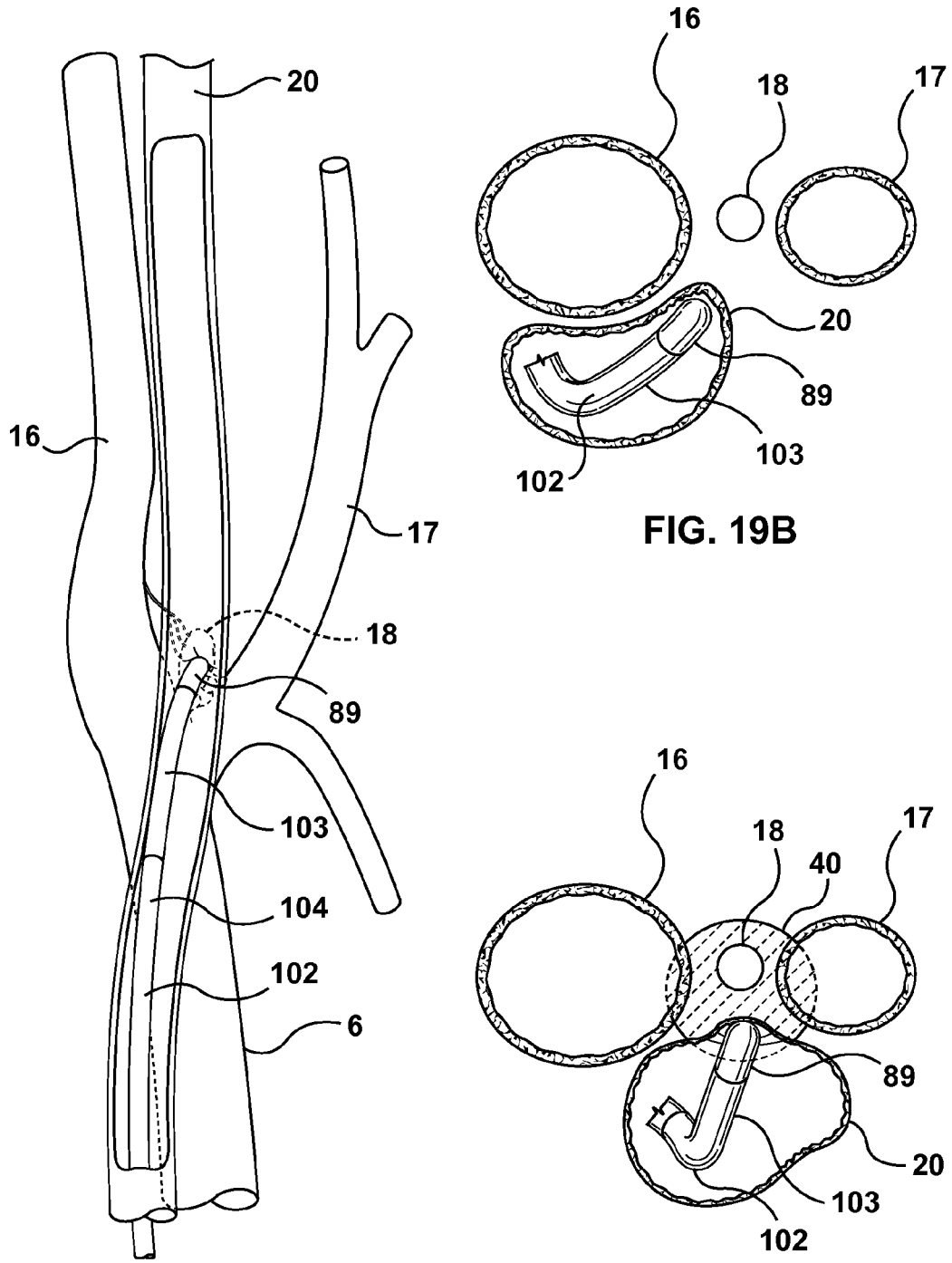
FIG. 19A is a cutaway illustration of a lateral view of a patient's right internal jugular vein with a schematic view of an endovascular cryo-ablation catheter positioned for transmural cryo-ablation of a carotid body from within the jugular vein.
FIG. 19B is a cross sectional view of a patient's internal and external carotid arteries, carotid body and internal jugular vein with an endovascular cryo-ablation catheter positioned for transmural cryo-ablation of a carotid body from within the jugular vein where the deflectable segment of the endovascular cryo-ablation catheter is used to deform the jugular vein in order to position the cryo-ablation element in close proximity to the carotid body.
FIG. 19C depicts a cryo-ablation of the carotid body.

FIG. 19A depicts the use of a steerable ETCA catheter 102 in an internal jugular vein 20 for ablation of carotid body 18. ETCA catheter 102 is inserted into a peripheral vein such as the clavicle vein or femoral vein, not shown, and then navigated into the internal jugular vein with cryo-ablation 89 positioned at the level of the carotid body, as shown using standard fluoroscopic guidance or other visual guidance technology. Alternatively, direct puncture of jugular vein in the neck can be used to gain access to the desired location near a carotid artery bifurcation. For example, over the wire ultrasound-guided right internal jugular vein access is well known in anesthesiology, hemodynamic monitoring or endomyocardial biopsy. FIG. 19B depicts the manipulation of the wall of the internal jugular vein with the steering function of ETCA catheter 102 to position cryo-ablation element 89 in close proximity to carotid body 18. It is noted here that the internal jugular vein 20 is a mobile and elastic structure and may be manipulated by ETCA catheter 102 to position cryo-ablation element 89 in close proximity to carotid body 18. FIG. 19C depicts a cryo-ablation of carotid body 18 with frozen tissue 40 encompassing carotid body 18. The procedure of maneuvering and steering the cryo-ablation element 89 in close proximity to target can be assisted by an external ultrasound that can be multiple plane ultrasound and may have Doppler capability to identify the carotid bifurcation by high velocity of blood stream.

Figure 20:
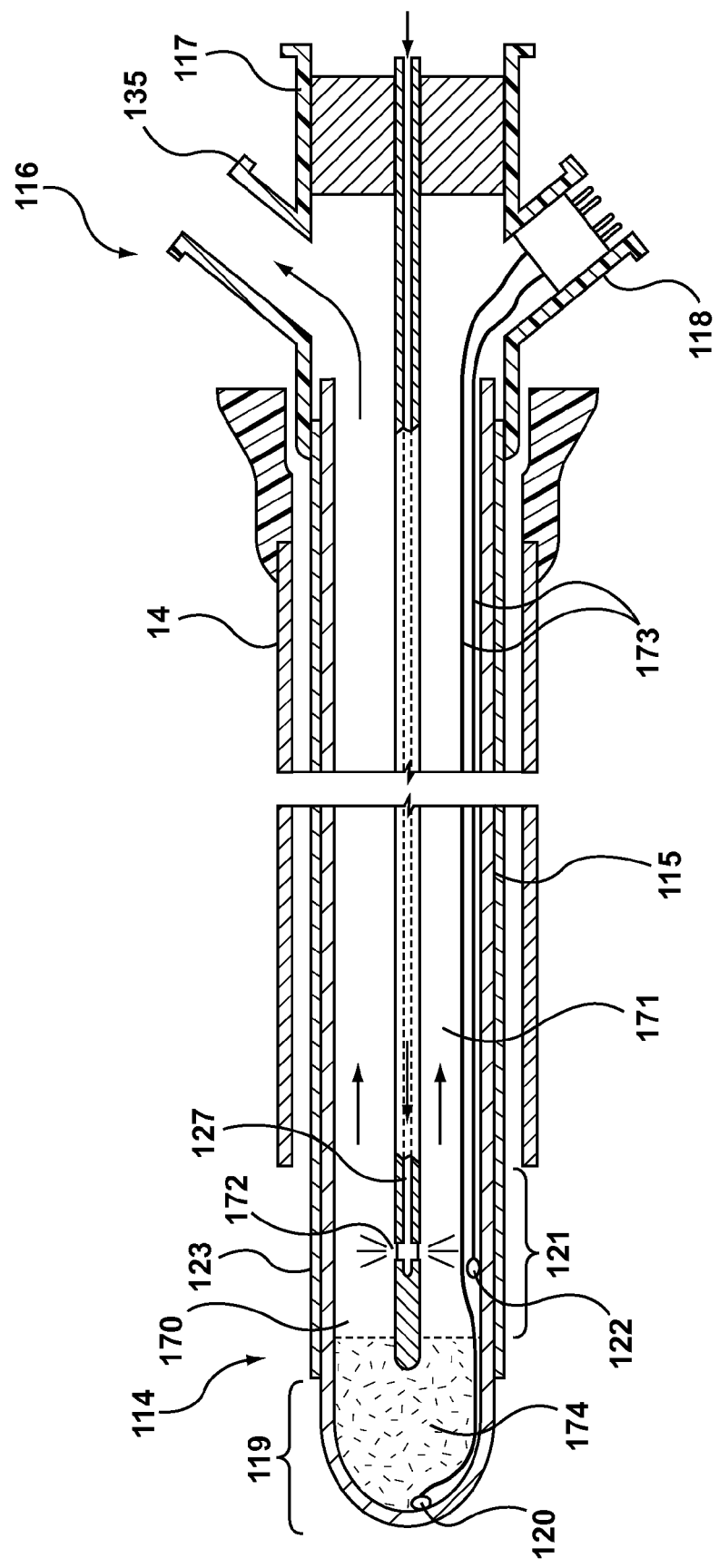
FIG. 20 depicts a percutaneous cryo-ablation probe with a warming element at the distal tip.

FIG. 20 depicts a Two Zone Percutaneous Cryo Ablation probe (TZPCA) 114. TZPCA probe 114 is configured to cryo-ablate a carotid body by percutaneous access, and to protect nervous structures from cold injury distal to the tip of the probe using a distal warming means. For example, a distal warming means may protect tissue from cold injury by maintaining tissue temperature above about 0° C. (e.g., above about 10° C.) and below a temperature that may cause thermal injury (e.g., below about 50° C.). TZPCA probe 114 is an elongated structure comprising a shaft 115, a distal region comprising warming element 119, and proximal to warming element 119 cryo-ablation element 121, and a proximal terminal 116, which may comprise cryogen supply connector 117, electrical connector 118, and cryogen return gas connector 135 (alternatively, cryogen return gas connector may be omitted and gas may be exhausted to atmosphere). Shaft 115 may be a rigid metallic structure fabricated from a stainless steel hypo tube or rigid polymer, or may be a hollow flexible structure fabricated from a polymer. Shaft 115 has a caliber suitable for insertion though a percutaneous cannula 14 with an outer diameter between 1 mm and 2 mm, and a length between 5 cm and 15 cm long (e.g., between about 8 cm and 10 cm long). As depicted, shaft 115 is a stainless steel hypotube with a rounded distal tip. The cryo-ablation element 121 may comprise an expansion/evaporation chamber 170, a temperature sensor 122, and a cryogen supply tube 127 in communication with cryogen supply connector 117 with cryogen gas exhausting the probe through an exhaust lumen 171 which may be connected to return cryogen gas connector 135 or exhausted to atmosphere. Cryogen supply tube 127 may have exit lumens 172 that allow cryogen to escape the supply lumen 127 into the expansion chamber 170 directed toward the sides of the inner wall of the cryo-ablation element 121. Warming element 119 may be formed by configuring the distal tip as an RF warming electrode. A thermally insulative material such as silicone 174 may be positioned between the cryo-ablation element and the warming element to reduce thermal conduction. The warming element electrode may be formed by coating shaft 115 with an electrically insulative coating 123 (e.g., PET, or Polyimide) except at the distal tip as shown, and electrically connecting shaft 115 to a source of heating that can be RF energy or other source of controllable heat. If RF energy is used to warm tissue proximate the warming element 119 a dispersive electrode may be placed on a patient's skin to complete the RF circuit. In addition, a temperature sensor 120 is mounted in thermal association with the uncoated warming element electrode 119. Shaft 115, cryo-ablation temperature 122, and warming element temperature sensor 120 are connected to electrical connector 118 by wires 173 running though a channel of shaft 115 and proximal terminal 116. The distal heating element may be configured to heat by alternate energy means including ultrasonic, laser, microwave energy, or by a resistive heating element.

Figure 21:
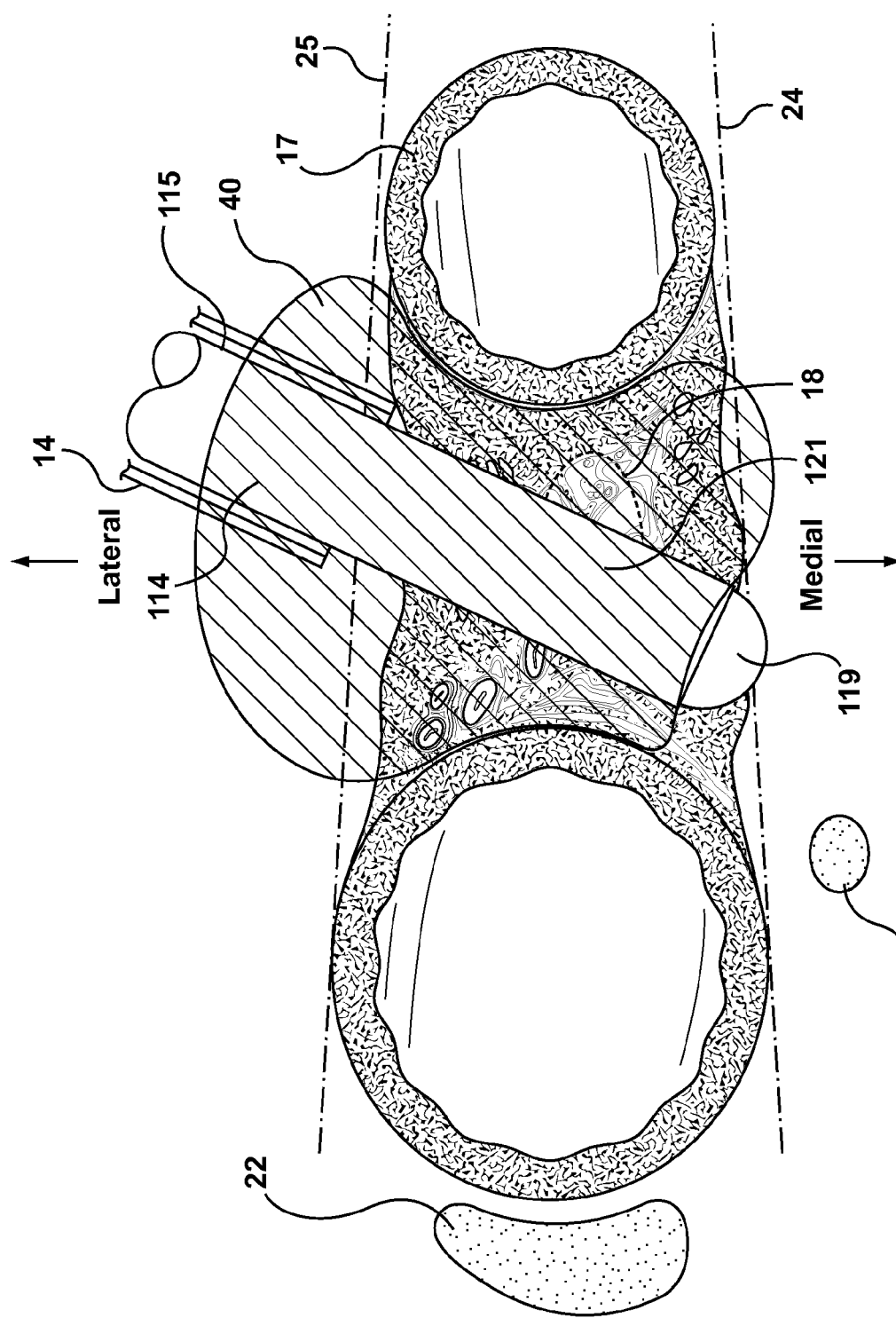
FIG. 21 depicts a sectional view of percutaneous cryo-ablation probe in position for carotid body cryo-ablation illustrating sympathetic nerve protection using the probe's distal warming feature.

FIG. 21 is a sectional view of a TZPCA probe during a cryo-ablation, where a warming element 119 is protecting sympathetic nerve 23 and other vulnerable structures medial of carotid septum from cold injury by preventing frozen tissue 40 from expanding in the distal direction. For example, frozen tissue 40 may be cooled to a cryo-ablative temperature (e.g., 40° C. or lower) while the warming element may prevent cryo-ablative temperature from spreading in a distal direction. The warming element may allow tissue distal to the cryo-ablation element to remain in a temperature range that does not cause thermal injury, for example, above −40° C. (e.g., above −20° C., or above 0° C., or above 10° C.) and below about 50° C. (e.g., below about 45° C.).

Figure 22:
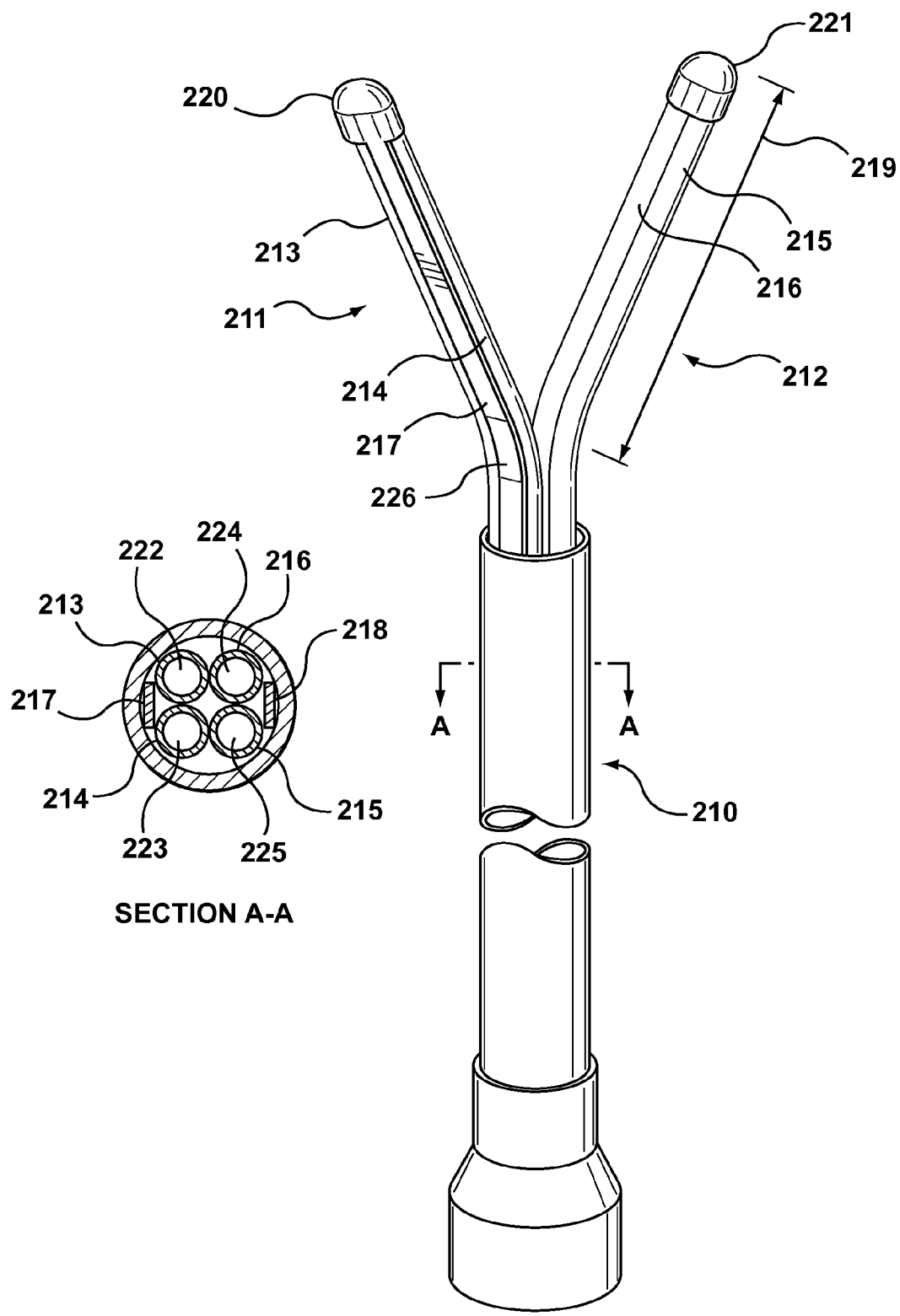
FIG. 22 depicts a schematic view of a cryo-ablation catheter having deployable arms that carry near critical cryogen.

FIG. 22 is a schematic view of a cryo ablation catheter 210 having a first deployable arm 211 and a second deployable arm 212 for positioning along the internal 16 and external 17 carotid artery sides of an intercarotid septum 140. The arms 211 and 212 carry a cryogen fluid, such as nitrogen, argon, neon, or helium, maintained at near critical pressure and temperature. Near critical temperature and pressure is at a temperature and pressure within about 10% of the liquid-vapor critical point, which has a viscosity similar to gas yet a density and thermal capacity similar to liquid making it a very efficient coolant. The arms deploy substantially into a V-shape for bifurcation apposition. Arm length 219 allows them to contact both sides of the intercarotid septum 140 and pull heat from tissue of the septum thus cryogenically ablating the septum. For example, arm length 219 may be between about 5 mm and 20 mm long (e.g., about 15 mm). Arm length 219 is the distance from a location at which the arm initially extends away from the axis of the catheter to a distal end of the arm. At least one arm length 219 can be between about 2.5 mm and about 20 mm. At least one arm length 219 can be between about 2.5 mm and about 15 mm. At least one arm length 219 can be between about 2.5 mm and about 10 mm. At least one arm length 219 can be between about 5 mm and about 15 mm. At least one arm length 219 can be between about 5 mm and about 10 mm. At least one arm length 219 can be between about 10 mm and about 20 mm. At least one arm length 219 can be between about 10 mm and about 15 mm. At least one arm length 219 can be between about 15 mm and about 20 mm. The first arm 211 comprises a cryogen delivery tube 213 and a cryogen return tube 214 connected at a distal end with an end cap 220. A lumen 222 in delivery tube 213 is in fluid communication through end cap 220 with a lumen 223 in return tube 214. The delivery tube 213 and return tube 214 travel a length of catheter 210 to a proximal end terminating in a fluid connector. Likewise, the second arm 212 has similar components as the first arm 211, including a cryogen delivery tube 215 with a lumen 225 in fluid communication through an end cap 221 with a lumen 224 in a cryogen return tube 216. The cryogen delivery and return tubes may be made from a material that maintains flexibility and strength in a range of temperature from about −200 degrees Celsius to +50 degrees Celsius. Superelastic arms 217 and 218 have a preformed bend 226 and 227 that cause the arms to deploy into a V-shape when a delivery sheath 1 is retracted. For example, the arms may bend away from an axis of catheter 210 at an angle of about 30 to 60 degrees (e.g., about 45 degrees). The superelastic arms 217 and 218 and end caps 220 and 221 may be made from Nitinol and may have a radiopaque coating added to enhance visualization on fluoroscopy. Near critical cryogen fluid may be supplied to the catheter 210 by a pump as is known in the art.

Figure 23:
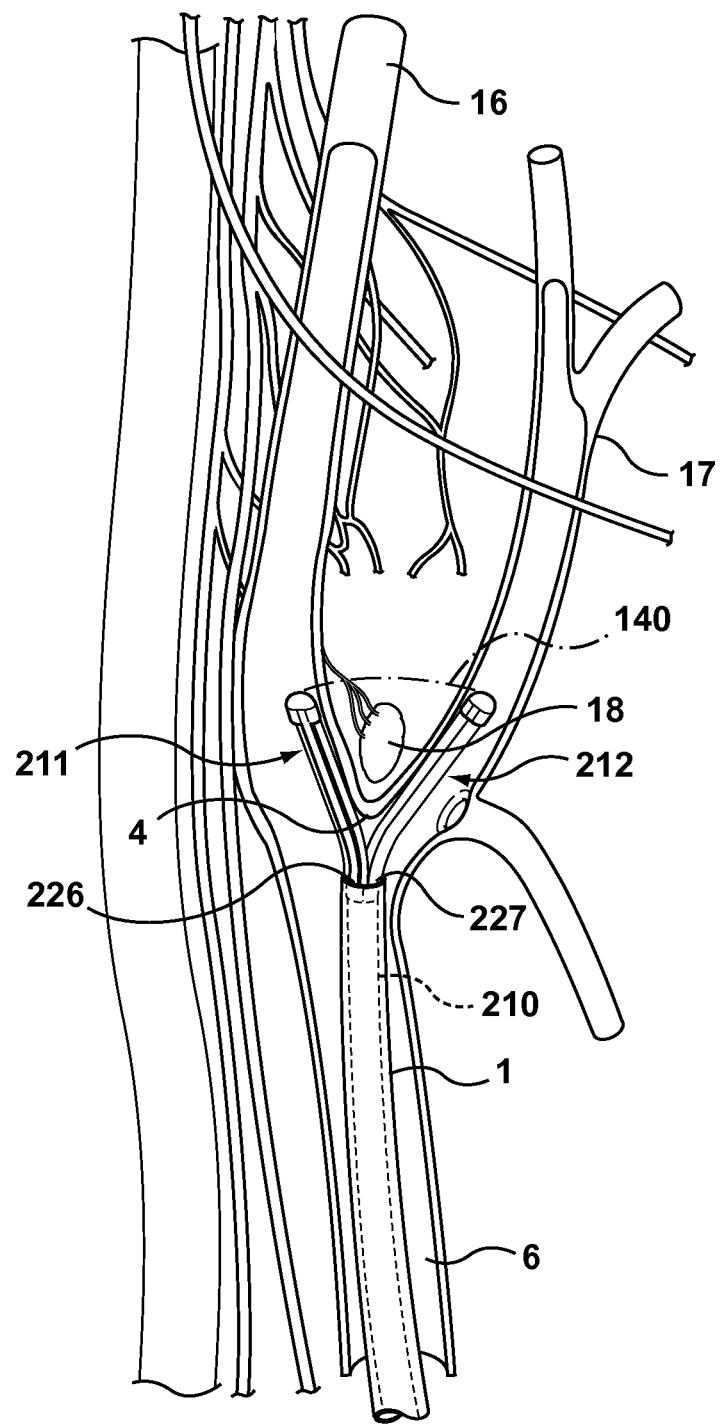
FIG. 23 is a cutaway illustration of a lateral view of a patient's right carotid artery system with a schematic view of cryo ablation catheter delivered through a delivery sheath and positioned at a patient's intercarotid septum.

FIG. 23 is a cutaway illustration of a lateral view of a patient's right carotid artery system with a schematic view of cryo ablation catheter 210 delivered through a delivery sheath 1 and positioned at a patient's intercarotid septum 140. The catheter 210 may be delivered within the sheath 1 to a patient's common carotid artery 6 in a constrained state. Then the sheath 1 may be retracted exposing the arms and bends 226 and 227 so the preformed superelastic material causes the arms to deploy into an open V-shape. The arms may be advanced under fluoroscopic guidance into contact with carotid bifurcation 4. Optionally, the sheath 1 may be advanced over the bends to close the V-shape of the arms until they contact vessel walls of the intercarotid septum. Once in contact cryogen may be delivered through the catheter 210 to cryo ablate the septum.

Figure 24:
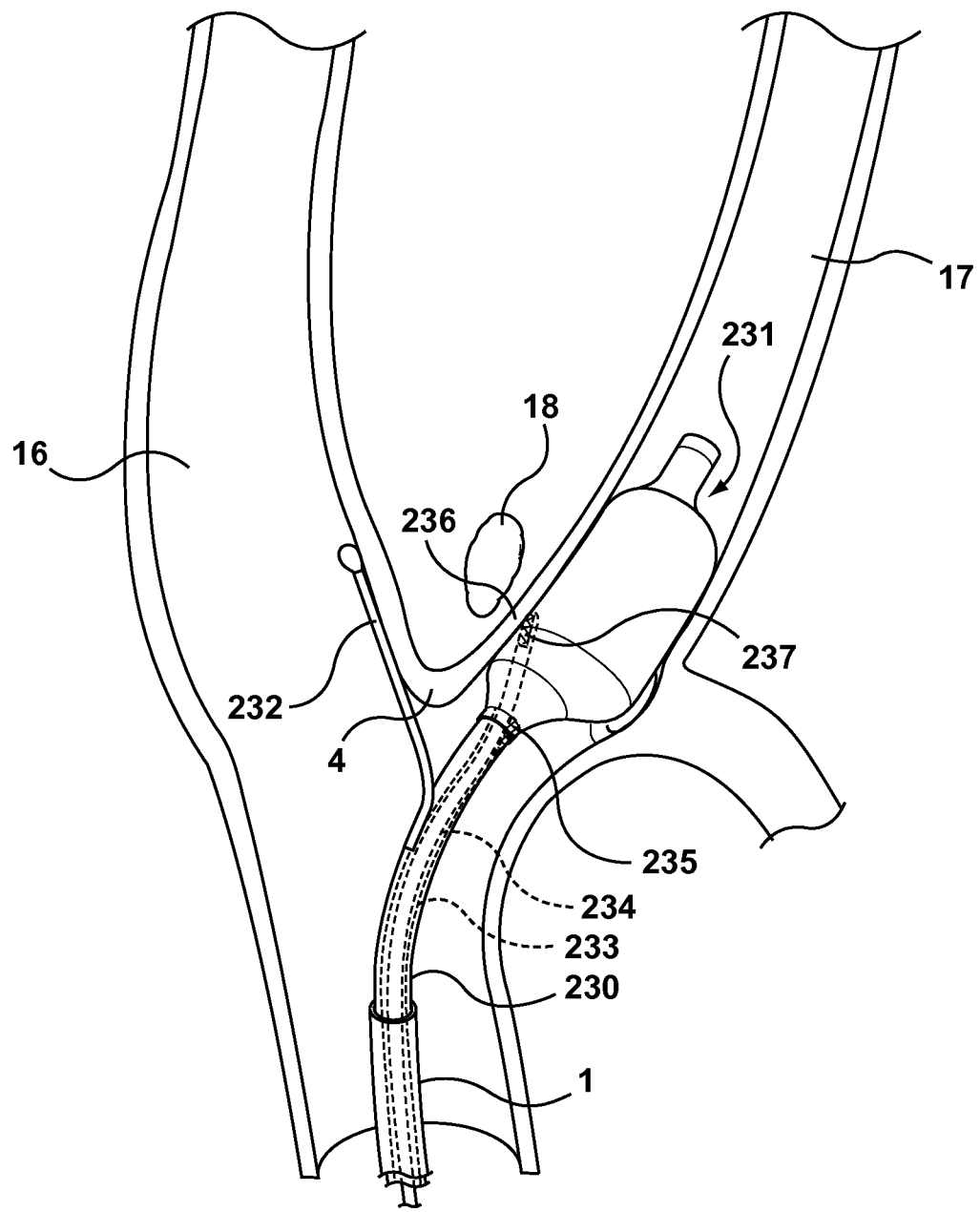
FIG. 24 is a schematic illustration of a cryo-ablation catheter delivered through a balloon catheter that couples with a carotid bifurcation.

A system including a delivery sheath 1 for delivering a balloon catheter 230 to the site of a carotid body is shown in FIG. 24. The balloon catheter comprises a distal balloon 231 and a carotid bifurcation-coupling member 232. The balloon catheter may have a lumen 233 through which a cryo-ablation catheter 234 is passed. The balloon 231 may be inflated with low pressure in the external carotid artery 17. Then the cryo-ablation catheter 234 may be advanced through the lumen 233 into the balloon 231. A deflection means such as an angled hole 235 may direct the cryo-ablation catheter 234 towards a side of the balloon. The area where the cryo-ablation element 237 contacts the wall of the balloon may be referred to as the ablation element contact zone 236. The balloon 231 functions to stabilize the catheter in the vessel and also to reduce or stop blood flow around the cryo-ablation element 237, thus reducing a heat sink from the blood and allowing the cryo-ablation element 237 to create a sufficiently large ablation in a carotid septum 140. The balloon may be semi-compliant or non-compliant and be symmetrical, or be asymmetric to bring the shaft and lumen 233 closer to the ablation site. The balloon catheter may contain radiopaque markers to facilitate visualization and placement. The cryo-ablation catheter 234 may contain a controllable deflection means that assists in positioning the ablation element 237. The balloon 231 may be positioned at a carotid bifurcation 4 such that the proximal end of the balloon is positioned at the bifurcation and the distal end of the balloon is positioned about 15 mm beyond the bifurcation. This ensures the cryo-ablation element is positioned an appropriate height from the bifurcation. The ablation element 237 may be free to move anywhere along the inner balloon wall, or it may be restricted to contact only a side of the balloon wall that is facing the bifurcation coupling member 232. The ablation element 237 may be in the range of 3 to 5 French and of a length between 2 and 5 mm. The ablation element may be a material of high thermal conductivity such as copper, nickel, or stainless steel. The cryo-ablation catheter may utilize a cooling technique such as liquid evaporation (e.g., $N_2O$) or near critical fluid circulation (e.g., $N_2$). In either case the balloon catheter 230 and delivery sheath 1 will provide insulation protection along the length of the catheter shaft.

Figure 25:
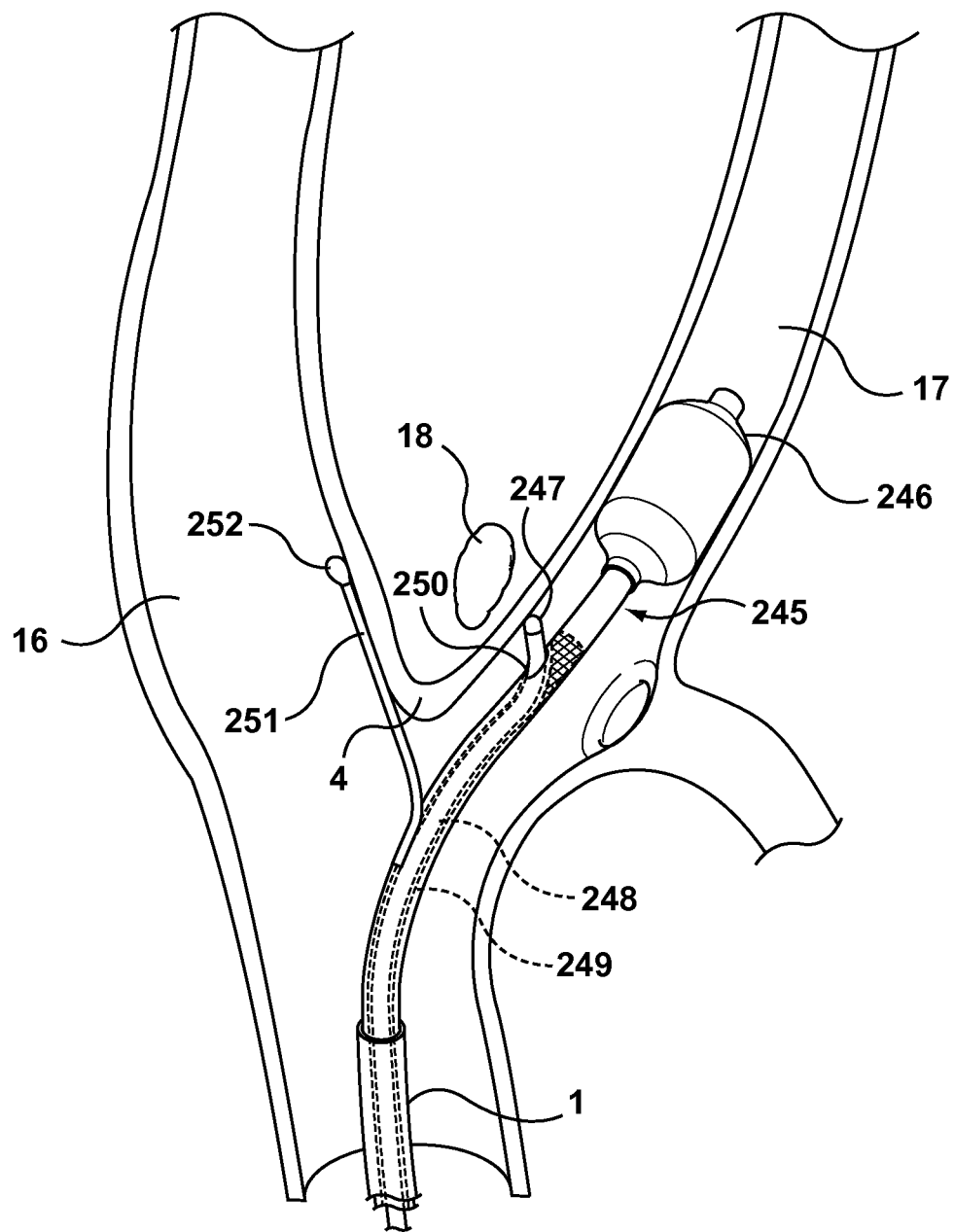
FIG. 25 is a schematic illustration of a cryo-ablation catheter delivered through a balloon catheter that couples with a carotid bifurcation.

As shown in FIG. 25, a balloon catheter 245 may be configured to place an occluding balloon 246 distal to a cryo-ablation element 247 in an external carotid artery 17 to occlude blood flow and reduce the heat sink tendency of flowing blood to allow the cryo-ablation element 247 to create a sufficiently large ablation. In this embodiment the cryo-ablation catheter 248 is advanced through a lumen 249 in the balloon catheter 245 and deployed from the lumen through an exit port 250 in the side of the balloon catheter directed toward a bifurcation-coupling member 251 at a desired height from the coupling member (e.g., 4 to 10 mm distal from the coupling member).

The carotid bifurcation coupling member 251 may be an arm with an elastic member having a preformed shape such that when the distal region of the catheter is advanced out of a delivery sheath 1 the member 251 deploys. The preformed shape may comprise a bend so the member deploys at an angle of about 30 to 50 degrees from the catheter shaft. The member 251 may have a soft, rounded tip 252 to reduce risk of vessel trauma or plaque dislodgement. Alternatively, a bifurcation coupling member may be a guidewire passed through a lumen in the catheter and out of a side port near a distal end of the catheter (not shown). The position at which the bifurcation coupling member 251 diverges from the catheter 245 may be about 4 to 20 mm proximal to the exit port 250. This arrangement allows a user to advance the catheter 245 from a delivery sheath 1, rotate the catheter to aim the bifurcation coupling member 251 at an internal carotid artery 16 and the balloon 246 at an external carotid artery 17, then advance the catheter 245 to couple the diverging member 251 with the carotid bifurcation 4, and the ablation element contact zone would be placed at an ideal distance from the carotid bifurcation and rotational position in the artery to target a carotid body or its associated nerves.

Methods of Therapy:

There may be danger of creating a brain embolism while performing an endovascular procedure in a patient's carotid artery, for example, a thrombus may be created by delivering ablation energy, or a piece of atheromatous plaque may be dislodged by catheter movement. In addition to a carotid body ablation catheter, an endovascular catheter may be used to place a brain embolism protection device in a patient's internal carotid artery during a carotid body ablation procedure. The treatment may include occluding a patient's internal carotid artery. Blood flowing from a common carotid artery 59 would not flow through a connecting internal carotid artery 30, which feeds the brain, but instead would flow through the external carotid artery 29, which feeds other structures of the head that are much more capable of safely receiving an embolism. For example, a brain embolism protection device in the form of an inflatable balloon is placed in an internal carotid artery. The balloon may be made from a soft, stretchable, compliant balloon material such as silicone and may be inflated with a fluid (e.g., saline or contrast agent) through an inflation lumen. The inflation fluid may be injected into an inlet port by a syringe or by a computer controlled pump system. The balloon may be placed, using a delivery sheath, in an internal carotid artery (e.g., up to about 10 cm from a carotid bifurcation). Contrast solution may be injected into the common carotid artery, for example through the delivery sheath to allow radiographic visualization of the common, internal and external carotid arteries, which may assist a physician to position a brain embolism protection device. An endovascular ablation catheter may place an energy delivery element proximate a carotid body, for example at a carotid septum. It is expected that blood flow would carry any debris into the external carotid artery where it is harmless. Occlusion of an internal carotid artery may be done for a period of time that allows an ablation procedure and that is safe for the brain (e.g., less than or equal to about 3 minutes, or between about 1 to 2 minutes). After the carotid body is ablated the brain embolism protection device may be deployed and removed from the patient or positioned on the patient's contralateral side in the event of ablating the contralateral carotid body.

In another embodiment a brain embolism protection device may be a blood-permeable filter deployed in a patient's internal carotid artery. A filter may be a fine mesh or net connected to a deployable frame that expands to envelop a cross-section of an internal carotid artery distal to a bifurcation. Other embodiments of a blood-permeable filter may include wire-type expandable devices such as baskets or umbrellas. Such a filter may allow antegrade blood flow to continue to the brain while trapping and retrieving debris in the blood, preventing a brain embolism. Such a device may be deployed in an internal carotid artery prior to the placement of ablation catheter and retrieved following ablation.

A cryogen source and optionally a cryo-console may be located external to the patient. The console may include computer controls to automatically or manually adjust parameters such as cryogen flow rate, temperature, back pressure, or pressure in an expansion chamber, as well as timing and period during which cryogenic energy is applied, and safety limits to the application of energy. A console may also provide an indication (e.g., a timer countdown) of cryogenic exposure duration or temperature that may result in temporary nerve blockage, or an indication of cryogenic exposure duration or temperature that may result in permanent ablation. It should be understood that embodiments of cryo-devices described herein may be electrically and fluidically connected to the generator even though the generator is not explicitly shown or described with each embodiment.

An ablated tissue lesion at or near the carotid body may be created by the application of cryogenic energy from a cryo-element proximate to a distal end of a carotid body ablation device. The ablated tissue lesion may disable the carotid body or may suppress the activity of the carotid body or interrupt conduction of afferent nerve signals from a carotid body to sympathetic nervous system. The disabling or suppression of the carotid body reduces the responsiveness of the glomus cells to changes of blood gas composition and effectively reduces activity of afferent carotid body nerves or the chemoreflex gain of the patient.

A method in accordance with a particular embodiment includes ablating at least one of a patient's carotid bodies based at least in part on identifying the patient as having a sympathetically mediated disease such as cardiac, metabolic, or pulmonary disease such as hypertension, insulin resistance, diabetes, pulmonary hypertension, drug resistant hypertension (e.g., refractory hypertension), congestive heart failure (CHF), or dyspnea from heart failure or pulmonary disease causes.

A procedure may include diagnosis, selection based on diagnosis, further screening (e.g., baseline assessment of chemosensitivity), treating a patient based at least in part on diagnosis or further screening via a chemoreceptor (e.g., carotid body) ablation procedure such as one of the embodiments disclosed. Additionally, following ablation a method of therapy may involve conducting a post-ablation assessment to compare with the baseline assessment and making decisions based on the assessment (e.g., adjustment of drug therapy, re-treat in new position or with different parameters, or ablate a second chemoreceptor if only one was previously ablated).

A carotid body ablation procedure may comprise the following steps or a combination thereof: patient sedation, locating a target peripheral chemoreceptor, visualizing a target peripheral chemoreceptor (e.g., carotid body), confirming a target ablation site is or is proximate a peripheral chemoreceptor, confirming a target ablation site is safely distant from vital structures that are preferably protected (e.g., hypoglossal and vagus nerves), providing stimulation (e.g., electrical, mechanical, chemical) to a target site or target peripheral chemoreceptor prior to, during or following an ablation step, monitoring physiological responses to said stimulation, providing temporary cryogenic nerve block to a target site prior to an ablation step, monitoring physiological responses to said temporary nerve block, anesthetizing a target site, protecting the brain from potential embolism, thermally protecting an arterial or venous wall (e.g., carotid artery, jugular vein) or a medial aspect of an intercarotid septum or vital nerve structures, cryo-ablating a target site or peripheral chemoreceptor, monitoring ablation parameters (e.g., temperature, pressure, duration, blood flow in a carotid artery), monitoring physiological responses during ablation and arresting ablation if unsafe or unwanted physiological responses occur before collateral nerve injury becomes permanent, confirming a reduction of chemoreceptor activity (e.g., chemosensitivity, HR, blood pressure, ventilation, sympathetic nerve activity) during or following an ablation step, removing a cryo-ablation device, conducting a post-ablation assessment, repeating any steps of the chemoreceptor ablation procedure on another peripheral chemoreceptor in the patient.

Patient screening, as well as post-ablation assessment may include physiological tests or gathering of information, for example, chemoreflex sensitivity, central sympathetic nerve activity, heart rate, heart rate variability, blood pressure, ventilation, production of hormones, peripheral vascular resistance, blood pH, blood PCO2, degree of hyperventilation, peak VO2, VE/VCO2 slope. Directly measured maximum oxygen uptake (more correctly pVO2 in heart failure patients) and index of respiratory efficiency VE/VCO2 slope has been shown to be a reproducible marker of exercise tolerance in heart failure and provide objective and additional information regarding a patient's clinical status and prognosis.

A method of therapy may include electrical stimulation of a target region, using a stimulation electrode, to confirm proximity to a carotid body. For example, a stimulation signal having a 1-10 milliamps (mA) pulse train at about 20 to 40 Hz with a pulse duration of 50 to 500 microseconds (μs) that produces a positive carotid body stimulation effect may indicate that the stimulation electrode is within sufficient proximity to the carotid body or nerves of the carotid body to effectively ablate it. A positive carotid body stimulation effect could be increased blood pressure, heart rate, or ventilation concomitant with application of the stimulation. These variables could be monitored, recorded, or displayed to help assess confirmation of proximity to a carotid body. A catheter-based technique, for example, may have a stimulation electrode proximal to the cryo-element used for ablation. Alternatively, the cryo-element itself may also be used as a stimulation electrode. Alternatively, a cryogenic ablation applicator, may be configured to also deliver an electrical stimulation signal as described earlier. Yet another alternative embodiment comprises a stimulation electrode that is distinct from an ablation element. For example, during a surgical procedure a stimulation probe can be touched to a suspected carotid body that is surgically exposed. A positive carotid body stimulation effect could confirm that the suspected structure is a carotid body and ablation can commence. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlates to a given stimulation the computerized generator may provide an indication of a positive confirmation.

Alternatively or in addition a drug known to excite the chemo sensitive cells of the carotid body can be injected directly into the carotid artery or given systemically into a patient's vein or artery in order to elicit hemodynamic or respiratory response. Examples of drugs that may excite a chemoreceptor include nicotine, atropine, Doxapram, Almitrine, hyperkalemia, Theophylline, adenosine, sulfides, Lobeline, Acetylcholine, ammonium chloride, methylamine, potassium chloride, anabasine, coniine, cytosine, acetaldehyde, acetyl ester and the ethyl ether of i-methylcholine, Succinylcholine, Piperidine, monophenol ester of homo-isomuscarine and acetylsalicylamides, alkaloids of veratrum, sodium citrate, adenosinetriphosphate, dinitrophenol, caffeine, theobromine, ethyl alcohol, ether, chloroform, phenyldiguanide, sparteine, coramine (nikethamide), metrazol (pentylenetetrazol), iodomethylate of dimethylaminomethylenedioxypropane, ethyltrimethylammoniumpropane, trimethylammonium, hydroxytryptamine, papaverine, neostigmine, acidity.

A method of therapy may further comprise applying electrical or chemical stimulation to the target area or systemically following ablation to confirm a successful ablation. Heart rate, blood pressure or ventilation may be monitored for change or compared to the reaction to stimulation prior to ablation to assess if the targeted carotid body was ablated. Post-ablation stimulation may be done with the same apparatus used to conduct the pre-ablation stimulation. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlated to a given stimulation is reduced following an ablation compared to a physiological response prior to the ablation, the computerized generator may provide an indication ablation efficacy or possible procedural suggestions such as repeating an ablation, adjusting ablation parameters, changing position, ablating another carotid body or chemosensor, or concluding the procedure.

Visualization:

An optional step of visualizing internal structures (e.g., carotid body or surrounding structures) may be accomplished using one or more non-invasive imaging modalities, for example fluoroscopy, radiography, arteriography, computer tomography (CT), computer tomography angiography with contrast (CTA), magnetic resonance imaging (MRI), or sonography, or minimally invasive techniques (e.g., IVUS, endoscopy, optical coherence tomography, ICE). A visualization step may be performed as part of a patient assessment, prior to an ablation procedure to assess risks and location of anatomical structures, during an ablation procedure to help guide an ablation device, or following an ablation procedure to assess outcome (e.g., efficacy of the ablation). Visualization may be used to: (a) locate a carotid body, (b) locate vital structures that may be adversely affected, or (c) locate, identify and measure arterial plaque.

Endovascular (for example transfemoral) arteriography of the common carotid and then selective arteriography of the internal and external carotids may be used to determine a position of a catheter tip at a carotid bifurcation. Additionally, ostia of glomic arteries (these arteries may be up to 4 mm long and arise directly from the main parent artery) can be identified by dragging the dye injection catheter and releasing small amounts ("puffs") of dye. If a glomic artery is identified it can be cannulated by a guide wire and possibly further cannulated by small caliber catheter. Direct injection of dye into glomic arteries can further assist the interventionalist in the ablation procedure. It is appreciated that the feeding glomic arteries are small and microcatheters may be needed to cannulate them.

Alternatively, ultrasound visualization may allow a physician to see the carotid arteries and even the carotid body. Another method for visualization may consist of inserting a small needle (e.g., 22 Gauge) with sonography or computer tomography (CT) guidance into or toward the carotid body. A wire or needle can be left in place as a fiducial guide, or contrast can be injected into the carotid body. Runoff of contrast to the jugular vein may confirm that the target is achieved.

Computer Tomography (CT) and computer tomography angiography (CTA) may also be used to aid in identifying a carotid body. Such imaging could be used to help guide an ablation device to a carotid body.

Ultrasound visualization (e.g., sonography) is an ultrasound-based imaging technique used for visualizing subcutaneous body structures including blood vessels and surrounding tissues. Doppler ultrasound uses reflected ultrasound waves to identify and display blood flow through a vessel. Operators typically use a hand-held transducer/transceiver placed directly on a patient's skin and aimed inward directing ultrasound waves through the patient's tissue. Ultrasound may be used to visualize a patient's carotid body to help guide an ablation device. Ultrasound can be also used to identify atherosclerotic plaque in the carotid arteries and avoid disturbing and dislodging such plaque.

Visualization and navigation steps may comprise multiple imaging modalities (e.g., CT, fluoroscopy, ultrasound) superimposed digitally to use as a map for instrument positioning. Superimposing borders of great vessels such as carotid arteries can be done to combine images.

Responses to stimulation at different coordinate points can be stored digitally as a 3-dimensional or 2-dimensional orthogonal plane map. Such an electric map of the carotid bifurcation showing points, or point coordinates that are electrically excitable such as baroreceptors, baroreceptor nerves, chemoreceptors and chemoreceptor nerves can be superimposed with an image (e.g., CT, fluoroscopy, ultrasound) of vessels. This can be used to guide the procedure, and identify target areas and areas to avoid.

In addition, as noted above, it should be understood that a device providing therapy can also be used to locate a carotid body as well as to provide various stimuli (electrical, chemical, other) to test a baseline response of the carotid body chemoreflex (CBC) or carotid sinus baroreflex (CSB) and measure changes in these responses after therapy or a need for additional therapy to achieve the desired physiological and clinical effects.

Patient Selection and Assessment:

In an embodiment, a procedure may comprise assessing a patient to be a plausible candidate for carotid body ablation. Such assessment may involve diagnosing a patient with a sympathetically mediated disease (e.g., MSNA microneurography, measure of cataclomines in blood or urine, heart rate, or low/high frequency analysis of heart rate variability may be used to assess sympathetic tone). Patient assessment may further comprise other patient selection criteria, for example indices of high carotid body activity (i.e., carotid body hypersensitivity or hyperactivity) such as a combination of hyperventilation and hypocarbia at rest, high carotid body nerve activity (e.g., measured directly), incidence of periodic breathing, dyspnea, central sleep apnea elevated brain natriuretic peptide, low exercise capacity, having cardiac resynchronization therapy, atrial fibrillation, ejection fraction of the left ventricle, using beta blockers or ACE inhibitors.

Patient assessment may further involve selecting patients with high peripheral chemosensitivity (e.g., a respiratory response to hypoxia normalized to the desaturation of oxygen greater than or equal to about 0.7 l/min/min $SpO_2$), which may involve characterizing a patient's chemoreceptor sensitivity, reaction to temporarily blocking carotid body chemoreflex, or a combination thereof.

Although there are many ways to measure chemosensitivity they can be divided into (a) active provoked response and (b) passive monitoring. Active tests can be done by inducing intermittent hypoxia (such as by taking breaths of nitrogen or $CO_2$ or combination of gases) or by rebreathing air into and from a 4 to 10 liter bag. For example: a hypersensitive response to a short period of hypoxia measured by increase of respiration or heart rate may provide an indication for therapy. Ablation or significant reduction of such response could be indicative of a successful procedure. Also, electrical stimulation, drugs and chemicals (e.g., dopamine, lidocane) exist that can block or excite a carotid body when applied locally or intravenously.

The location and baseline function of the desired area of therapy (including the carotid and aortic chemoreceptors and baroreceptors and corresponding nerves) may be determined prior to therapy by application of stimuli to the carotid body or other organs that would result in an expected change in a physiological or clinical event such as an increase or decrease in SNS activity, heart rate or blood pressure. These stimuli may also be applied after the therapy to determine the effect of the therapy or to indicate the need for repeated application of therapy to achieve the desired physiological or clinical effect(s). The stimuli can be either electrical or chemical in nature and can be delivered via the same or another catheter or can be delivered separately (such as injection of a substance through a peripheral IV to affect the CBC that would be expected to cause a predicted physiological or clinical effect).

A baseline stimulation test may be performed to select patients that may benefit from a carotid body ablation procedure. For example, patients with a high peripheral chemosensitivity gain (e.g., greater than or equal to about two standard deviations above an age matched general population chemosensitivity, or alternatively above a threshold peripheral chemosensitivity to hypoxia of 0.5 or 0.7 ml/min % O2) may be selected for a carotid body ablation procedure. A prospective patient suffering from a cardiac, metabolic, or pulmonary disease (e.g., hypertension, CHF, diabetes) may be selected. The patient may then be tested to assess a baseline peripheral chemoreceptor sensitivity (e.g., minute ventilation, tidal volume, ventilator rate, heart rate, or other response to hypoxic or hypercapnic stimulus). Baseline peripheral chemosensitivity may be assessed using tests known in the art which involve inhalation of a gas mixture having reduced $O_2$ content (e.g., pure nitrogen, $CO_2$, helium, or breathable gas mixture with reduced amounts of $O_2$ and increased amounts of $CO_2$) or rebreathing of gas into a bag. Concurrently, the patient's minute ventilation or initial sympathetically mediated physiologic parameter such as minute ventilation or HR may be measured and compared to the $O_2$ level in the gas mixture. Tests like this may elucidate indices called chemoreceptor setpoint and gain. These indices are indicative of chemoreceptor sensitivity. If the patient's chemosensitivity is not assessed to be high (e.g., less than about two standard deviations of an age matched general population chemosensitivity, or other relevant numeric threshold) then the patient may not be a suitable candidate for a carotid body ablation procedure. Conversely, a patient with chemoreceptor hypersensitivity (e.g., greater than or equal to about two standard deviations above normal) may proceed to have a carotid body ablation procedure. Following a carotid body ablation procedure the patient's chemosensitivity may optionally be tested again and compared to the results of the baseline test. The second test or the comparison of the second test to the baseline test may provide an indication of treatment success or suggest further intervention such as possible adjustment of drug therapy, repeating the carotid body ablation procedure with adjusted parameters or location, or performing another carotid body ablation procedure on a second carotid body if the first procedure only targeted one carotid body. It may be expected that a patient having chemoreceptor hypersensitivity or hyperactivity may return to about a normal sensitivity or activity following a successful carotid body ablation procedure.

In an alternative protocol for selecting a patient for a carotid body ablation, patients with high peripheral chemosensitivity or carotid body activity (e.g., ≥about 2 standard deviations above normal) alone or in combination with other clinical and physiologic parameters may be particularly good candidates for carotid body ablation therapy if they further respond positively to temporary blocking of carotid body activity. A prospective patient suffering from a cardiac, metabolic, or pulmonary disease may be selected to be tested to assess the baseline peripheral chemoreceptor sensitivity. A patient without high chemosensitivity may not be a plausible candidate for a carotid body ablation procedure. A patient with a high chemosensitivity may be given a further assessment that temporarily blocks a carotid body chemoreflex. For example a temporary block may be done chemically, for example using a chemical such as intravascular dopamine or dopamine-like substances, intravascular alpha-2 adrenergic agonists, oxygen, in general alkalinity, or local or topical application of atropine externally to the carotid body. A patient having a negative response to the temporary carotid body block test (e.g., sympathetic activity index such as respiration, HR, heart rate variability, MSNA, vasculature resistance, etc. is not significantly altered) may be a less plausible candidate for a carotid body ablation procedure. Conversely, a patient with a positive response to the temporary carotid body block test (e.g., respiration or index of sympathetic activity is altered significantly) may be a more plausible candidate for a carotid body ablation procedure.

There are a number of potential ways to conduct a temporary carotid body block test. Hyperoxia (e.g., higher than normal levels of $PO_2$) for example, is known to partially block (about a 50%) or reduce afferent sympathetic response of the carotid body. Thus, if a patient's sympathetic activity indexes (e.g., respiration, HR, HRV, MSNA) are reduced by hyperoxia (e.g., inhalation of higher than normal levels of $O_2$) for 3-5 minutes, the patient may be a particularly plausible candidate for carotid body ablation therapy. A sympathetic response to hyperoxia may be achieved by monitoring minute ventilation (e.g., reduction of more than 20-30% may indicate that a patient has carotid body hyperactivity). To evoke a carotid body response, or compare it to carotid body response in normoxic conditions, $CO_2$ above 3-4% may be mixed into the gas inspired by the patient (nitrogen content will be reduced) or another pharmacological agent can be used to invoke a carotid body response to a change of $CO_2$, pH or glucose concentration. Alternatively, "withdrawal of hypoxic drive" to rest state respiration in response to breathing a high concentration $O_2$ gas mix may be used for a simpler test.

An alternative temporary carotid body block test involves administering a sub-anesthetic amount of anesthetic gas halothane, which is known to temporarily suppress carotid body activity. Furthermore, there are injectable substances such as dopamine that are known to reversibly inhibit the carotid body. However, any substance, whether inhaled, injected or delivered by another manner to the carotid body that affects carotid body function in the desired fashion may be used.

Another alternative temporary carotid body block test involves application of cryogenic energy to a carotid body (i.e., removal of heat). For example, a carotid body or its nerves may be cooled to a temperature range between about $-15°$ C. to $0°$ C. to temporarily reduce nerve activity or blood flow to and from a carotid body thus reducing or inhibiting carotid body activity.

An alternative method of assessing a temporary carotid body block test may involve measuring pulse pressure. Non-invasive pulse pressure devices such as Nexfin (made by BMEYE, based in Amsterdam, The Netherlands) can be used to track beat-to-beat changes in peripheral vascular resistance. Patients with hypertension or CHF may be sensitive to temporary carotid body blocking with oxygen or injection of a blocking drug. The peripheral vascular resistance of such patients may be expected to reduce substantially in response to carotid body blocking. Such patients may be good candidates for carotid body ablation therapy.

Yet another index that may be used to assess if a patient may be a good candidate for carotid body ablation therapy is increase of baroreflex, or baroreceptor sensitivity, in response to carotid body blocking. It is known that hyperactive chemosensitivity suppresses baroreflex. If carotid body activity is temporarily reduced the carotid sinus baroreflex (baroreflex sensitivity (BRS) or baroreflex gain) may be expected to increase. Baroreflex contributes a beneficial parasympathetic component to autonomic drive. Depressed BRS is often associated with an increased incidence of death and malignant ventricular arrhythmias. Baroreflex is measurable using standard non-invasive methods. One example is spectral analysis of RR interval of ECG and systolic blood pressure variability in both the high- and low-frequency bands. An increase of baroreflex gain in response to temporary blockade of carotid body can be a good indication for permanent therapy. Baroreflex sensitivity can also be measured by heart rate response to a transient rise in blood pressure induced by injection of phenylephrine.

An alternative method involves using an index of glucose tolerance to select patients and determine the results of carotid body blocking or removal in diabetic patients. There is evidence that carotid body hyperactivity contributes to progression and severity of metabolic disease.

In general, a beneficial response can be seen as an increase of parasympathetic or decrease of sympathetic tone in the overall autonomic balance. For example, Power Spectral Density (PSD) curves of respiration or HR can be calculated using nonparametric Fast Fourier Transform algorithm (FFT). FFT parameters can be set to 256-64 k buffer size, Hamming window, 50% overlap, 0 to 0.5 or 0.1 to 1.0 Hz range. HR and respiratory signals can be analyzed for the same periods of time corresponding to (1) normal unblocked carotid body breathing and (2) breathing with blocked carotid body.

Power can be calculated for three bands: the very low frequency (VLF) between 0 and 0.04 Hz, the low frequency band (LF) between 0.04-0.15 Hz and the high frequency band (HF) between 0.15-0.4 Hz. Cumulative spectral power in LF and HF bands may also be calculated; normalized to total power between 0.04 and 0.4 Hz (TF=HF+LF) and expressed as % of total. Natural breathing rate of CHF patient, for example, can be rather high, in the 0.3-0.4 Hz range.

The VLF band may be assumed to reflect periodic breathing frequency (typically 0.016 Hz) that can be present in CHF patients. It can be excluded from the HF/LF power ratio calculations.

The powers of the LF and HF oscillations characterizing heart rate variability (HRV) appear to reflect, in their reciprocal relationship, changes in the state of the sympathovagal (sympathetic to parasympathetic) balance occurring during numerous physiological and pathophysiological conditions. Thus, increase of HF contribution in particular can be considered a positive response to carotid body blocking.

Another alternative method of assessing carotid body activity comprises nuclear medicine scanning, for example with ocretide, somatostatin analogues, or other substances produced or bound by the carotid body.

Furthermore, artificially increasing blood flow may reduce carotid body activation. Conversely artificially reducing blood flow may stimulate carotid body activation. This may be achieved with drugs known in the art to alter blood flow.

There is a considerable amount of scientific evidence to demonstrate that hypertrophy of a carotid body often accompanies disease. A hypertrophied (i.e., enlarged) carotid body may further contribute to the disease. Thus identification of patients with enlarged carotid bodies may be instrumental in determining candidates for therapy. Imaging of a carotid body may be accomplished by angiography performed with radiographic, computer tomography, or magnetic resonance imaging.

It should be understood that the available measurements are not limited to those described above. It may be possible to use any single or a combination of measurements that reflect any clinical or physiological parameter effected or changed by either increases or decreases in carotid body function to evaluate the baseline state, or change in state, of a patient's chemosensitivity.

There is a considerable amount of scientific evidence to demonstrate that hypertrophy of a carotid body often accompanies disease. A hypertrophied or enlarged carotid body may further contribute to the disease. Thus identification of patients with enlarged carotid bodies may be instrumental in determining candidates for therapy.

Further, it is possible that although patients do not meet a preselected clinical or physiological definition of high peripheral chemosensitivity (e.g., greater than or equal to about two standard deviations above normal), administration of a substance that suppresses peripheral chemosensitivity may be an alternative method of identifying a patient who is a candidate for the proposed therapy. These patients may have a different physiology or co-morbid disease state that, in concert with a higher than normal peripheral chemosensitivity (e.g., greater than or equal to normal and less than or equal to about 2 standard deviations above normal), may still allow the patient to benefit from carotid body ablation. The proposed therapy may be at least in part based on an objective that carotid body ablation will result in a clinically significant or clinically beneficial change in the patient's physiological or clinical course. It is reasonable to believe that if the desired clinical or physiological changes occur even in the absence of meeting the predefined screening criteria, then therapy could be performed.

Cryogenic ablation of a peripheral chemoreceptor (e.g., carotid body or aortic body) via an endovascular approach in patients having sympathetically mediated disease and augmented chemoreflex (e.g., high afferent nerve signaling from a carotid body to the central nervous system as in some cases indicated by high peripheral chemosensitivity) has been conceived to reduce peripheral chemosensitivity and reduce afferent signaling from peripheral chemoreceptors to the central nervous system. The expected reduction of chemoreflex activity and sensitivity to hypoxia and other stimuli such as blood flow, blood $CO_2$, glucose concentration or blood pH can directly reduce afferent signals from chemoreceptors and produce at least one beneficial effect such as the reduction of central sympathetic activation, reduction of the sensation of breathlessness (dyspnea), vasodilation, increase of exercise capacity, reduction of blood pressure, reduction of sodium and water retention, redistribution of blood volume to skeletal muscle, reduction of insulin resistance, reduction of hyperventilation, reduction of tachypnea, reduction of hypocapnia, increase of baroreflex and barosensitivity of baroreceptors, increase of vagal tone, or improve symptoms of a sympathetically mediated disease and may ultimately slow down the disease progression and extend life. It is understood that a sympathetically mediated disease that may be treated with carotid body ablation may comprise elevated sympathetic tone, an elevated sympathetic/parasympathetic activity ratio, autonomic imbalance primarily attributable to central sympathetic tone being abnormally or undesirably high, or heightened sympathetic tone at least partially attributable to afferent excitation traceable to hypersensitivity or hyperactivity of a peripheral chemoreceptor (e.g., carotid body). In some important clinical cases where baseline hypocapnia or tachypnea is present, reduction of hyperventilation and breathing rate may be expected. It is understood that hyperventilation in the context herein means respiration in excess of metabolic needs on the individual that generally leads to slight but significant hypocapnea (blood $CO_2$ partial pressure below normal of approximately 40 mmHg, for example in the range of 33 to 38 mmHg).

Patients having CHF or hypertension concurrent with heightened peripheral chemoreflex activity and sensitivity often react as if their system was hypercapnic even if it is not. The reaction is to hyperventilate, a maladaptive attempt to rid the system of $CO_2$, thus overcompensating and creating a hypocapnic and alkalotic system. Some researchers attribute this hypersensitivity/hyperactivity of the carotid body to the direct effect of catecholamines, hormones circulating in excessive quantities in the blood stream of CHF patients. The procedure may be particularly useful to treat such patients who are hypocapnic and possibly alkalotic resulting from high tonic output from carotid bodies. Such patients are particularly predisposed to periodic breathing and central apnea hypopnea type events that cause arousal, disrupt sleep, cause intermittent hypoxia and are by themselves detrimental and difficult to treat.

It is appreciated that periodic breathing of Cheyne Stokes pattern occurs in patients during sleep, exercise and even at rest as a combination of central hypersensitivity to $CO_2$, peripheral chemosensitivity to $O_2$ and $CO_2$ and prolonged circulatory delay. All these parameters are often present in CHF patients that are at high risk of death. Thus, patients with hypocapnea, CHF, high chemosensitivity and prolonged circulatory delay, and specifically ones that exhibit periodic breathing at rest or during exercise or induced by hypoxia are likely beneficiaries of the proposed therapy.

Hyperventilation is defined as breathing in excess of a person's metabolic need at a given time and level of activity. Hyperventilation is more specifically defined as minute ventilation in excess of that needed to remove CO2 from blood in order to maintain blood $CO_2$ in the normal range (e.g., around 40 mmHg partial pressure). For example, patients with arterial blood $PCO_2$ in the range of 32-37 mmHg can be considered hypocapnic and in hyperventilation.

For the purpose of this disclosure hyperventilation is equivalent to abnormally low levels of carbon dioxide in the blood (e.g., hypocapnia, hypocapnea, or hypocarbia) caused by overbreathing. Hyperventilation is the opposite of hypoventilation (e.g., underventilation) that often occurs in patients with lung disease and results in high levels of carbon dioxide in the blood (e.g., hypercapnia or hypercarbia).

A low partial pressure of carbon dioxide in the blood causes alkalosis, because CO2 is acidic in solution and reduced CO2 makes blood pH more basic, leading to lowered plasma calcium ions and nerve and muscle excitability. This condition is undesirable in cardiac patients since it can increase probability of cardiac arrhythmias.

Alkalemia may be defined as abnormal alkalinity, or increased pH of the blood. Respiratory alkalosis is a state due to excess loss of carbon dioxide from the body, usually as a result of hyperventilation. Compensated alkalosis is a form in which compensatory mechanisms have returned the pH toward normal. For example, compensation can be achieved by increased excretion of bicarbonate by the kidneys.

Compensated alkalosis at rest can become uncompensated during exercise or as a result of other changes of metabolic balance. Thus the invented method is applicable to treatment of both uncompensated and compensated respiratory alkalosis.

Tachypnea means rapid breathing. For the purpose of this disclosure a breathing rate of about 6 to 16 breaths per minute at rest is considered normal but there is a known benefit to lower rate of breathing in cardiac patients. Reduction of tachypnea can be expected to reduce respiratory dead space, increase breathing efficiency, and increase parasympathetic tone.

Therapy Example: Role of Chemoreflex and Central Sympathetic Nerve Activity in CHF Chronic elevation in sympathetic nerve activity (SNA) is associated with the development and progression of certain types of hypertension and contributes to the progression of congestive heart failure (CHF). It is also known that sympathetic excitatory cardiac, somatic, and central/peripheral chemoreceptor reflexes are abnormally enhanced in CHF and hypertension (Ponikowski, 2011 and Giannoni, 2008 and 2009).

Arterial chemoreceptors serve an important regulatory role in the control of alveolar ventilation. They also exert a powerful influence on cardiovascular function.

Delivery of Oxygen ($O_2$) and removal of Carbon Dioxide ($CO_2$) in the human body is regulated by two control systems, behavioral control and metabolic control. The metabolic ventilatory control system drives our breathing at rest and ensures optimal cellular homeostasis with respect to pH, partial pressure of carbon dioxide ($PCO_2$), and partial pressure of oxygen ($PO_2$). Metabolic control uses two sets of chemoreceptors that provide a fine-tuning function: the central chemoreceptors located in the ventral medulla of the brain and the peripheral chemoreceptors such as the aortic chemoreceptors and the carotid body chemoreceptors. The carotid body, a small, ovoid-shaped (often described as a grain of rice), and highly vascularized organ is situated in or near the carotid bifurcation, where the common carotid artery branches in to an internal carotid artery (IC) and external carotid artery (EC). The central chemoreceptors are sensitive to hypercapnia (high $PCO_2$), and the peripheral chemoreceptors are sensitive to hypercapnia and hypoxia (low blood $PO_2$). Under normal conditions activation of the sensors by their respective stimuli results in quick ventilatory responses aimed at the restoration of cellular homeostasis.

As early as 1868, Pflüger recognized that hypoxia stimulated ventilation, which spurred a search for the location of oxygen-sensitive receptors both within the brain and at various sites in the peripheral circulation. When Corneille Heymans and his colleagues observed that ventilation increased when the oxygen content of the blood flowing through the bifurcation of the common carotid artery was reduced (winning him the Nobel Prize in 1938), the search for the oxygen chemosensor responsible for the ventilatory response to hypoxia was largely considered accomplished.

The persistence of stimulatory effects of hypoxia in the absence (after surgical removal) of the carotid chemoreceptors (e.g., the carotid bodies) led other investigators, among them Julius Comroe, to ascribe hypoxic chemosensitivity to other sites, including both peripheral sites (e.g., aortic bodies) and central brain sites (e.g., hypothalamus, pons and rostral ventrolateral medulla). The aortic chemoreceptor, located in the aortic body, may also be an important chemoreceptor in humans with significant influence on vascular tone and cardiac function.

Carotid Body Chemoreflex:

The carotid body is a small cluster of chemoreceptors (also known as glomus cells) and supporting cells located near, and in most cases directly at, the medial side of the bifurcation (fork) of the carotid artery, which runs along both sides of the throat.

These organs act as sensors detecting different chemical stimuli from arterial blood and triggering an action potential in the afferent fibers that communicate this information to the Central Nervous System (CNS). In response, the CNS activates reflexes that control heart rate (HR), renal function and peripheral blood circulation to maintain the desired homeostasis of blood gases, $O_2$ and $CO_2$, and blood pH. This closed loop control function that involves blood gas chemoreceptors is known as the carotid body chemoreflex (CBC). The carotid body chemoreflex is integrated in the CNS with the carotid sinus baroreflex (CSB) that maintains arterial blood pressure. In a healthy organism these two reflexes maintain blood pressure and blood gases within a narrow physiologic range. Chemosensors and barosensors in the aortic arch contribute redundancy and fine-tuning function to the closed loop chemoreflex and baroreflex. In addition to sensing blood gasses, the carotid body is now understood to be sensitive to blood flow and velocity, blood Ph and glucose concentration. Thus it is understood that in conditions such as hypertension, CHF, insulin resistance, diabetes and other metabolic derangements afferent signaling of carotid body nerves may be elevated. Carotid body hyperactivity may be present even in the absence of detectable hypersensitivity to hypoxia and hypercapnia that are traditionally used to index carotid body function. The purpose of the proposed therapy is therefore to remove or reduce afferent neural signals from a carotid body and reduce carotid body contribution to central sympathetic tone.

The carotid sinus baroreflex is accomplished by negative feedback systems incorporating pressure sensors (e.g., baroreceptors) that sense the arterial pressure. Baroreceptors also exist in other places, such as the aorta and coronary arteries. Important arterial baroreceptors are located in the carotid sinus, a slight dilatation of the internal carotid artery 201 at its origin from the common carotid. The carotid sinus baroreceptors are close to but anatomically separate from the carotid body. Baroreceptors respond to stretching of the arterial wall and communicate blood pressure information to CNS. Baroreceptors are distributed in the arterial walls of the carotid sinus while the chemoreceptors (glomus cells) are clustered inside the carotid body. This makes the selective reduction of chemoreflex described in this application possible while substantially sparing the baroreflex.

The carotid body exhibits great sensitivity to hypoxia (low threshold and high gain). In chronic Congestive Heart Failure (CHF), the sympathetic nervous system activation that is directed to attenuate systemic hypoperfusion at the initial phases of CHF may ultimately exacerbate the progression of cardiac dysfunction that subsequently increases the extracardiac abnormalities, a positive feedback cycle of progressive deterioration, a vicious cycle with ominous consequences. It was thought that much of the increase in the sympathetic nerve activity (SNA) in CHF was based on an increase of sympathetic flow at a level of the CNS and on the depression of arterial baroreflex function. In the past several years, it has been demonstrated that an increase in the activity and sensitivity of peripheral chemoreceptors (heightened chemoreflex function) also plays an important role in the enhanced SNA that occurs in CHF.

Role of Altered Chemoreflex in CHF:

As often happens in chronic disease states, chemoreflexes that are dedicated under normal conditions to maintaining homeostasis and correcting hypoxia contribute to increase the sympathetic tone in patients with CHF, even under normoxic conditions. The understanding of how abnormally enhanced sensitivity of the peripheral chemosensors, particularly the carotid body, contributes to the tonic elevation in SNA in patients with CHF has come from several studies in animals. According to one theory, the local angiotensin receptor system plays a fundamental role in the enhanced carotid body chemoreceptor sensitivity in CHF. In addition, evidence in both CHF patients and animal models of CHF has clearly established that the carotid body chemoreflex is often hypersensitive in CHF patients and contributes to the tonic elevation in sympathetic function. This derangement derives from altered function at the level of both the afferent and central pathways of the reflex arc. The mechanisms responsible for elevated afferent activity from the carotid body in CHF are not yet fully understood.

Regardless of the exact mechanism behind the carotid body hypersensitivity, the chronic sympathetic activation driven from the carotid body and other autonomic pathways leads to further deterioration of cardiac function in a positive feedback cycle. As CHF ensues, the increasing severity of cardiac dysfunction leads to progressive escalation of these alterations in carotid body chemoreflex function to further elevate sympathetic activity and cardiac deterioration. The trigger or causative factors that occur in the development of CHF that sets this cascade of events in motion and the time course over which they occur remain obscure. Ultimately, however, causative factors are tied to the cardiac pump failure and reduced cardiac output. According to one theory, within the carotid body, a progressive and chronic reduction in blood flow may be the key to initiating the maladaptive changes that occur in carotid body chemoreflex function in CHF.

There is sufficient evidence that there is increased peripheral and central chemoreflex sensitivity in heart failure, which is likely to be correlated with the severity of the disease. There is also some evidence that the central chemoreflex is modulated by the peripheral chemoreflex. According to current theories, the carotid body is the predominant contributor to the peripheral chemoreflex in humans; the aortic body having a minor contribution.

Although the mechanisms responsible for altered central chemoreflex sensitivity remain obscure, the enhanced peripheral chemoreflex sensitivity can be linked to a depression of nitric oxide production in the carotid body affecting afferent sensitivity, and an elevation of central angiotensin II affecting central integration of chemoreceptor input. The enhanced chemoreflex may be responsible, in part, for the enhanced ventilatory response to exercise, dyspnea, Cheyne-Stokes breathing, and sympathetic activation observed in chronic heart failure patients. The enhanced chemoreflex may be also responsible for hyperventilation and tachypnea (e.g., fast breathing) at rest and exercise, periodic breathing during exercise, rest and sleep, hypocapnia, vasoconstriction, reduced peripheral organ perfusion and hypertension.

Dyspnea:

Shortness of breath, or dyspnea, is a feeling of difficult or labored breathing that is out of proportion to the patient's level of physical activity. It is a symptom of a variety of different diseases or disorders and may be either acute or chronic. Dyspnea is the most common complaint of patients with cardiopulmonary diseases.

Dyspnea is believed to result from complex interactions between neural signaling, the mechanics of breathing, and the related response of the central nervous system. A specific area has been identified in the mid-brain that may influence the perception of breathing difficulties.

The experience of dyspnea depends on its severity and underlying causes. The feeling itself results from a combination of impulses relayed to the brain from nerve endings in the lungs, rib cage, chest muscles, or diaphragm, combined with the perception and interpretation of the sensation by the patient. In some cases, the patient's sensation of breathlessness is intensified by anxiety about its cause. Patients describe dyspnea variously as unpleasant shortness of breath, a feeling of increased effort or tiredness in moving the chest muscles, a panicky feeling of being smothered, or a sense of tightness or cramping in the chest wall.

The four generally accepted categories of dyspnea are based on its causes: cardiac, pulmonary, mixed cardiac or pulmonary, and non-cardiac or non-pulmonary. The most common heart and lung diseases that produce dyspnea are asthma, pneumonia, COPD, and myocardial ischemia or heart attack (myocardial infarction). Foreign body inhalation, toxic damage to the airway, pulmonary embolism, congestive heart failure (CHF), anxiety with hyperventilation (panic disorder), anemia, and physical deconditioning because of sedentary lifestyle or obesity can produce dyspnea. In most cases, dyspnea occurs with exacerbation of the underlying disease. Dyspnea also can result from weakness or injury to the chest wall or chest muscles, decreased lung elasticity, obstruction of the airway, increased oxygen demand, or poor pumping action of the heart that results in increased pressure and fluid in the lungs, such as in CHF.

Acute dyspnea with sudden onset is a frequent cause of emergency room visits. Most cases of acute dyspnea involve pulmonary (lung and breathing) disorders, cardiovascular disease, or chest trauma. Sudden onset of dyspnea (acute dyspnea) is most typically associated with narrowing of the airways or airflow obstruction (bronchospasm), blockage of one of the arteries of the lung (pulmonary embolism), acute heart failure or myocardial infarction, pneumonia, or panic disorder.

Chronic dyspnea is different. Long-standing dyspnea (chronic dyspnea) is most often a manifestation of chronic or progressive diseases of the lung or heart, such as COPD, which includes chronic bronchitis and emphysema. The treatment of chronic dyspnea depends on the underlying disorder. Asthma can often be managed with a combination of medications to reduce airway spasms and removal of allergens from the patient's environment. COPD requires medication, lifestyle changes, and long-term physical rehabilitation. Anxiety disorders are usually treated with a combination of medication and psychotherapy.

Although the exact mechanism of dyspnea in different disease states is debated, there is no doubt that the CBC plays some role in most manifestations of this symptom. Dyspnea seems to occur most commonly when afferent input from peripheral receptors is enhanced or when cortical perception of respiratory work is excessive.

Surgical Removal of the Glomus and Resection of Carotid Body Nerves:

A surgical treatment for asthma, removal of the carotid body or glomus (glomectomy), was described by Japanese surgeon Komei Nakayama in 1940s. According to Nakayama in his study of 4,000 patients with asthma, approximately 80% were cured or improved six months after surgery and 58% allegedly maintained good results after five years. Komei Nakayama performed most of his surgeries while at the Chiba University during World War II. Later in the 1950's, a U.S. surgeon, Dr. Overholt, performed the Nakayama operation on 160 U.S. patients. He felt it necessary to remove both carotid bodies in only three cases. He reported that some patients feel relief the instant when the carotid body is removed, or even earlier, when it is inactivated by an injection of procaine (Novocain).

Overholt, in his paper Glomectomy for Asthma published in Chest in 1961, described surgical glomectomy the following way: "A two-inch incision is placed in a crease line in the neck, one-third of the distance between the angle of the mandible and clavicle. The platysma muscle is divided and the sternocleidomastoid retracted laterally. The dissection is carried down to the carotid sheath exposing the bifurcation. The superior thyroid artery is ligated and divided near its take-off in order to facilitate rotation of the carotid bulb and expose the medial aspect of the bifurcation. The carotid body is about the size of a grain of rice and is hidden within the adventitia of the vessel and is of the same color. The perivascular adventitia is removed from one centimeter above to one centimeter below the bifurcation. This severs connections of the nerve plexus, which surrounds the carotid body. The dissection of the adventitia is necessary in order to locate and identify the body. It is usually located exactly at the point of bifurcation on its medial aspect. Rarely, it may be found either in the center of the crotch or on the lateral wall. The small artery entering the carotid body is clamped, divided, and ligated. The upper stalk of tissue above the carotid body is then clamped, divided, and ligated."

In January 1965, the New England Journal of Medicine published a report of 15 cases in which there had been unilateral removal of the cervical glomus (carotid body) for the treatment of bronchial asthma, with no objective beneficial effect. This effectively stopped the practice of glomectomy to treat asthma in the U.S.

Winter developed a technique for separating nerves that contribute to the carotid sinus nerves into two bundles, carotid sinus (baroreflex) and carotid body (chemoreflex), and selectively cutting out the latter. The Winter technique is based on his discovery that carotid sinus (baroreflex) nerves are predominantly on the lateral side of the carotid bifurcation and carotid body (chemoreflex) nerves are predominantly on the medial side.

Neuromodulation of the Carotid Body Chemoreflex:

Hlavaka in U.S. Patent Application Publication 2010/0070004 filed Aug. 7, 2009, describes implanting an electrical stimulator to apply electrical signals, which block or inhibit chemoreceptor signals in a patient suffering dyspnea. Hlavaka teaches that "some patients may benefit from the ability to reactivate or modulate chemoreceptor functioning." Hlavaka focuses on neuromodulation of the chemoreflex by selectively blocking conduction of nerves that connect the carotid body to the CNS. Hlavaka describes a traditional approach of neuromodulation with an implantable electric pulse generator that does not modify or alter tissue of the carotid body or chemoreceptors.

The central chemoreceptors are located in the brain and are difficult to access. The peripheral chemoreflex is modulated primarily by carotid bodies that are more accessible. Previous clinical practice had very limited clinical success with the surgical removal of carotid bodies to treat asthma in 1940s and 1960s.

Additional Exemplary Embodiments

1. A method for ablating the function of a carotid body in a patient comprising:
   a. locating a region in a patient including a carotid body,
   b. inserting into the patient a cryo-ablation device comprising an elongated body having a distal region and a proximal region, the distal region includes a cryo-ablation element;
   c. advancing the distal region of said cryo-ablation device through the body of the patient;
   d. positioning the distal region of the cryo-ablation device proximate to the region containing the carotid body;
   e. ablating tissue in the region that includes the carotid body by cooling the region with the cryo-ablation element;
   f. withdrawing the cryo-ablation device from the patient.
2. The method of claim 1 wherein the step of locating includes defining a three-dimensional region of a carotid septum.
3. The method of claim 2 wherein the carotid septum is a triangular segment having boundaries at a saddle of a carotid bifurcation, sidewalls defined by an internal carotid artery and an external carotid artery, and a base extending between the internal and external carotid arteries.
4. The method of claim 3 wherein the base is within 15 mm of the saddle.
5. The method of claims 3 and 4 wherein the boundaries of the carotid septum include a first plane tangent to the lateral walls of the internal and external carotid arteries and a second plane tangent to the medial walls of the internal and external carotid arteries.
6. The method of claim 1 wherein the cryo-ablation device comprises a vascular catheter.
7. The method of claims 1 to 6 wherein the cryo-ablation device is advanced through the vascular system of the patient.
8. The method of claims 1 to 5 wherein the cryo-ablation device comprises a percutaneous probe.
9. The method of claim 8 wherein the cryo-ablation device is advanced through the neck of the patient.
10. The method of claims 1 to 5 further comprising determining a value of a parameter associated with the cooling by the cryo-ablation element, and using the value to set the cooling by said cryo-ablation device.
11. The method of claim 10 wherein a parameter is cryo-ablation element temperature.
12. The method of claim 10 wherein a parameter is duration of cooling.
13. The method of claim 10 wherein a parameter is cryo-ablation element contact force.
14. The method of claim 10 wherein a parameter is number of cooling cycles.
15. The method of claim 10 wherein a parameter is the location of the cryo-ablation element within the patient.
16. The method of any claims 1 to 15 wherein cooling results in tissue temperature below zero degrees centigrade within the region including the carotid body.
17. The method of claim 16 wherein tissue temperatures below zero degrees centigrade is substantially limited to said region.
18. The method of claim 1 further comprising placing upon the body of the patient an ultrasonic imaging device configured for imaging the region including a carotid body.
19. The method of claim 18 wherein the ultrasonic imaging device is configured for extracorporeal imaging.
20. The method of claim 18 wherein the ultrasonic imaging device is configured for intravascular imaging.
21. The method of any claims 18 to 20 wherein the ultrasonic imaging device is configured to image a boundary between frozen tissue and not frozen tissue.
22. The method of claims 18 to 21 wherein at least one cryo-ablation parameter is adjusted based on an imaged spatial relationship between the boundary of the frozen and not frozen tissue, and the boundary of said region.
23. The method of claim 1 further comprising placing an embolization protection device into an internal carotid artery prior to the ablation.
24. The method of claim 1 wherein the means for locating the region including a carotid body comprises an imaging study.
25. The method of claim 24 wherein the size of the carotid body is determined.
26. The method of claims 24 and 25 wherein the imaging study comprises Computed Tomography Angiography.
27. The method of claims 24 and 25 wherein the imaging study comprises MR Angiography.
28. The method of claims 24 and 25 wherein the imaging study comprises Fluoroscopic Angiography.
29. The method of claims 24 and 25 wherein the imaging study comprises sonography.
30. The method of claim 1 wherein the function of a carotid body is stimulated.
31. The method of claim 30 wherein the stimulation comprises application of electrical energy to the region including the carotid body.
32. The method of claim 30 wherein the stimulation comprises administration of a chemical agent.
33. The method of claim 30 wherein the stimulation comprises a manipulation in the composition of inhaled gas.
34. The method of any of claims 30 to 33 wherein the carotid body is stimulated prior to said ablation and after said ablation.
35. The method of claim 1 wherein the function of a carotid body is blocked.

36. The method of claim 35 wherein the blockade comprises application of electrical energy to the region including the carotid body.
37. The method of claim 35 wherein the blockade comprises administration of a chemical agent.
38. The method of claim 35 wherein the blockade comprises a manipulation in the composition of inhaled gas
39. The method of any of claims 35 to 38 wherein the carotid body is blocked prior to said ablation and after said ablation.
40. The method of claim 1 further comprising steps b through e repeated with the cryo-ablation element placed in at least one additional location.
41. The method of either of claims 1 and 40 further comprising repeating steps b through e with the cryo-ablation element at the same location.
42. The method of any claims 1 to 41 wherein the cryo-ablation element comprises a temperature sensor.
43. The method of claim 42 wherein the temperature sensor is connected to a source of cry-ablation fluid by electrical wires within the body of the cryo-ablation device.
44. The method of claims 42 and 43 wherein the temperature sensor is configured for controlling the source of cryo-ablation fluid in order to maintain the cryo-ablation element at a selected cryo-ablation temperature.
45. The method of claims 6 and 7 wherein the wherein the functional length of the catheter is greater than 90 cm.
46. The method of claims 6 and 7 wherein the catheter comprises a lumen configured for use with a standard guide wire.
47. The method of claim 46 wherein the guide wire is between 0.014" and 0.038: diameter.
48. The method of any claims 6, 7, 44 through 47 wherein the catheter comprises a braided shaft.
49. The method of any claims 6, 7, 44 through 48 wherein the catheter comprises a deflectable longitudinal segment in the region of the distal end, and a non-deflectable longitudinal segment immediately proximal to said deflectable segment.
50. The method of claim 49 wherein the deflectable longitudinal segment is configured for user actuation by means of an internal pull wire in communication with the distal end of the catheter and a handle in the vicinity of the proximal end of the catheter comprising an actuator.
51. The method of claims 49 and 50 wherein the length of the deflectable longitudinal segment is between 5 mm and 18 mm long.
52. The method of any claims 49 through 51 wherein the actuator is configured to apply a predetermined force of contact between the cryo-ablation element and a vascular wall.
53. The method of claim 6 wherein the catheter comprises at least one electrode in the region of the distal end.
54. The method of claims 6 and 53 wherein the cryo-ablation element is further configured as an electrode.
55. The method of claims 53 and 54 wherein the electrode(s) is configured to electrically stimulate carotid body function.
56. The method of any claims 53 through 55 wherein the electrode(s) is configured to electrically block carotid body function.
57. The method of any claims 53 through 56 wherein the electrode(s) is connectable to a source of electrical energy by means of an electrical conducting wire(s) located within the catheter between the electrode(s) and an electrical connector located in the region of the proximal end of the catheter.
58. The method of claim 1 wherein the cryo-ablation element comprises a cryogenic chamber.
59. The method of claim 58 wherein the cryogenic chamber comprises a liquid refrigerant evaporation chamber
60. The method of claims 58 and 59 wherein the cryogenic chamber comprises a cryogenic gas expansion chamber.
61. The method of claim 58 wherein the ablation element temperature is preselected in a range of 0 Deg. C. to −180 Deg. C.
62. The method of any claims 10 to 17 wherein the parameters of cryo-ablation are selected for reversible ablation.
63. The method of claim 62 wherein the reversible ablation results in a physiological response predictive of a permanent ablation.
64. The method of claim 63 wherein the physiological response is indicative of a carotid body ablation.
65. The method of claims 62 to 64 wherein the physiological response is a change in at least one physiological parameter comprising heart rate, heart rate variability, respiration rate, respiration volume, and blood pressure.
66. The method of claim 62 wherein the reversible ablation results in a physiological response indicative of an undesirable ablation effect.
67. The method of claim 66 wherein the physiological response is indicative of an ablation of at least one vital nervous structure comprising a vagal nerve, a sympathetic nerve, a hypoglossal nerve or a baroreflex nervous structure.
68. The method of any claims 62 to 67 wherein parameters for permanent ablation are selected in part based on the physiological response to the reversible ablation.
69. The method of any claims 62 to 68 wherein a permanent ablation is performed following a reversible ablation.
70. The method of claim 6 wherein the catheter comprises a balloon at the level of the cryo-ablation element.
71. The method of claim 7 wherein the cryo-ablation element is held in forced contact with the wall of a vascular structure in the region including the carotid body by inflation of a balloon.
72. The method of claims 70 and 71 wherein the balloon is inflated to a predetermined pressure.
73. The method of claims 70 to 72 wherein the balloon is inflated with a gas configured to thermally insulate the cryo-ablation element from vascular blood.
74. The method of any claims 70 to 73 wherein the balloon is substantially non-compliant.
75. The method of any claims 70 to 74 wherein the balloon diameter is preselected based on patient vascular anatomy.
76. The method of claims 8 and 9 wherein the percutaneous probe is a rigid needle structure.
77. The method of claims 8 and 9 wherein the percutaneous probe is a flexible structure configured for use with a percutaneous sheath.
78. The method of claim 76 wherein the caliber of the percutaneous probe is between 12 gage and 18 gage.
79. The method of claim 77 wherein the caliber of the percutaneous probe is between 4 French and 8 French.
80. The method of any claims 76 to 79 wherein the functional length of the percutaneous probe is at least 4 cm.

81. A device for ablating the function of a carotid body comprising:
   a. a vascular catheter configured for use in the vicinity of a carotid artery bifurcation comprising a distal end and a proximal end,
   b. a cryo-ablation element disposed in the region of the distal end;
   c. a balloon adjacent to the cryo-ablation element;
   d. a braided structure disposed within the wall of the catheter between the distal end and the proximal end;
   e. a connection between the cryo-ablation element and a source of cryo-ablation fluid, and
   f. a connection between the balloon and a balloon inflation mechanism;
   whereby, the balloon is configured for inflation and to apply a contact force between the cryo-ablation element and the wall of a vascular structure and to thermally insulate the cryo-ablation element from vascular blood.

82. The device of claim 81 wherein the catheter is configured for use through a carotid access sheath no greater than 8 French.

83. The device of any claims 81 and 82 wherein the working length of the catheter is at least 90 cm.

84. The device of any claims 81 to 83 wherein the catheter is configured for use with a guide wire.

85. The device of claim 84 wherein the guide wire is between 0.014" to 0.038" diameter.

86. The device of claim 81 wherein the cryo-ablation element comprises a cryo chamber.

87. The device of claim 86 wherein the cryo-ablation chamber is configured as a liquid evaporation chamber.

88. The device of claim 86 wherein the cryo-ablation chamber is configured as a gas expansion chamber.

89. The device of any claims 86 to 88 wherein a temperature sensor is associated with the cryo-ablation element.

90. The device of claim 89 wherein the temperature sensor is connectable to a source cryogenic fluid and configured to control the source of cryogenic fluid and maintain the cryo-ablation element at a selected temperature.

91. The device of any claims 81 to 85 wherein the balloon is fabricated from a compliant material.

92. The device of any claims 81 to 85 wherein the balloon is fabricated from a non-compliant material.

93. The device of any claims 81 to 92 wherein the catheter is manufactured with a user choice of balloon diameters between 3 mm and 18 mm.

94. The device of claim 81 further comprising at least one electrode configured for electrical neural modulation.

95. The device of claim 94 wherein the cryo-ablation element is configured as an electrode.

96. The device of claim 94 an 95 wherein the electrode(s) is connectable to a source of electricity configured for neural modulation.

97. The device of claim 81 wherein the cryo-ablation element is configured as an RF ablation electrode.

98. The device of claim 97 wherein the cryo-ablation element is connectable to a source of RF ablation energy.

99. The device of any claims 81 to 98 further comprises at least one radiopaque element disposed in the region of the distal end configured to provide the user with an unambiguous fluoroscopic indication of the position of the cryo-ablation element in a blood vessel.

100. A system for ablation carotid body function is a patient comprising:
   a. a vascular catheter configured for use in the vicinity of a carotid bifurcation comprising a distal end and a proximal end, a cryo-ablation element disposed in the region of the distal end, a balloon adjacent to the cryo-ablation element, a braided structure disposed within the wall of the catheter between the distal end and the proximal end, a connection between the cryo-ablation element and a source of cryo-ablation fluid, and a connection between the balloon and a balloon inflation mechanism,
   b. a console comprising a source of cryo-ablation fluid, a means for controlling said cryo-ablation fluid, a user interface configured to provide the user with a selection of ablation parameters, and to provide the user with indications of the status of the console, and the status of ablation activity, and a means to activate and deactivate an ablation,
   c. an umbilical cable configured to connect the console to the vascular catheter;
   whereby, the vascular catheter provides the means of user placement of the cryo-ablation element into an optimal position within the vascular system for ablation of carotid body function, and the console provides the user with a selection of cryo-ablation parameters and supplies the cryo-ablation element with cryo-ablation fluid.

101. The system of claim 100 further comprises a means for electrical neural modulation.

102. The system of claim 100 further comprises a means for RF ablation.

103. The method of claim 7 wherein the cryo-ablation device is advanced through the arterial system into a carotid artery.

104. The method of claim 7 wherein the cryo-ablation device is advanced through the venous system into an internal jugular vein.

105. The method of claim 7 wherein the cryo-ablation catheter is advanced through the venous system into a facial vein.

106. A device for percutaneous cryo-ablation of the function of a carotid body comprising:
   a. a rigid hollow elongated structure having a distal region and a proximal region;
   b. a cryo-ablation element in the distal region;
   c. a warming element distal to the cryo-ablation element;
   d. a fluid connection between the cryo-ablation element and a source of cryogenic fluid;
   e. an electrical connection between the warming element and a source of electrical warming energy.

107. A method for percutaneous ablation of a carotid body comprising:
   a. determining a pathway void of vital structures between a point on the neck of a patient and a region including a carotid body;
   b. inserting a needle into the patient through the pathway;
   c. inserting a guide wire through the needle;
   d. replacing the needle with a percutaneous sheath;
   e. inserting a cryo-ablation probe into the region through the sheath;
   f. activating the cryo-ablation probe;
   whereby, the function of the carotid body is substantially diminished by the activation of the cryo-ablation probe.

108. The method of claim 107 wherein the cryo-ablation probe comprises a needle like structure with a cryo-ablation element in the region of the distal tip.

109. The method of claim 108 wherein the cryo-ablation probe comprises a warming element at the distal tip configured to warm tissue distal to the tip simultaneously with cryo-ablation.

110. The method of claims 107 to 109 wherein the warming element is activated in during cryo-ablation.

111. The method of claim 110 wherein the temperature of the warming element is maintained between zero and 42 degrees centigrade.

112. The method of any claims 107 to 111 wherein the boundary between frozen tissue and not frozen tissue is monitored by an ultrasonic imaging device during cryo-ablation.

113. The device of claim 106 wherein the warming element is associated with a temperature sensor configured to control warming.

114. The device of claims 106 and 113 wherein the cryo-ablation element is associated with a temperature sensor configured to control a cryo-ablation.

115. The method of claim 109 wherein the warming element is maintained at a determined temperature.

116. The method of claim 109 wherein the warming element protects vital nervous structures from cryo-ablation.

117. A method for catheter-based chemoreceptor neuromodulation, the method comprising:
  a. positioning a catheter having a therapeutic cryogenic element within an artery of a human patient; and
  b. reducing neural traffic within the patient due to the therapeutic cryogenic element,
  wherein reducing the neural traffic therapeutically treats a diagnosed condition of disease associated with autonomic imbalance.

118. A method for catheter-based chemoreceptor ablation, the method comprising:
  a. positioning a catheter having an cryogenic ablation element within an artery of a human patient; and
  b. reducing chemoreceptor neural traffic within the patient due to the cryogenic ablation element,
  wherein reducing the chemoreceptor neural traffic therapeutically treats a diagnosed condition of disease associated with autonomic imbalance.

119. A method for treating a patient comprising:
  a. locating a region in the patient including a carotid body,
  b. inserting into the patient a cryogenic ablation device, said cryogenic ablation device comprising a distal region and a proximal region, an ablation element mounted to said distal region, a connection extending through the cryogenic ablation device from the distal region to the proximal region wherein a cryogen is delivered to the proximal region through the connection to the ablation element;
  c. positioning the distal region in the vascular structure at a location proximate to said carotid body region, wherein the ablation element abuts a wall of said vascular structure;
  d. while the ablation element abuts the wall, transferring heat energy from said ablation device to the wall or from the wall to the ablation device to ablate tissue in the region that includes the carotid body, and
  e. withdrawing the ablation device from the patient.

120. A device for catheter-based carotid body cryo-ablation, the device comprising:
  a. an elongated structure having distal region and a proximal region and a lumen running between;
  b. a cryo-ablation element in the distal region having two deployable arms; and
  c. a means for transporting cryogen through the lumen from the proximal region to the cryo-ablation element and along the deployable arms.

121. A device of claim 120 wherein the cryogen is maintained at a near critical point and the means for transporting cryogen is two cryogen delivery tubes passing within the lumen and along the two deployable arms and returned to the proximal region in two cryogen return tubes.

122. A device of claim 120 wherein the deployable arms comprise Nitinol strips having preformed bends configured to deploy the cryo-ablation element into a V-shape.

We claim:

1. A method for cryo-ablating target tissue within a carotid septum of a patient, the method comprising:
  advancing a cryo-ablation catheter into an artery of the patient, the cryo-ablation catheter comprising first and second arms;
  passing the first arm into an external carotid artery of the patient and into engagement with a wall of the external carotid artery adjacent a carotid septum;
  passing the second arm into an internal carotid artery of the patient and into engagement with a wall of the internal carotid artery adjacent the carotid septum; and
  delivering a cryogen fluid through the first and second arms to ablate at least a portion of the carotid septum.

2. The method of claim 1 wherein advancing a cryo-ablation catheter into an artery of the patient comprises advancing the first and second arms in collapsed delivery configurations.

3. The method of claim 1 further comprising retracting a sheath to cause the first and second arms to deploy to preformed delivery configurations.

4. The method of claim 3 wherein retracting the sheath causes the first and second arms to deploy to preformed delivery configurations in which they extend about 30 to about 60 degrees away from an axis of the catheter.

5. The method of claim 3 wherein the passing steps comprise advancing the first and second arms distally into engagement with the external and internal carotid arteries.

* * * * *